United States Patent
Talasaz et al.

(10) Patent No.: US 10,889,858 B2
(45) Date of Patent: *Jan. 12, 2021

(54) METHODS AND SYSTEMS FOR DETECTING GENETIC VARIANTS

(71) Applicant: GUARDANT HEALTH, INC., Redwood City, CA (US)

(72) Inventors: AmirAli Talasaz, Atherton, CA (US); Stefanie Ann Ward Mortimer, Morgan Hill, CA (US)

(73) Assignee: GUARDANT HEALTH, INC., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/714,579

(22) Filed: Dec. 13, 2019

(65) Prior Publication Data

US 2020/0131568 A1    Apr. 30, 2020

Related U.S. Application Data

(63) Continuation of application No. 16/672,267, filed on Jan. 7, 2020, which is a continuation of application No. 16/601,168, filed on Oct. 14, 2019, which is a continuation of application No. 15/892,178, filed on Feb. 8, 2018, which is a continuation of application No. 14/861,989, filed on Sep. 22, 2015, now Pat. No. 9,920,366, which is a continuation of application No. PCT/US2014/072383, filed on Dec. 24, 2014.

(60) Provisional application No. 61/948,509, filed on Mar. 5, 2014, provisional application No. 61/921,456, filed on Dec. 28, 2013.

(51) Int. Cl.
  *C12P 19/34* (2006.01)
  *C12Q 1/6869* (2018.01)
  *C12Q 1/6886* (2018.01)
  *G16B 15/00* (2019.01)

(52) U.S. Cl.
  CPC ......... *C12Q 1/6869* (2013.01); *C12Q 1/6886* (2013.01); *C12Q 2535/122* (2013.01); *C12Q 2600/158* (2013.01); *G16B 15/00* (2019.02)

(58) Field of Classification Search
  None
  See application file for complete search history.

(56) References Cited

U.S. PATENT DOCUMENTS

| | | |
|---|---|---|
| 4,725,536 A | 2/1988 | Fritsch et al. |
| 4,942,124 A | 7/1990 | Church |
| 5,124,246 A | 6/1992 | Urdea et al. |
| 5,149,625 A | 9/1992 | Church et al. |
| 5,200,314 A | 4/1993 | Urdea |
| 5,424,186 A | 6/1995 | Fodor et al. |
| 5,424,413 A | 6/1995 | Hogan et al. |
| 5,445,934 A | 8/1995 | Fodor et al. |
| 5,604,097 A | 2/1997 | Brenner |
| 5,635,352 A | 6/1997 | Urdea et al. |
| 5,635,400 A | 6/1997 | Brenner |
| 5,648,245 A | 7/1997 | Fire et al. |
| 5,654,413 A | 8/1997 | Brenner |
| 5,656,731 A | 8/1997 | Urdea |
| 5,658,737 A | 8/1997 | Nelson et al. |
| 5,714,330 A | 2/1998 | Brenner et al. |
| 5,744,305 A | 4/1998 | Fodor et al. |
| 5,759,778 A | 6/1998 | Li et al. |
| 5,763,175 A | 6/1998 | Brenner |
| 5,800,992 A | 9/1998 | Fodor et al. |
| 5,846,719 A | 12/1998 | Brenner et al. |
| 5,854,033 A | 12/1998 | Lizardi |
| 5,871,928 A | 2/1999 | Fodor et al. |
| 5,925,525 A | 7/1999 | Fodor et al. |
| 5,935,793 A | 8/1999 | Wong |
| 5,952,170 A | 9/1999 | Stroun et al. |
| 5,968,740 A | 10/1999 | Fodor et al. |
| 5,981,176 A | 11/1999 | Wallace |
| 5,981,179 A | 11/1999 | Lorinez et al. |
| 6,013,445 A | 1/2000 | Albrecht et al. |

(Continued)

FOREIGN PATENT DOCUMENTS

| | | |
|---|---|---|
| CN | 102933721 A | 2/2013 |
| EP | 0799897 B1 | 6/2006 |

(Continued)

OTHER PUBLICATIONS

Ingolia, et al. Genome-wide analysis in vivo of translation with nucleotide resolution using ribosome profiling. Science. Apr. 10, 2009;324(5924)118-23. Epub Feb. 12, 2009.
Instructions for Norit Rapid DNA Ligation Kit (Nov. 6, 2004).
International search report and written opinion dated Apr. 3, 2015 for PCT/US2014/072383.
International search report and written opinion dated May 7, 2012 for PCT/IB2011/003160.
International search report and written opinion dated Jun. 6, 2012 for PCT/US2011/065291.

(Continued)

*Primary Examiner* — Kenneth R Horlick
(74) *Attorney, Agent, or Firm* — Timothy A. Hott

(57) ABSTRACT

Disclosed herein in are methods and systems for determining genetic variants (e.g., copy number variation) in a polynucleotide sample. A method for determining copy number variations includes tagging double-stranded polynucleotides with duplex tags, sequencing polynucleotides from the sample and estimating total number of polynucleotides mapping to selected genetic loci. The estimate of total number of polynucleotides can involve estimating the number of double-stranded polynucleotides in the original sample for which no sequence reads are generated. This number can be generated using the number of polynucleotides for which reads for both complementary strands are detected and reads for which only one of the two complementary strands is detected.

29 Claims, 11 Drawing Sheets

(56) References Cited

U.S. PATENT DOCUMENTS

| | | |
|---|---|---|
| 6,020,124 A | 2/2000 | Sorenson |
| 6,040,138 A | 3/2000 | Lockhart et al. |
| 6,046,005 A | 4/2000 | Ju et al. |
| 6,060,596 A | 5/2000 | Lerner et al. |
| 6,117,631 A | 9/2000 | Nilsen |
| 6,124,092 A | 9/2000 | O'Neill et al. |
| 6,138,077 A | 10/2000 | Brenner |
| 6,140,489 A | 10/2000 | Brenner |
| 6,172,214 B1 | 1/2001 | Brenner |
| 6,197,506 B1 | 3/2001 | Fodor et al. |
| 6,235,475 B1 | 5/2001 | Brenner et al. |
| 6,242,186 B1 | 6/2001 | Salonen |
| 6,268,152 B1 | 7/2001 | Fodor et al. |
| 6,284,460 B1 | 9/2001 | Fodor et al. |
| 6,300,077 B1 | 10/2001 | Shuber et al. |
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,395,491 B1 | 5/2002 | Fodor et al. |
| 6,406,848 B1 | 6/2002 | Bridgham et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,489,114 B2 | 12/2002 | Laayoun et al. |
| 6,492,121 B2 | 12/2002 | Kurane et al. |
| 6,498,012 B2 | 12/2002 | Laken |
| 6,503,718 B2 | 1/2003 | Shuber et al. |
| 6,512,105 B1 | 1/2003 | Hogan et al. |
| 6,514,699 B1 | 2/2003 | O'Neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,582,908 B2 | 6/2003 | Fodor et al. |
| 6,586,177 B1 | 7/2003 | Shuber |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,849,403 B1 | 2/2005 | Shuber |
| 6,849,404 B2 | 2/2005 | Park et al. |
| 6,852,488 B2 | 2/2005 | Fodor et al. |
| 6,858,412 B2 | 2/2005 | Willis et al. |
| 6,964,846 B1 | 11/2005 | Shuber |
| 7,163,789 B2 | 1/2007 | Chen et al. |
| 7,208,275 B2 | 4/2007 | Gocke et al. |
| 7,406,385 B2 | 7/2008 | Sorenson |
| 7,410,764 B2 | 8/2008 | Gocke et al. |
| 7,424,368 B2 | 9/2008 | Huang et al. |
| 7,424,371 B2 | 9/2008 | Kamentsky |
| 7,537,897 B2 | 5/2009 | Brenner et al. |
| 7,700,286 B2 | 4/2010 | Stroun et al. |
| 7,704,687 B2 | 4/2010 | Wang et al. |
| 7,727,720 B2 | 6/2010 | Dhallan |
| 7,803,929 B2 | 9/2010 | Melkonyan et al. |
| 7,811,757 B2 | 10/2010 | Shuber |
| 7,822,555 B2 | 10/2010 | Huang et al. |
| 7,824,889 B2 | 11/2010 | Vogelstein et al. |
| 7,838,647 B2 | 11/2010 | Hahn et al. |
| 7,915,015 B2 | 3/2011 | Vogelstein et al. |
| 7,935,487 B2 | 5/2011 | Gocke et al. |
| 7,937,225 B2 | 5/2011 | Mishra et al. |
| 7,957,913 B2 | 6/2011 | Chinitz et al. |
| 7,972,817 B2 | 7/2011 | Kopreski |
| 7,981,612 B2 | 7/2011 | Shuber et al. |
| 8,094,312 B2 | 1/2012 | Ulmer |
| 8,168,385 B2 | 5/2012 | Brenner |
| 8,195,415 B2 | 6/2012 | Fan et al. |
| 8,209,130 B1 | 6/2012 | Kennedy et al. |
| 8,216,789 B2 | 7/2012 | Disis et al. |
| 8,236,532 B2 | 8/2012 | Ronaghi et al. |
| 8,361,726 B2 | 1/2013 | Gocke et al. |
| 8,383,338 B2 | 2/2013 | Kitzman et al. |
| 8,383,345 B2 | 2/2013 | Shendure et al. |
| 8,455,193 B2 | 6/2013 | Travers et al. |
| 8,470,996 B2 | 6/2013 | Brenner |
| 8,481,292 B2 | 7/2013 | Casbon et al. |
| 8,603,749 B2 | 12/2013 | Gillevet |
| 8,685,678 B2 | 4/2014 | Casbon et al. |
| 8,697,408 B2 | 4/2014 | Kucera et al. |
| 8,704,165 B2 | 4/2014 | Huang |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,775,092 B2 | 7/2014 | Colwell et al. |
| 8,835,358 B2 | 9/2014 | Fodor et al. |
| 8,865,410 B2 | 10/2014 | Shendure et al. |
| 9,018,365 B2 | 4/2015 | Brenner |
| 9,085,798 B2 | 7/2015 | Chee |
| 9,260,753 B2 | 2/2016 | Xie et al. |
| 9,340,830 B2 | 5/2016 | Lipson et al. |
| 9,376,719 B2 | 6/2016 | Eijk et al. |
| 9,404,156 B2 | 8/2016 | Hicks et al. |
| 9,476,095 B2 | 10/2016 | Vogelstein et al. |
| 9,598,731 B2 | 3/2017 | Talasaz |
| 9,752,188 B2 | 9/2017 | Schmitt et al. |
| 9,834,822 B2 | 12/2017 | Talasaz |
| 9,840,743 B2 | 12/2017 | Talasaz |
| 9,920,366 B2 | 3/2018 | Eltoukhy et al. |
| 10,287,631 B2 | 5/2019 | Salk et al. |
| 10,370,713 B2 | 8/2019 | Salk et al. |
| 10,385,393 B2 | 8/2019 | Salk et al. |
| 10,388,403 B2 | 8/2019 | Rava et al. |
| 10,604,804 B2 | 3/2020 | Salk et al. |
| 2001/0053519 A1 | 12/2001 | Fodor et al. |
| 2002/0072058 A1 | 6/2002 | Voelker et al. |
| 2003/0003490 A1 | 1/2003 | Fan et al. |
| 2003/0049616 A1 | 3/2003 | Brenner et al. |
| 2003/0104436 A1 | 6/2003 | Morris et al. |
| 2003/0152490 A1 | 8/2003 | Trulson et al. |
| 2003/0165978 A1 | 9/2003 | Firth et al. |
| 2003/0186251 A1 | 10/2003 | Dunn et al. |
| 2003/0207300 A1 | 11/2003 | Matray et al. |
| 2004/0096892 A1 | 5/2004 | Wang et al. |
| 2004/0146901 A1 | 7/2004 | Morris et al. |
| 2004/0157243 A1 | 8/2004 | Huang et al. |
| 2004/0209299 A1 | 10/2004 | Pinter et al. |
| 2004/0259118 A1 | 12/2004 | Macevicz |
| 2005/0164241 A1 | 7/2005 | Hahn et al. |
| 2005/0221314 A1 | 10/2005 | Berlin et al. |
| 2005/0250147 A1 | 11/2005 | Macevicz |
| 2006/0035258 A1 | 2/2006 | Tadakamalla et al. |
| 2006/0046258 A1 | 3/2006 | Lapidus et al. |
| 2006/0073506 A1 | 4/2006 | Christians et al. |
| 2006/0211030 A1 | 9/2006 | Brenner |
| 2007/0020640 A1 | 1/2007 | McCloskey et al. |
| 2007/0065823 A1 | 3/2007 | Dressman et al. |
| 2007/0111233 A1 | 5/2007 | Bianchi et al. |
| 2007/0128724 A1 | 6/2007 | Miles et al. |
| 2007/0172839 A1 | 7/2007 | Smith et al. |
| 2007/0172873 A1 | 7/2007 | Brenner et al. |
| 2008/0014146 A1 | 1/2008 | Hoff et al. |
| 2008/0124721 A1 | 5/2008 | Fuchs et al. |
| 2008/0161420 A1 | 7/2008 | Shuber |
| 2008/0261204 A1 | 10/2008 | Lexow |
| 2008/0293055 A1 | 11/2008 | Freeman et al. |
| 2009/0029377 A1 | 1/2009 | Lo et al. |
| 2009/0087847 A1 | 4/2009 | Lo et al. |
| 2009/0098547 A1 | 4/2009 | Ghosh |
| 2009/0105959 A1 | 4/2009 | Braverman et al. |
| 2009/0162836 A1 | 6/2009 | Widschwendter |
| 2009/0298075 A1 | 12/2009 | Travers et al. |
| 2009/0298709 A1 | 12/2009 | Ma |
| 2009/0317818 A1 | 12/2009 | Ehrich et al. |
| 2010/0041048 A1 | 2/2010 | Diehl et al. |
| 2010/0062494 A1 | 3/2010 | Church et al. |
| 2010/0069250 A1 | 3/2010 | White et al. |
| 2010/0112575 A1 | 5/2010 | Fan et al. |
| 2010/0143932 A1 | 6/2010 | Lapidus |
| 2010/0166744 A1 | 7/2010 | Wong |

(56) References Cited

U.S. PATENT DOCUMENTS

| | | |
|---|---|---|
| 2010/0196898 A1 | 8/2010 | Sugarbaker et al. |
| 2010/0264331 A1 | 10/2010 | Sacko et al. |
| 2010/0323348 A1 | 12/2010 | Hamady et al. |
| 2010/0330571 A1 | 12/2010 | Robins et al. |
| 2011/0014607 A1 | 1/2011 | Jirtle et al. |
| 2011/0160078 A1 | 6/2011 | Fodor et al. |
| 2011/0160290 A1 | 6/2011 | Tewari |
| 2011/0171640 A1 | 7/2011 | Bhatt et al. |
| 2011/0177512 A1 | 7/2011 | Shuber |
| 2011/0183330 A1 | 7/2011 | Lo et al. |
| 2011/0201507 A1 | 8/2011 | Rava et al. |
| 2011/0230358 A1 | 9/2011 | Rava |
| 2011/0230360 A1 | 9/2011 | Stephan et al. |
| 2011/0245482 A1 | 10/2011 | Hahn et al. |
| 2011/0264376 A1 | 10/2011 | Chinitz et al. |
| 2011/0275084 A1 | 11/2011 | Byron et al. |
| 2011/0281736 A1 | 11/2011 | Drmanac et al. |
| 2011/0319272 A1 | 12/2011 | Fan et al. |
| 2012/0003637 A1 | 1/2012 | Lo et al. |
| 2012/0034685 A1 | 2/2012 | Sparks et al. |
| 2012/0046877 A1 | 2/2012 | Hyland et al. |
| 2012/0053073 A1 | 3/2012 | Kassis |
| 2012/0059594 A1 | 3/2012 | Hatchwell et al. |
| 2012/0065081 A1 | 3/2012 | Chee |
| 2012/0095697 A1 | 4/2012 | Halpern et al. |
| 2012/0100548 A1 | 4/2012 | Rava et al. |
| 2012/0164630 A1 | 6/2012 | Porreca et al. |
| 2012/0165202 A1 | 6/2012 | Porreca et al. |
| 2012/0191367 A1 | 7/2012 | Stuelpnagel et al. |
| 2012/0208706 A1 | 8/2012 | Downing et al. |
| 2012/0214163 A1 | 8/2012 | Sugarbaker et al. |
| 2012/0214678 A1 | 8/2012 | Rava et al. |
| 2012/0220478 A1 | 8/2012 | Shaffer |
| 2012/0231479 A1 | 9/2012 | Puskas et al. |
| 2012/0238464 A1 | 9/2012 | Koi et al. |
| 2012/0270212 A1 | 10/2012 | Rabinowitz et al. |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0017958 A1 | 1/2013 | Benz et al. |
| 2013/0022977 A1 | 1/2013 | Lapidus et al. |
| 2013/0029852 A1 | 1/2013 | Rava et al. |
| 2013/0034546 A1 | 2/2013 | Rava et al. |
| 2013/0040824 A1 | 2/2013 | Lo et al. |
| 2013/0053256 A1 | 2/2013 | Hubbell |
| 2013/0060483 A1 | 3/2013 | Struble et al. |
| 2013/0078626 A1 | 3/2013 | Wasserstrom et al. |
| 2013/0085681 A1 | 4/2013 | Deciu et al. |
| 2013/0096011 A1 | 4/2013 | Rava et al. |
| 2013/0102485 A1 | 4/2013 | Lee |
| 2013/0102487 A1 | 4/2013 | Cos et al. |
| 2013/0116127 A1 | 5/2013 | Schuetz et al. |
| 2013/0116130 A1 | 5/2013 | Fu et al. |
| 2013/0122499 A1 | 5/2013 | Morris et al. |
| 2013/0130923 A1 | 5/2013 | Ehrich et al. |
| 2013/0137588 A1 | 5/2013 | Shendure et al. |
| 2013/0143747 A1 | 6/2013 | Gutin et al. |
| 2013/0210643 A1 | 8/2013 | Casbon et al. |
| 2013/0210645 A1 | 8/2013 | Volgelstein et al. |
| 2013/0224743 A1 | 8/2013 | Casbon et al. |
| 2013/0237431 A1 | 9/2013 | Lo et al. |
| 2013/0237458 A1 | 9/2013 | Casbon et al. |
| 2013/0260381 A1 | 10/2013 | Ramakrishnan |
| 2013/0267424 A1 | 10/2013 | Casbon et al. |
| 2013/0288244 A1* | 10/2013 | Deciu .................. G16B 20/00 435/6.11 |
| 2013/0338933 A1 | 12/2013 | Deciu et al. |
| 2014/0011694 A1 | 1/2014 | Couronne |
| 2014/0065609 A1 | 3/2014 | Hicks et al. |
| 2014/0065630 A1 | 3/2014 | Bubnoff et al. |
| 2014/0066317 A1 | 3/2014 | Talasaz |
| 2014/0100121 A1 | 4/2014 | Lo et al. |
| 2014/0242588 A1 | 8/2014 | Boom et al. |
| 2014/0274731 A1 | 9/2014 | Raymond et al. |
| 2014/0274740 A1 | 9/2014 | Srinivasan et al. |
| 2014/0296094 A1 | 10/2014 | Domanus |
| 2014/0303008 A1 | 10/2014 | Schutz et al. |
| 2014/0336943 A1 | 11/2014 | Pellini et al. |
| 2014/0350130 A1 | 11/2014 | Sanborn et al. |
| 2014/0357500 A1 | 12/2014 | Vigneault et al. |
| 2015/0004158 A1 | 1/2015 | Shipp et al. |
| 2015/0024950 A1 | 1/2015 | Bielas et al. |
| 2015/0044687 A1 | 2/2015 | Schmitt et al. |
| 2015/0050647 A1 | 2/2015 | Luo et al. |
| 2015/0051085 A1 | 2/2015 | Vogelstein et al. |
| 2015/0065358 A1 | 3/2015 | Comstock et al. |
| 2015/0080266 A1 | 3/2015 | Volkmuth et al. |
| 2015/0087535 A1 | 3/2015 | Patel |
| 2015/0167069 A1 | 6/2015 | Schutz et al. |
| 2015/0197786 A1 | 7/2015 | Osborne et al. |
| 2015/0275289 A1 | 10/2015 | Otwinowski et al. |
| 2015/0299812 A1 | 10/2015 | Talasaz |
| 2015/0329917 A1 | 11/2015 | Shuber |
| 2015/0344970 A1 | 12/2015 | Vogelstein et al. |
| 2015/0366866 A1 | 12/2015 | Ali et al. |
| 2015/0368708 A1 | 12/2015 | Talasaz |
| 2016/0002739 A1 | 1/2016 | Schütz et al. |
| 2016/0002741 A1 | 1/2016 | Kitano et al. |
| 2016/0024576 A1 | 1/2016 | Chee |
| 2016/0026758 A1 | 1/2016 | Jabara et al. |
| 2016/0032396 A1 | 2/2016 | Diehn et al. |
| 2016/0040229 A1 | 2/2016 | Talasaz et al. |
| 2016/0046986 A1 | 2/2016 | Eltoukhy et al. |
| 2016/0053301 A1 | 2/2016 | Raymond et al. |
| 2016/0060691 A1 | 3/2016 | Giresi et al. |
| 2016/0071432 A1 | 3/2016 | Kurowski et al. |
| 2016/0115553 A1 | 4/2016 | Stephan et al. |
| 2016/0130649 A1 | 5/2016 | Xie et al. |
| 2016/0251704 A1 | 9/2016 | Talasaz et al. |
| 2016/0319345 A1 | 11/2016 | Gnerre et al. |
| 2016/0333417 A1 | 11/2016 | Talasaz |
| 2016/0376647 A1 | 12/2016 | Travers et al. |
| 2017/0051347 A1 | 2/2017 | Vogelstein et al. |
| 2017/0073774 A1 | 3/2017 | Lo et al. |
| 2017/0145516 A1 | 5/2017 | Kopetz et al. |
| 2017/0159120 A1 | 6/2017 | Eijk et al. |
| 2017/0211143 A1 | 7/2017 | Shendure et al. |
| 2017/0218459 A1 | 8/2017 | Talasaz et al. |
| 2017/0218460 A1 | 8/2017 | Talasaz |
| 2018/0023125 A1 | 1/2018 | Talasaz et al. |
| 2019/0271040 A1 | 9/2019 | Salk et al. |
| 2019/0292597 A1 | 9/2019 | Salk et al. |
| 2019/0338358 A1 | 11/2019 | Salk et al. |
| 2019/0352714 A1 | 11/2019 | Salk et al. |

FOREIGN PATENT DOCUMENTS

| | | |
|---|---|---|
| EP | 1647600 A2 | 6/2006 |
| EP | 2110442 A1 | 10/2009 |
| EP | 3070177 A1 | 9/2016 |
| EP | 3178941 A1 | 6/2017 |
| WO | 1997007241 A1 | 2/1997 |
| WO | 1997010365 A1 | 3/1997 |
| WO | 1999028505 A1 | 6/1999 |
| WO | 2000058516 A2 | 10/2000 |
| WO | 2002056014 A2 | 7/2002 |
| WO | 2005080604 A2 | 9/2005 |
| WO | 2005111242 A2 | 11/2005 |
| WO | 2006102264 A1 | 9/2006 |
| WO | 2007037678 A2 | 4/2007 |
| WO | 2008070144 A2 | 6/2008 |
| WO | 2008154317 A1 | 12/2008 |
| WO | 2009152928 A2 | 12/2009 |
| WO | 2011060240 A1 | 5/2011 |
| WO | 2011087760 A2 | 7/2011 |
| WO | 2011091046 A1 | 7/2011 |
| WO | 2011103236 A2 | 8/2011 |
| WO | 2011140510 A2 | 11/2011 |
| WO | 2011155833 A2 | 12/2011 |
| WO | 2012012693 A2 | 1/2012 |
| WO | 2012014877 A1 | 2/2012 |
| WO | 2012019200 A2 | 2/2012 |
| WO | 2012028746 A1 | 3/2012 |
| WO | 2012038839 A2 | 3/2012 |

(56) References Cited

FOREIGN PATENT DOCUMENTS

| | | | |
|---|---|---|---|
| WO | 2012042374 | A2 | 4/2012 |
| WO | 2012048341 | A1 | 4/2012 |
| WO | 2012054873 | A2 | 4/2012 |
| WO | 2012066451 | A1 | 5/2012 |
| WO | 2012071621 | A1 | 6/2012 |
| WO | 2012088348 | A2 | 6/2012 |
| WO | 2012106559 | A1 | 8/2012 |
| WO | 2012129363 | A2 | 9/2012 |
| WO | 2012142213 | A2 | 10/2012 |
| WO | 2012142611 | A2 | 10/2012 |
| WO | 2012148477 | A1 | 11/2012 |
| WO | 2012103031 | A3 | 1/2013 |
| WO | 2013019075 | A2 | 2/2013 |
| WO | 2013033721 | A1 | 3/2013 |
| WO | 2013106737 | A1 | 7/2013 |
| WO | 2013123442 | A1 | 8/2013 |
| WO | 2013130512 | A2 | 9/2013 |
| WO | 2013130674 | A1 | 9/2013 |
| WO | 2013138510 | A1 | 9/2013 |
| WO | 2013142213 | A1 | 9/2013 |
| WO | 2013142389 | A1 | 9/2013 |
| WO | 2013148496 | A1 | 10/2013 |
| WO | 2013159035 | A2 | 10/2013 |
| WO | 2013173394 | A2 | 11/2013 |
| WO | 2013181170 | A1 | 12/2013 |
| WO | 2013188471 | A2 | 12/2013 |
| WO | 2013190441 | A2 | 12/2013 |
| WO | 2014004726 | A1 | 1/2014 |
| WO | 2014014497 | A1 | 1/2014 |
| WO | 2014015319 | A1 | 1/2014 |
| WO | 2014039556 | A1 | 3/2014 |
| WO | 2014093330 | A1 | 6/2014 |
| WO | 2014145078 | A1 | 9/2014 |
| WO | 2014149134 | A2 | 9/2014 |
| WO | 2014151117 | A1 | 9/2014 |
| WO | 2014152990 | A1 | 9/2014 |
| WO | 2015159293 | A2 | 10/2015 |
| WO | 2016015058 | A2 | 1/2016 |
| WO | 2016040901 | A1 | 3/2016 |
| WO | 2017100441 | A1 | 6/2017 |
| WO | 2017181146 | A1 | 10/2017 |

OTHER PUBLICATIONS

International search report and written opinion dated Jul. 15, 2015 for PCT/US2015/030639.
International search report and written opinion dated Sep. 5, 2014 for PCT/US2014/000048.
International search report and written opinion dated Sep. 6, 2017 for PCT Application No. US-201727809.
International search report and written opinion dated Nov. 18, 2013 for PCT/US2013/058061.
Invitrogen Instructions for T4 DNA Ligase (May 5, 2002).
IPR2018-00130, Petition for Inter Partes Review of U.S. Pat. No. 9,598,731, dated Nov. 7, 2018.
IPR2019-00130, Decision Denying Inter Partes Review U.S. Pat. No. 9,598,731, issued Jun. 5, 2019.
IPR2019-00130, Preliminary Response to Petition for Inter Partes Review U.S. Pat. No. 9,598,731, filed Mar. 6, 2019.
IPR2019-00634, Decision Instituting Inter Partes Review U.S. Pat. No. 9,840,743, issued Aug. 19, 2019.
IPR2019-00634, Petition for Inter Partes Review of U.S. Pat. No. 9,840,743, dated Feb. 1, 2019.
IPR2019-00636 & 637, Exhibit 3001 Memo for Inter Partes Review of U.S. Pat. No. 9,902,992, dated Jul. 1, 2019.
IPR2019-00636 & 637, Order—Conduct of the Proceedings for Inter Partes Review of U.S. Pat. No. 9,902,992, dated Jul. 22, 2019.
IPR2019-00636 and IPR2019-00637, Decision Denying Inter Partes Review U.S. Pat. No. 9,902,992, issued Aug. 20, 2019.
IPR2019-00636, Petition for Inter Partes Review of U.S. Pat. No. 9,902,992, dated Feb. 1, 2019.
IPR2019-00637, Petition for Inter Partes Review of U.S. Pat. No. 9,902,992, dated Feb. 1, 2019.
IPR2019-00652, Decision Granting Inter Partes Review U.S. Pat. No. 9,834,822, issued Aug. 19, 2019.
IPR2019-00652, Petition for Inter Partes Review of U.S. Pat. No. 9,834,822, dated Feb. 1, 2019.
IPR2019-00653, Decision Denying Inter Partes Review U.S. Pat. No. 9,834,822, issued Aug. 19, 2019.
IPR2019-00653, Petition for Inter Partes Review of U.S. Pat. No. 9,834,822, dated Feb. 1, 2019.
Jabara, C. Capturing the cloud: High throughput sequencing of multiple individual genomes from a retroviral population. Biology Lunch Bunch Series, Training Initiatives in Biomedical & Biological Sciences of the University of North Carolina at Chapel Hill, Apr. 23, 2010.
Jabara, et al. Accurate sampling and deep sequencing of the HIV-1 protease gene using a Primer ID. (Paper # 665), The 18th Annual Conference on Retroviruses and Opportunistic Infections, Boston, Massachusetts, Mar. 2011.
Jabara, et al. Accurate sampling and deep sequencing of the HIV-1 protease gene using a Primer ID. Proc Natl Acad Sci U S A. Dec. 13, 2011;108(50):20166-71. doi: 10.1073/pnas.1110064108. Epub Nov. 30, 2011.
Jahr, et al. DNA fragments in the blood plasma of cancer patients: quantitations and evidence for their origin from apoptotic and necrotic cells. Cancer Res. Feb. 15, 2001;61(4):1659-65.
Jeronimo, et al. Quantitative GSTP1 hypermethylation in bodily fluids of patients with prostate cancer. Urology. Dec. 2002;60(6):1131-5.
Jiang, H. et al., "SeqMap: mapping massive amount of oligonucleotides to the genome," Bioinformatics 2008, 24(20):2395-2396.
Kanagawa. Bias and artifacts in multitemplate polymerase chain reactions (PCR), 2003, Journal of Bioscience and Bioengineering, vol. 96, No. 4, p. 317-323.
Kao,W-C. et al., "BayesCall: A model-based base-calling algorithm for high-throughput short-read sequencing," Genome Res. 2009 19(10), 1884-1895.
Karow, J. "Hopkins Team Develops Method to Improve Rare Mutation Detection for Early Cancer Dx" Genome Web (2011) 3 pages.
Kennedy, S.R. et al., "Detecting ultralow-frequency mutations by Duplex Sequencing" Nature Protocols (2014) 9(11):2586-2606.
Kennedy, S.R. et al., "Ultra-Sensitive Sequencing Reveals an Age-Related Increase in Somatic Mitochondrial Mutations That Are Inconsistent with Oxidative Damage" PLoS Genetics (2013) 9:e1003794.
Kennedy, S.R. et al., "Detecting ultralow-frequency mutations by Duplex Sequencing," Nat. Protoc. 2014, 9(11), 2586-2606.
Kimura, et al. EGFR mutation status in tumour-derived DNA from pleural effusion fluid is a practical basis for predicting the response to gefitinib. Br J Cancer Nov. 20, 2006;95(10):1390-5. Epub Oct. 24, 2006.
Kinde, et al. Detection and quantification of rare mutations with massively parallel sequencing. Proc Natl Acad Sci U S A. Jun. 7, 2011;108(23):9530-5. doi: 10.1073/pnas.1105422108. Epub May 17, 2011.
Kinde, et al. Supplemental Information, Detection and quantification of rare mutations with massively parallel sequencing. Proc Natl Acad Sci U S A. Jun. 7, 2011;108(23):1-10.
Kinde, I. et al., "Evaluation of DNA from the Papanicolaou Test to Detect Ovarian and Endometrial Cancers," Sci. Transl. Med. 2013, 5(167):167ra4.
Kinde, I. et al., "FAST-SeqS: a simple and efficient method for the detection of aneuploidy by massively parallel sequencing," PLoS One 2012, 7(7), e41162.
Kircher, M. et al., "Improved base calling for the Illumina Genome Analyzer using machine learning strategies," Genome Biol. 2009, 10(8), R83.
Kirsch, S. et al. "Sequence error storms and the landscape of mutations in cancer," Proc. Natl. Acad. Sci. USA 2012, 109(36), 14289-14290.
Kivioja, T., et al. Counting absolute numbers of molecules using unique molecular identifiers. Nat Methods. Nov. 20, 2011;9(1):72-4. doi: 10.1038/nmeth.1778.

(56) References Cited

OTHER PUBLICATIONS

Koboldt, D.C.et al., "The next-generation sequencing revolution and its impact on genomics," Cell 2013, 155(1), 27-38.
Koboldt, et al. Massively parallel sequencing approaches for characterization of structural variation. Aug. 12, 2011. Methods Mol Biol. 2012;838:369-84. doi: 10.1007/978-1-61779-507-7_18.
Kolble, et al. Microsatellite alterations in serum DNA of patients with colorectal cancer. Lab Invest. Sep. 1999;79(9):1145-50.
Konig, et al. iCLIP reveals the function of hnRNAP particles in splicing at individual nucleotide resolution, Jul. 2010, Nature Structural & Molecular Biology, 17(7):909-916.
Kopreski, et al. Detection of mutant K-ras DNA in plasma or serum of patients with colorectal cancer. Br J Cancer. 1997;76(10):1293-9.
Korbel, J.O. et al., "Paired-end mapping reveals extensive structural variation in the human genome," Science 2007, 318(5849), 420-426.
"Blood Plasma" Oxford Dictionary of Biochemistry and Molecular Biology 81 (2d ed. 2006).
"LB-246/12—Detection of circulating tumor DNA in early stage cancers," Available at https://www.genomeweb.com/cancer/ngs-error-correction-method-described-aacr-excitement-grows-early-cancer-detection, Accessed on Apr. 26, 2017.
"Cohesive End," Oxford Dictionary of Biochemistry and Molecular Biology 132 (2d ed. 2006).
"Control," Oxford Dictionary of Biochemistry and Molecular Biology (2d ed. 2006), 143.
Ajay, S.S. et al., "Accurate and comprehensive sequencing of personal genomes," Genome Res. 2011, 21(9), 1498-1505.
Albert, T.J. et al., "Direct selection of human genomic loci by microarray hybridization," Nat. Methods 2007, 4(11), 903-905.
Alkan, et al. Personalized copy number and segmental duplication maps using next-generation sequencing. Nat Genet. Oct. 2009;41(10):1061-7. doi: 10.1038/ng.437. Epub Aug. 30, 2009.
Andersson, et al. Bayesian detection of periodic mRNA time profiles without use of training examples. BMC Bioinformatics. Feb. 9, 2006;7:63.
Angeloni, D. Molecular analysis of deletions in human chromosome 3p21 and the role of resident cancer genes in disease. Brief Funct Genomic Proteomic. Mar. 2007;6(1):19-39. Epub May 24, 2007.
Ansorge "Next-generation DNA sequencing techniques." New Biotechnology, 25(4):195-203 (2009).
Appel, Maryke. Part II: It's all about conversion. Kapa Biosystems. Accessed Mar. 29, 2017. Printed Apr. 11, 2017. 5 pages. URL:https://www.kapabiosystems.com/ngs/part-ii-conversion/.
Arneson, N. et al., "Whole-Genome Amplification by Adaptor-Ligation PCR of Randomly Sheared Genomic DNA (PRSG)," CSH Protocols, 2008, 3(1).
Ashford, Monica. NGS Error Correction Method Described at AACR as Excitement Grows for Early Cancer Detection. Genomeweb.com. Apr. 5, 2017. 3 pages. URL:https://www.genomeweb.com/cancerings-error-correction-method-described-aacr-excitement-grows-early-cancer-detection.
Atanur, et al. The genome sequence of the spontaneously hypertensive rat: Analysis and functional significance. Genome Res. Jun. 2010;20(6):791-803. doi: 10.1101/gr.103499.109. Epub Apr. 29, 2010.
Audic, et al. "The Significance of Digital Gene Expression Profiles." Genome Research, 7: 986-995 (1997).
Barzon, et al. Evaluation of circulating thyroid-specific transcripts as markers of thyroid cancer relapse. Int J Cancer. Jul. 20, 2004;110(6):914-20.
Bendich, et al. Circulating DNA as a possible factor in oncogenesis. Science. Apr. 16, 1965;148(3668):374-6.
Bentley, D.R. et al., "Accurate Whole Human Genome Sequencing using Reversible Terminator Chemistry," Nature, 2008, 456(7218):53-59.
Bettegowda et al., "Detection of Circulating Tumor DNA in Early- and Late-Stage Human Malignancies," Sci. Transl. Med. 2014, 6(224):224ra24.

Bianchi, D.W. et al. "Genome-Wide Fetal Aneuploidy Detection by Maternal Plasma DNA Sequencing," Obstetrics & Gynecology, (2012) 119(5), 1-12.
Bonaldo, et al. Normalization and subtraction: two approaches to facilitate gene discovery. Genome Res. Sep. 1996;6(9):791-806.
Bowcock, et al. Exclusion of the retinoblastoma gene and chromosome 13q as the site of a primary lesion for human breast cancer. Am J Hum Genet. Jan. 1990;46(1):12-7.
Braha, et al. Simultaneous stochastic sensing of divalent metal ions. Nature Biotechnology, 18: 1005-1007 (2000).
Bremnes, et al. Circulating tumour-derived DNA and RNA markers in blood: a tool for early detection, diagnostics, and follow-up? Lung Cancer. Jul. 2005;49(1):1-12.
Brenner, et al. "Gene expression analysis by massively parallel signature sequencing (MPSS) on microbead arrays." Nature Biotechnology, 18: 630-634 (2000).
Brenner, et al. In vitro cloning of complex mixtures of DNA on microbeads: physical separation of differentially expressed cDNAs. Proc Natl Acad Sci U S A. Feb. 15, 2000;97(4):1665-70.
Bryzgunova,O. et al., "A reliable method to concentrate circulating DNA," Analytical Biochem., 2010, 408:354-356.
Campbell, et al. Identification of somatically acquired rearrangements in cancer using genome-wide massively parallel paired-end sequencing. Nat Genet. Jun. 2008;40(6):722-9. doi: 10.1038/ng.128. Epub Apr. 27, 2008.
Caramazza, et al. Chromosome 1 abnormalities in myeloid malignancies: a literature survey and karyotype-phenotype associations. Eur J Haematol. Mar. 2010;84(3):191-200. doi: 10.1111/j.1600-0609.2009.01392.x. Epub Nov. 30, 2009.
Carr, et al. Inferring relative proportions of DNA variants from sequencing electropherograms. Bioinformatics. Dec. 15, 2009;25(24):3244-50. doi: 10.1093/bioinformatics/btp583. Epub Oct. 9, 2009.
CASAVA v1.8.2 User Guide http://gensoft.pasteur.fr/docs/casava/1.8.2/CASAVA_1_8_2_UG_15011196C.pdf (Oct. 2011).
Casbon, et al. A method for counting PCR template molecules with application to next-generation sequencing. Nucleic Acids Res. Jul. 2011;39(12):e81. doi: 10.1093/nar/gkr217. Epub Apr. 13, 2011.
Castle, et al. DNA copy number, including telomeres and mitochondria, assayed using next-generation sequencing. BMC Genomics. Apr. 16, 2010;11:244. doi: 10.1186/1471-2164-11-244.
Chang, et al. Detection of allelic imbalance in ascitic supernatant by digital single nucleotide polymorphism analysis. Clin Cancer Res. Aug. 2002;8(8):2580-5.
Chee, et al. "Accessing genetic information with high-density DNA arrays." Science, 274: 610-614 (1996).
Chee. "Enzymatic multiplex DNA sequencing." Nucleic Acids Research, 19(12): 3301-3305 (1991).
Chen, et al. Microsatellite alterations in plasma DNA of small cell lung cancer patients. Nat Med. Sep. 1996;2(9):1033-5.
Chin, et al. A SNP in a let-7 microRNA complementary site in the KRAS 3' untranslated region increases non-small cell lung cancer risk. Cancer Res. Oct. 15, 2008;68(20):8535-40. doi: 10.1158/0008-5472.CAN-08-2129.
Chiu, et al. Non-invasive prenatal assessment of trisomy 21 by multiplexed maternal plasma DNA sequencing: large scale validity study. BMJ. Jan. 11, 2011;342:c7401. doi: 10.1136/bmj.c7401.
Chiu, et al. Quantitative analysis of circulating mitochondrial DNA in plasma. Clin Chem. May 2003;49(5):719-26.
Chiu, R.W.K. et al. "Noninvasive prenatal diagnosis of fetal chromosomal aneuploidy by massively parallel genomic sequencing of DNA in maternal plasma" PNAS (2008) 105(51):20458-20463.
Church, et al. "Multiplex DNA sequencing." Science, 240: 185-188 (1988).
Cook, et al. Methylated DNA labels for marking objects. Biotechnol Lett. Jan. 2003;25(1):89-94.
Costello, et al. Discovery and characterization of artifactual mutations in deep coverage targeted capture sequencing data due to oxidative DNA damage during sample preparation. Nucleic Acids Res. Apr. 1, 2013;41(6):e67. doi: 10.1093/nar/gks1443. Epub Jan. 8, 2013.

(56) References Cited

OTHER PUBLICATIONS

Coulet, et al. Detection of plasma tumor DNA in head and neck squamous cell carcinoma by microsatellite typing and p53 mutation analysis. Cancer Res. Feb. 1, 2000;60(3):707-11.
Cox, J. "Bar coding objects with DNA." Analyst. May 2001;126(5):545-7.
Cox. Bar coding objects with DNA. Analyst. May 2001;126(5):545-7.
Craig, et al. Identification of genetic variants using bar-coded multiplexed sequencing. Nat Methods. Oct. 2008;5(10):887-93. doi: 10.1038/nmeth.1251. Epub Sep. 14, 2008.
Daines, et al. High-throughput multiplex sequencing to discover copy number variants in *Drosophila*. Genetics. Aug. 2009;182(4):935-41. doi: 10.1534/genetics.109.103218. Epub Jun. 15, 2009.
D'Antoni, et al. Rapid quantitative analysis using a single molecule counting approach. Anal Biochem. May 1, 2006;352(1):97-109. Epub Feb. 10, 2006.
Koyanagi, et al. Association of circulating tumor cells with serum tumor-related methylated DNA in peripheral blood of melanoma patients. Cancer Res. Jun. 15, 2006;66(12):6111-7.
Krimmel, J.D. et al., "Ultra-deep sequencing detects ovarian cancer cells in peritoneal fluid and reveals somatic TP53 nutations in noncancerous tissues," Proc. Natl. Acad. Sci. USA 2016, 113(21), 6005-6010.
Kukita, Y. et al. "High-fidelity target sequencing of individual molecules identified using barcode sequences: de novo detection and absolute quantitation of mutations in plasma cell-free DNA from cancer patients" DNA Research (2015) 22(4):269-277.
Lam, et al. Plasma DNA as a prognostic marker for stroke patients with negative neuroimaging within the first 24 h of symptom onset. Resuscitation. Jan. 2006;68(1):71-8. Epub Dec. 1, 2005.
Lanman, et al., Analytical and Clinical Validation of a Digital Sequencing Panel for Quantitative, Highly Accurate Evaluation of Cell-Free Circulating Tumor DNA PLoS One, Oct. 2015, 10(10), e0140712. doi:10.1371/journal.oone.0140712.
Larson, et al. A single molecule view of of gene expression. Trends Cell Biol. Nov. 2009;19(11):630-7. Epub Oct. 8, 2009.
Leary, et al. Detection of chromosomal alterations in the circulation of cancer patients with whole-genome sequencing. Sci Transl Med. Nov. 28, 2012;4(162):162ra154. doi: 10.1126/scitranslmed.3004742.
Leary, et al. Development of personalized tumor biomarkers using massively parallel sequencing. Sci Transl Med. Feb. 24, 2010;2(20):20ra14. doi: 10.1126/scitranslmed.3000702.
Lecomte, et al. Detection of free-circulating tumor-associated DNA in plasma of colorectal cancer patients and its association with prognosis. Int J Cancer Aug. 10, 2002;100(5):542-8.
Ledergerber, C. et al., "Base-calling for next-generation sequencing platforms," Brief Bioinform. 2011 12(5), 489-497.
Leon, et al. Free DNA in the serum of cancer patients and the effect of therapy. Cancer Res. Mar. 1977;37(3):646-50.
Leung, et al. Plasma Epstein-Barr viral deoxyribonucleic acid quantitation complements tumor-node-metastasis staging prognostication in nasopharyngeal carcinoma. J Clin Oncol. Dec. 1, 2006;24(34):5414-8.
Li, et al. Mapping short DNA sequencing reads and calling variants using mapping quality scores. Genome Res. Nov. 2008;18(11):1851-8. doi: 10.1101/gr.078212.108. Epub Aug. 19, 2008.
Li, et al. Structure-independent and quantitative ligation of single-stranded DNA. Anal Biochem. Feb. 15, 2006;349(2):242-6. Epub Nov. 18, 2005.
Li, H. et al "Fast and accurate short read alignment with Burrows—Wheeler transform," Bioinformatics 2009, 25(14), 1754-1760.
Liang, K.-C. et al., "Bayesian basecalling for DNA sequence analysis using hidden Markov models," IEE/ACM Trans. Comput. Biol. Bioinform. 2007 4(3), 430-440.
Liao, G.J.W et al., "Targeted massively parallel sequencing of maternal plasma DNA permits efficient and unbiased detection of fetal alleles," Clin. Chem. 2011, 57(1), 92-101.
Lizardi, et al. Mutation detection and single-molecule counting using isothermal rolling-circle amplification. Nat Genet. Jul. 1998;19(3):225-32.
Lo, et al. Quantitative Analysis of Cell-free Epstein-Barr Virus DNA in Plasma of Patients with Nasopharyngeal Carcinoma, Cancer Research, 59(6):1188-1191 (Mar. 1999).
Lo, Y M D et al. "Quantitative analysis of fetal DNA in maternal plasma and serum: implications for noninvasive prenatal diagnosis," Am. J. Hum. Genet. 1998, 62(4), 768-775.
Lo, Y.M.D. et al. "Maternal Plasma DNA Sequencing Reveals the Genome-Wide Genetic and Mutational Profile of the Fetus," Sci Transl Med (2010) 2(61):1-13.
Lockhart, et al. Expression monitoring by hybridization to high-density oligonucleotide arrays. Nature Biotechnology, 14: 1675-1680 (1996).
Lodes, et al. Novel Chimera-Free, High Efficiency Library Preparation for NGS Plafforms.Poster. Presented at the Plant & Animal Genome XX Conference. San Diego, California. Jan. 14-18, 2012. 1 page.
Lucito, et al. Detecting gene copy number fluctuations in tumor cells by microarray analysis of genomic representations. Genome Res. Nov. 2000;10(11):1726-36.
Lucito, et al. Representational Oligonucleotide Microarray Analysis: A High-Resolution Method to Detect Genome Copy Number Variation. Genome Research (2003), 13: 2291-2305.
Lunter, G. et al., "Stampy: A statistical algorithm for sensitive and fast mapping of Illumina sequence reads," Genome Res. 2011, 21(6):936-939.
Maamar, et al. Noise in Gene Expression Determines Cell Fate in Bacillus subtilis. Science, 317: 526-529 (2007).
Mahmud, et al. Fast MCMC sampling for hidden Markov Models to determine copy number variations. BMC Bioinformatics. Nov. 2, 2011;12:428. doi: 10.1186/1471-2105-12-428.
Makrigiorgos, et al., A PCR-Based amplification method retaining quantative difference between two complex genomes. Nature Biotech, vol. 20, No. 9, pp. 936-939 (Sep. 2002).
Mamanova, L. et al., "Target-enrichment strategies for next-generation sequencing," Nat. Methods 2010, 7(2), 111-118.
Mandel, et al. Les acides nucleiques du plasma sanguin chez l'homme. C R Seances Soc Biol Fil. Feb. 1948;142(3-4):241-3.
Marsit, et al. Epigenetic profiling reveals etiologically distinct patterns of DNA methylation in head and neck squamous cell carcinoma. Carcinogenesis. Mar. 2009;30(3):416-22. doi: 10.1093/carcin/bgp006. Epub Jan. 6, 2009.
McCloskey, et al. Encoding PCR products with batch-stamps and barcodes. Biochem Genet. Dec. 2007;45(11-12):761-7. Epub Oct. 23, 2007.
McKernon, K.J. et al., "Sequence and structural variation in a human genome uncovered by short-read, massively parallel ligation sequencing using two-base encoding," Genome Res. 2009, 19(9), 1527-1541.
Medvedev, et al. Detecting copy number variation with mated short reads. Genome Res. Nov. 2010;20(11):1613-22. doi 10.1101/gr.106344.110. Epub Aug. 30, 2010.
Mei, et al. Identification of recurrent regions of Copy-Number Variants across multiple individuals. BMC Bioinformatics. Mar. 22, 2010;11:147. doi: 10.1186/1471-2105-11-147.
Meldrum et al. Next generation sequencing for cancer diagnostics: a practical perspective. Clin Biochem Rev. Nov. 2011;32(4):177-95.
Mertes, F. et al. "Targeted enrichment of genomic DNA regions for next-generation sequencing" Brief Functional Genomics (2011) 10(6):374-386.
Metzker, M.L. "Sequencing technologies—the next generation" Nature Reviews Genetics (2010) 11:31-46.
Meyer, M. et al. "Illumina sequencing library preparation for highly multiplexed target capture and sequencing," Cold Spring Harb. Protoc. 2010, (6), prot5448.
Meyerson, M. et al. "Advances in understanding cancer genomes through second-generation sequencing" Nature Reviews Genetics (2010) 11:685-696.
Milbury, et al. "Enabling Clinical Cancer Genomics for Rare Mutations: COLD-PCR Magnifies Mutations Prior to Targeted

(56) References Cited

OTHER PUBLICATIONS

Amplicon Re-Sequencing". Clin Chem. Mar. 2012;58(3):580-9. doi: 10.1373/clinchem.2011.176198. Epub Dec. 21, 2011.
Miner, et al. Molecular barcodes detect redundancy and contamination in hairpin-bisulfite PCR. Nucleic Acids Res. Sep. 30, 2004;32(17):e135.
Mitchell, et al. Circulating microRNAS as stable blood-based markers for cancer detection. Proc Natl Acad Sci U S A. Jul. 29, 2008;105(30):10513-8. Epub Jul. 28, 2008.
Mitelman, F. et al. "The impact of translocations and gene fusions on cancer causation" Nature Rev. Cancer (2007) 7(4)233-245.
Mohan, et al.,Changes in colorectal carcinoma genomes under anti-EGFR therapy identified by whole-genome plasma DNA sequencing.,PLoS Genet,doi: 10.1371/journal.pgen.1004271. eCollection 2014.,Mar. 27, 2014,10(3), e1004271.
Mori, et al. Predictive utility of circulating methylated DNA in serum of melanoma patients receiving biochemotherapy. J Clin Oncol. Dec. 20, 2005;23(36):9351-8.
Morrissy, A.S. et al. "Next-generation tag sequencing for cancer gene expression profiling" Genome Research (2009) 19(10): 1825-1835.
Mortazavi, et al. Mapping and quantifying mammalian transcriptomes by RNA-Seq. Nat. Methods. 2008; 5, 621-628.
Narayan, et al. Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012.
Nawroz, et al. Microsatellite alterations in serum DNA of head and neck cancer patients. Nat Med. Sep. 1996;2(9):1035-7.
Newman, et al. An ultrasensitive method for quantitating circulating tumor DNA with broad patient coverage. Nat Med. May 2014;20(5):548-54. doi: 10.1038/nm.3519. Epub Apr. 6, 2014.
Ng, S.B., et al., "Targeted capture and massively parallel sequencing of 12 human exomes," Nature 2009, 461(7261), 272-276.
Nielsen, R. et al. "Genotype and SNP calling from next-generation sequencing data" Nature Reviews Genetics (2011)12(6):443-451.
Nord, et al. Accurate and exact CNV identification from targeted high-throughput sequence data. BMC Genomics. Apr. 12, 2011;12:184.
Notice of Allowance dated Jan. 31, 2017 for U.S. Appl. No. 14/712,754.
Notice of allowance dated Mar. 21, 2014 for U.S. Appl. No. 12/969,581.
Notice of allowance dated Jun. 15, 2017 for U.S. Appl. No. 15/076,565.
Notice of allowance dated Jun. 19, 2014 for U.S. Appl. No. 12/969,581.
Notice of allowance dated Aug. 1, 2017 for U.S. Appl. No. 15/492,659.
Notice of allowance dated Aug. 4, 2017 for U.S. Appl. No. 15/467,570.
Notice of allowance dated Aug. 22, 2014 for U.S. Appl. No. 12/969,581.
Notice of allowance dated Aug. 29, 2017 for U.S. Appl. No. 15/492,659.
Notice of allowance dated Sep. 11, 2017 for U.S. Appl. No. 15/076,565.
Notice of allowance dated Oct. 3, 2017 for U.S. Appl. No. 15/076,565.
Notice of allowance dated Oct. 25, 2017 for U.S. Appl. No. 14/861,989.
Notice of allowance dated Dec. 28, 2017 for U.S. Appl. No. 14/861,989.
Office Action dated Feb. 9, 2017 for U.S. Appl. No. 15/076,565.
Office action dated May 13, 2019 for U.S. Appl. No. 15/669,779.
Office action dated May 20, 2016 for U.S. Appl. No. 14/855,301.
Office action dated May 31, 2016 for U.S. Appl. No. 14/712,754.
Office action dated Jun. 1, 2017 for U.S. Appl. No. 15/467,570.
Office action dated Jun. 3, 2016 for U.S. Appl. No. 14/861,989.
Office action dated Jun. 12, 2017 for U.S. Appl. No. 15/492,659.
Office action dated Jul. 18, 2017 for U.S. Appl. No. 14/861,989.
Office Action dated Jul. 30, 2019 for U.S. Appl. No. 16/283,635.
Office action dated Aug. 6, 2019 for U.S. Appl. No. 14/855,301.
Office action dated Oct. 3, 2013 for U.S. Appl. No. 12/969,581.
Office Action dated Oct. 12, 2016 for U.S. Appl. No. 14/712,754.
Office action dated Oct. 20, 2017 for U.S. Appl. No. 14/425,189.
Office Action dated Nov. 21, 2016 for U.S. Appl. No. 14/855,301.
Office action dated Dec. 4, 2015 for U.S. Appl. No. 14/712,754.
Office action dated Dec. 7, 2017 for U.S. Appl. No. 14/855,301.
Office Action dated Dec. 9, 2016 for U.S. Appl. No. 14/861,989.
Office action dated Dec. 21, 2018 for U.S. Appl. No. 15/978,848.
Ogino, et al. Quantification of PCR bias caused by a single nucleotide polymorphism in SMN gene dosage analysis. J Mol Diagn. Nov. 2002;4(4):185-90.
Opposition Brief dated Aug. 7, 2018 for Japanese Opposition No. 2018-700659 to JP Patent 6275145.
Opposition Decision dated Jan. 15, 2019 for Japanese Opposition No. 2018-700659 to JP Patent 6275145.
Opposition Form and Statement to EP2893040 filed Oct. 2, 2019 by Foundation Medicine Inc.
Opposition Form and Statement to EP2893040 filed Oct. 2, 2019 by Grunecker Patent-und Rechtsanwalte PartG mbB.
Opposition Form and Statement to EP2893040 filed Oct. 2, 2019 by Personal Genome Diagnostics, Inc.
Opposition Form and Statement to EP2893040 filed Oct. 2, 2019 by Strawman Limited.
Opposition Form and Statement to EP3087204 filed Nov. 14, 2018.
Pacific Biosciences. Template Preparation and Sequencing Guide. Publication date: Oct. 14, 2014. Pacific Biosciences website http://www.pacificbiosciences.com/support/pubmap/documentation.html.
Pan, et al. Loss of heterozygosity patterns provide fingerprints for genetic heterogeneity in multistep cancer progression of tobacco smoke-induced non-small cell lung cancer. Cancer Res. Mar. 1, 2005;65(5):1664-9.
Park, et al. Discovery of common Asian copy number variants using integrated high-resolution array CGH and massively parallel DNA sequencing. Nat Genet. May 2010;42(5):400-5. doi: 10.1038/ng.555. Epub Apr. 4, 2010.
Parkinson, N.J. et al., "Preparation of high-quality next-generation sequencing libraries from picogram quantities of target DNA," Genome Res. 2012, 22(1), 125-133.
Pel, J. et al. "Duplex proximity sequencing (pro-seq): A method to improve DNA sequencing accuracy without the cost of molecular barcoding redundancy" bioRxiv (2017) https://doi.org/10.1101/163444.
Perakis, S. et al. "Advances in Circulating Tumor DNA Analysis" Adv Clin Chem (2017) pp. 1-81.
Pihlak, et al. Rapid genome sequencing with short universal tiling probes. Nature Biotechnology, 26: 676-684 (2008).
Pinkel, et al. Comparative Genomic Hybridization. Annual Review of Genomics and Human Genetics, 6: 331-354 (2005).
Pleasance, et al. A small-cell lung cancer genome with complex signatures of tobacco exposure. Nature. Jan. 14, 2010;463(7278)184-90. doi: 10.1038/nature08629. Epub Dec. 16, 2009.
Pollack, et al. Genome-wide analysis of DNA copy-number changes using cDNA microarrays. Nat Genet. Sep. 1999;23(1):41-6.
Qiu et al. DNA sequence-based "bar codes" for tracking the origins of expressed sequence tags from a maize cDNA library constructed using multiple mRNA sources. Plant Physiol. Oct. 2003;133(2):475-81.
Quail, et al. A large genome center's improvements to the Illumina sequencing system. Nat Methods. Dec. 2008;5(12):1005-10. doi: 10.1038/nmeth.1270.
Quinlan, A.R. et al., "Pyrobayes: an improved base caller for SNP discovery in pyrosequences," Nat. Methods 2008 5(2), 179-181.
Rafi, I. et al. "Cell-free fetal DNA and non-invasive prenatal diagnosis," Br. J. Gen. Pract. May 1, 2009; 59(562):e146-e148.
Rand, et al. Headloop suppression PCR and its application to selective amplification of methylated DNA sequences. Nucleic Acids Res. Aug. 9, 2005;33(14):e127.
Redon, R. et al., "Global variation in copy number in the human genome," Nature 2006 444(7118), 444-454.
Report and Recommendation in Civil Action No. 17-1623-LPS-CJB between Guardant Health, Inc. and Foundation Medicine and between Guardant Health, Inc. and Personal Genome Diagnostics, Inc., dated Oct. 11, 2019.

(56) References Cited

OTHER PUBLICATIONS

Rizzo, J.M. et al. "Key Principles and Clinical Applications of 'Next Generation' DNA Sequencing," Cancer Prev. Res., (2012) 5, 887-900.
Ryan, et al. A prospective study of circulating mutant KRAS2 in the serum of patients with colorectal neoplasia: strong prognostic indicator in postoperative follow up. Gut. Jan. 2003;52(1):101-8.
Rygaard, et al. Abnormalities in structure and expression of the retinoblastoma gene in small cell lung cancer cell lines and xenografts in nude mice. Cancer Res. Sep. 1, 1990;50(17):5312-7.
Sanger, F. et al. "DNA sequencing with chain-terminating inhibitors" PNAS (1977) 74(12):5463-5467.
Sausen, M. et al. "Integrated genomic analyses identify ARID1A and ARID1B alterations in the childhood cancer neuroblastoma", Nature Genetics 2013, 45(1), 12-17.
Schmitt et al. Supplemental Information http://www.pnas.org/content/suppl/2012/08/01/1208715109. DCSupplemental.
Schmitt, et al. Detection of ultra-rare mutations by next-generation sequencing. Proc Natl Acad Sci U S A. Sep. 4, 2012;109(36):14508-13. doi: 10.1073/pnas.1208715109. Epub Aug. 1, 2012.
Schwarzenbach, et al. A critical evaluation of loss of heterozygosity detected in tumor tissues, blood serum and bone marrow plasma from patients with breast cancer. Breast Cancer Res. 2007;9(5):R66.
Schwarzenbach, et al. Cell-free tumor DNA in blood plasma as a marker for circulating tumor cells in prostate cancer. Clin Cancer Res. Feb. 1, 2009;15(3):1032-8. doi: 10.1158/1078-0432.CCR-08-1910.
Schwarzenback, H. et al. "Cell-free nucleic acids as biomarkers in cancer patients" Nature Reviews Cancer (2011)11:426-437.
Schweiger et al., "Genome-wide massively parallel sequencing of formaldehyde fixed-paraffin embedded (FFPE) tumor tissues for copy-number- and mutation-analysis," PLoS One 2009, 4(5), e5548.
Sebat, et al. Large-Scale Copy Number Polymorphism in the Human Genome. Science, 305: 525-528 (2004).
Sehnert, A.J. et al. "Optimal Detection of Fetal Chromosomal Abnormalities by Massively Parallel DNA Sequencing of Cell-Free Fetal DNA from Maternal Blood" Clin Chem (2011) 57(7):1042-1049.
Shaw et al. Genomic analysis of circulating cell-free DNA infers breast cancer dormancy. Genome Research 22(2):220-231 (Feb. 2012).
Shaw, et al. Microsatellite alterations plasma DNA of primary breast cancer patients. Clin Cancer Res. Mar. 2000;6(3):1119-24.
Shendure, J. et al. "Next-generation DNA sequencing," Nat. Biotechnol. 2008 26(10), 1135-1145.
Shinozaki, et al. Utility of circulating B-RAF DNA mutation in serum for monitoring melanoma patients receiving Biochemotherapy. Clin Cancer Res. Apr. 1, 2007;13(7)2068-74.
Shiroguchi, et al. Digital RNA sequencing minimizes sequence-dependent bias and amplification noise with optimized single-molecule barcodes. Proc Natl Acad Sci U S A. Jan. 24, 2012;109(4):1347-52. doi: 10.1073/onas.1118018109. Epub Jan. 9, 2012.
Shoemaker, et al. Quantitative phenotypic analysis of yeast deletion mutants using a highly parallel molecular bar-coding strategy. Nature Genetics, 14: 450-456 (1996).
Simpson, et al. Copy number variant detection in inbred strains from short read sequence data. Bioinformatics. Feb. 15, 2010;26(4):565-7. doi: 10.1093/bioinformatics/btp693. Epub Dec. 18, 2009.
Smith, et al. Highly-multiplexed barcode sequencing: an efficient method for parallel analysis of pooled samples. Nucleic Acids Research, 38(13): e142 (2010).
Smith, T.F. et al. "Comparison of Biosequences" Adv App Math (1981) 2:482-489.
Sorenson, et al. Soluble normal and mutated DNA sequences from single-copy genes in human blood. Cancer Epidemiol Biomarkers Prev. Jan.-Feb. 1994;3(1):67-71.
Sparks, et al. Selective analysis of cell-free DNA in maternal blood for evaluation of fetal trisomy. Prenat Diagn. Jan. 2012;32(1):3-9. doi: 10.1002/pd.2922. Epub Jan. 6, 2012.
Stein, et al. "The case for cloud computing in genome informatics", Genome Biol. 2010; 11 (5):207. Epub May 5, 2010.
Steinman. Free DNA in serum and plasma from normal adults. J Clin Invest. Aug. 1975;56(2):512-5.
Stitziel, et al. Computational and statistical approaches to analyzing variants identified byexome sequencing. Genome Biol. Sep. 14, 2011;12(9):227. doi: 10.1186/gb-2011-12-9-227.
Stroun, M, et al, "About the possible orgin and mechanism of circulating DNA apoptosis and active DNA release", Clin Chim Acta, vol. 313, No. 1-2, pp. 139-142, (2001).
Stumm, M. et al. "Noninvasive prenatal detection of chromosomal aneuploidies using different next generation sequencing strategies and algorithms" Prenatal Diagnosis (2012) 32:569-577.
Taback, et al. Detection of tumor-specific genetic alterations in bone marrow from early-stage breast cancer patients. Cancer Res. Apr. 15, 2003;63(8):1884-7.
Tan, et al. Genome-wide comparison of DNA hydroxymethylation in mouse embryonic stem cells and neural progenitor cells by a new comparative hMeDIP-seq method. Nucleic Acids Res. Apr. 2013;41(7):e84. doi: 10.1093/nar/gkt091. Epub Feb. 13, 2013.
Taudien, et al. Haplotyping and copy number estimation of the highly polymorphic human beta-defensin locus on 8p23 by 454 amplicon sequencing. BMC Genomics. Apr. 19, 2010;11:252. doi: 10.118611471-2164-11-252.
Teer, J.K. et al. "Systematic comparison of three genomic enrichment methods for massively parallel DNA sequencing" Genome Res (2010) 20(10):1420-1431.
Tie, J. et al., "Circulating tumor DNA analysis detects minimal residual disease and predicts recurrence in patients with stage II colon cancer,"Sci. Transl. Med. 2016, 8(346):346ra92.
Tomaz, et al. Differential methylation as a cause of allele dropout at the imprinted GNAS locus. Genet Test Mol Biomarkers. Aug. 2010;14(4):455-60. doi: 10.1089/gtmb.2010.0029.
Tomlinson, et al. A genome-wide association scan of tag SNPs identifies a susceptibility variant for colorectal cancer at 8q24.21. Nat Genet. Aug. 2007;39(8):984-8. Epub Jul. 8, 2007.
Tsai, et al. Discovery of rare mutations in populations: Tilling by sequencing. Plant Physiol. Jul. 2011;156(3):1257-68. doi: 10.1104/pp. 110.169748. Epub Apr. 29, 2011.
U.S. Appl. No. 14/102,285, filed Dec. 10, 2013.
U.S. Appl. No. 61/613,413 ("Schmitt '413 provisional") (filed Mar. 20, 2012).
U.S. Appl. No. 61/625,319 ("Schmitt '319 provisional") (filed Apr. 17, 2012).
*Guardant Health* vs. *FMI* Invalidity Exhibit C-3, dated Jun. 25, 2018 (C.A. No. 17-cv-1616-LPS-CJB).
*Guardant Health* vs. *FMI* Invalidity Exhibit C-4, dated Jun. 25, 2018 (C.A. No. 17-cv-1616-LPS-CJB).
*Guardant Health* vs. *FMI* Invalidity Exhibit C-5, dated Jun. 25, 2018 (C.A. No. 17-cv-1616-LPS-CJB).
*Guardant Health* vs. *FMI* Invalidity Exhibit D-1, dated Jun. 25, 2018 (C.A. No. 17-cv-1616-LPS-CJB).
*Guardant Health* vs. *FMI* Invalidity Exhibit D-2, dated Jun. 25, 2018 (C.A. No. 17-cv-1616-LPS-CJB).
*Guardant Health* vs. *FMI* Invalidity Exhibit D-3, dated Jun. 25, 2018 (C.A. No. 17-cv-1616-LPS-CJB).
*Guardant Health* vs. *FMI* Invalidity Exhibit D-5, dated Jun. 25, 2018 (C.A. No. 17-cv-1616-LPS-CJB).
*Guardant Health* vs. *FMI* Second Amended Complaint dated Mar. 6, 2018 (C.A. No. 17-cv-1616-LPS-CJB).
*Guardant Health* vs. *FMI* Suppl Invalidity References dated Feb. 15, 2019 (C.A. No. 17-cv-1616-LPS-CJB).
*Guardant Health* vs. *FMI* Supplemental Invalidity Contentions dated Mar. 29, 2019 (C.A. No. 17-cv-1616-LPS-CJB).
*Guardant Health* vs. *PGDx* Amended Answer to Second Amended Complaint dated Apr. 30, 2019 (C.A. No. 17-cv-1623-LPS-CJB).
*Guardant Health* vs. *PGDx* Invalidity Claim Chart A, dated May 13, 2019 (C.A. No. 17-cv-1623-LPS-CJB).
*Guardant Health* vs. *PGDx* Invalidity Claim Chart B, dated May 13, 2019 (C.A. No. 17-cv-1623-LPS-CJB).
*Guardant Health* vs. *PGDx* Invalidity Claim Chart C, dated May 13, 2019 (C.A. No. 17-cv-1623-LPS-CJB).

(56) References Cited

OTHER PUBLICATIONS

*Guardant Health* vs. *PGDx* Invalidity Claim Chart D, dated May 13, 2019 (C.A. No. 17-cv-1623-LPS-CJB).
*Guardant Health* vs. *PGDx* Invalidity Claim Chart E, dated May 13, 2019 (C.A. No. 17-cv-1623-LPS-CJB).
*Guardant Health* vs. *PGDx* Invalidity Claim Chart F, dated May 13, 2019 (C.A. No. 17-cv-1623-LPS-CJB).
*Guardant Health* vs. *PGDx* Invalidity Claim Chart G, dated May 13, 2019 (C.A. No. 17-cv-1623-LPS-CJB).
*Guardant Health* vs. *PGDx* Invalidity Claim Chart H, dated May 13, 2019 (C.A. No. 17-cv-1623-LPS-CJB).
*Guardant Health* vs. *PGDx* Invalidity Claim Chart I, dated May 13, 2019 (C.A. No. 17-cv-1623-LPS-CJB).
*Guardant Health* vs. *PGDx* Invalidity Claim Chart J, dated May 13, 2019 (C.A. No. 17-cv-1623-LPS-CJB).
*Guardant Health* vs. *PGDx* Invalidity Claim Chart K, dated May 13, 2019 (C.A. No. 17-cv-1623-LPS-CJB).
*Guardant Health* vs. *PGDx* Invalidity Claim Chart L, dated May 13, 2019 (C.A. No. 17-cv-1623-LPS-CJB).
*Guardant Health* vs. *PGDx* Invalidity Contentions dated Jun. 25, 2018 (C.A. No. 17-cv-1623-LPS-CJB).
*Guardant Health* vs. *PGDx* Second Amended Complaint dated Mar. 23, 2018 (C.A. No. 17-cv-1623-LPS-CJB).
*Guardant Health* vs. *PGDx* Second Updated Invalidity Contentions dated May 13, 2019 (C.A. No. 17-cv-1623-LPS-CJB).
*Guardant Health* vs. *PGDx* Updated Invalidity Contentions dated Mar. 29, 2019 (C.A. No. 17-cv-1623-LPS-CJB).
Gundry, et al. "Direct mutation analysis by high-throughput sequencing: from gremlin to low-abundant, somatic variants" Mutat Res Jan. 3, 2012; 729(1-2):1-15. doi: 10.1016/mrfmmm.2011.10.001. Pub Oct. 12, 2011.
Gundry, et al. Direct, genome-wide assessment of DNA mutations in single cells. Nucleic Acids Res. Mar. 2012;40(5):2032-40. doi: 10.1093/nar/gkr949. Epub Nov. 15, 2011.
Hacia, et al. Determination of ancestral alleles for human single-nucleotide polymorphisms using high-density oligonucleotide arrays. Nature Genetics, 22: 164-167 (1999).
Hafner, et al. RNA-ligase-dependent biases in miRNA representation in deep-sequenced small RNA cDNA libraries, RNA Sep. 1, 2011 17(9):1697-1712.
Hall, A., Short-Read DNA Sequence Alignmnet with Custom Designed FPGA-based Hardware, Thesis 2010.
Hamady, et al. Error-correcting barcoded primers for pyrosequencing hundreds of samples in multiplex. Nat Methods. Mar. 2008;5(3):235-7. doi: 10.1038/nmeth.1184. Epub Feb. 10, 2008.
Hensel, et al. Simultaneous identification of bacterial virulence genes by negative selection. Science. Jul. 21, 1995;269(5222):400-3.
Hiatt, et al. Parallel, tag-directed assembly of locally derived short sequence reads. Nat Methods. Feb. 2010;7(2)119-22. doi: 10.1038/nmeth.1416. Epub Jan. 17, 2010.
Hiatt, et al. Single molecule molecular inversion probes for targeted, high-accuracy detection of low-frequency variation. Genome Res. May 2013;23(5):843-54. doi: 10.1101/gr.147686.112. Epub Feb. 4, 2013.
Hibi, et al. Molecular detection of genetic alterations in the serum of colorectal cancer patients. Cancer Res. Apr. 1, 1998;58(7):1405-7.
HiSeq 2000 User Guide (2010).
Holdenrieder, et al. Circulating nucleosomes and cytokeratin 19-fragments in patients with colorectal cancer during chemotherapy. Anticancer Res. May-Jun. 2005;25(3A):1795-801.
Holies, et al. A stochastic approach to count RNA molecules using DNA sequencing methods. 2003, Lecture Notes in Computer Science, vol. 2812, pp. 55-62.
Hollas, et al. A stochastic approach to count RNA molecules using DNA sequencing methods. Lecture Notes in Computer Science, 2812: 55-62 (2003).
Hollstein, M. et al. "p53 mutations in human cancers" Science (1991) 253(5015):49-53.

Hoque, et al. Detection of aberrant methylation of four genes in plasma DNA for the detection of breast cancer. J Clin Oncol. Sep. 10, 2006;24(26):4262-9. Epub Aug. 14, 2006.
Howe, et al. Retinoblastoma growth suppressor and a 300-kDa protein appear to regulate cellular DNA synthesis. Proc Natl Acad Sci U S A. Aug. 1990;87(15):5883-7.
Hug, et al. Measurement of the number of molecules of a single mRNA species in a complex mRNA preparation. J Theor Biol. Apr. 21, 2003;221(4):615-24.
Hyland, et al. The normal and tumor spectrum of copy number variation: Copy number alterations correlate with changes in gene expression in tumor transcriptome. Nov. 15, 2009. 1 page. Retreived from:http://tools.thermofisher.com/content/sfs/posters/cms_073633.pdf.
Iafrate, et al. Detection of large-scale variation in the human genome. Nat Genet. Sep. 2004;36(9):949-51. Epub Aug. 1, 2004.
Ikeguchi, et al. Detection of loss of heterozygosityat microsatellite loci in esophageal squamous-cell carcinoma. Oncology. 1999;56(2)164-8.
Illumina "Multiplexed Sequencing with Illumina Genome Analyzer System" https://www.illumina.com/Documents/products/datasheets/datasheet_sequencing_multiplex.pdf (Dec. 2008).
Illumina Preparing Samples for Paired-End Sequencing (2008).
Daser, et al. "Interrogation of genomes by molecular copy-number counting (MCC)." Nature Methods, 3(6): 447-453 (2006).
De Saizieu, et al. "Bacterial transcript imaging by hybridization of total RNA to oligonucleotide arrays." Nature Biotechnology, 16: 45-48 (1998).
Diehl et al. Circulating mutant DNA to assess tumor dynamics. Nat Med 14(9):985-990 (2008).
Diehl, et al. Detection and quantification of mutations in the plasma of patients with colorectal tumors. Proc Natl Acad Sci US A. Nov. 8, 2005;102(45):16368-73. Epub Oct. 28, 2005.
Diehl, F. et al., "Analysis of Mutations in DNA Isolated From Plasma and Stool of Colorectal Cancer Patients," Gastroenterology (2008) 135(2):489-498.
Ding, L. et al. "Clonal evolution in relapsed acute myeloid leukemia revealed by whole-genome sequencing" Nature (2012) 481(7382):506-510.
Ding, L. et al., "Analysis of next-generation genomic data in cancer: accomplishments and challenges," Hum. Mol. Genet. 2010 19(R2), R188-R196.
Duncan, D.L. et al. "Next-Generation Sequencing in the Clinical Laboratory" Diagnostic Molecular Pathology: A Guide to Applied Molecular Testing 25-33 (Coleman and Tsongalis eds., 1st ed. 2016).
Ehrich, et al. Noninvasive detection of fetal trisomy 21 by sequencing of DNA in maternal blood: a study in a clinical setting. Am J Obstet Gynecol. Mar. 2011;204(3):205.e1-11. doi: 10.1016/j.ajog. 2010.12.060. Epub Feb. 18, 2011.
Eisenmann, et al. 5q-myelodysplastic syndromes: chromosome 5q genes direct a tumor-suppression network sensing actin dynamics. Oncogene. Oct. 1, 2009;28(39):3429-41. doi: 10.1038/onc.2009.207. Epub Jul. 13, 2009.
Elshire, et al. A robust, simple genotyping-by-sequencing (GBS) approach for high diversity species. PLoS One. May 4, 2011;6(5):e19379. doi: 10.1371/journal.pone.0019379.
European search report and search opinion dated Mar. 29, 2016 for EP Application No. 13834427.0.
Extended European search report and opinion dated May 4, 2017 for EP Application No. 14874157.2.
Extended European search report and opinion dated Nov. 21, 2016 for EP Application No. 14771159.
Fan, et al. "Microfluidic digital PCR enables rapid prenatal diagnosis of fetal aneuploidy." Am Obstet Gynecol. 2009; 200:543.e1-543.e7.
Fan, et al. "Parallel Genotyping of Human SNPs Using Generic High-density Oligonucleotide Tag Arrays." Genome Research, 10: 853-860 (2000).
Fan, et al. Noninvasive diagnosis of fetal aneuploidy by shotgun sequencing DNA from maternal blood. Proc Natl Acad Sci U S A. Oct. 21, 2008;105(42):16266-71. Epub Oct. 6, 2008.

(56) References Cited

OTHER PUBLICATIONS

Fan, et al. Non-invasive prenatal measurement of the fetal genome. Nature. Jul. 19, 2012;487(7407):320-4. doi: 10.1038/nature 11251.
Fleischhacker, M. et al. "Circulating nucleic acids (CNAs) and cancer—A survey" Biochimica et Biophysica Acta (2007) 1775:181-232.
Fonatsch, C. The role of chromosome 21 in hematology and oncology. Genes Chromosomes Cancer. Jun. 2010;49(6):497-508. doi: 10.1002/gcc.20764.
Fong, S.L. et al. "Comparison of 7 Methods for Extracting Cell-Free DNA from Serum Samples of Colorectal Cancer Patients" Clinical Chem (2009) 55(3):587-598.
Forshew, T. et al. "Noninvasive Identification and Monitoring of Cancer Mutations by Targeted Deep Sequencing of Plasma DNA" Sci Transl Med (2012) 4(136) ra68.
Forster, et al. From next-generation sequencing alignments to accurate comparison and validation of single-nucleotide variants: the pibase software. Nucleic Acids Res. Jan. 7, 2013;41(1):e16. doi: 10.1093/nar/gks836. Epub Sep. 10, 2012.
Fournie, et al. Plasma DNA as a marker of cancerous cell death. Investigations in patients suffering from lung cancer and in nude mice bearing human tumours. Cancer Lett. May 8, 1995;91(2):221-7.
Freeman, et al. Profiling the T-cell receptor beta-chain repertoire by massively parallel sequencing. Genome Res. Oct. 2009;19(10):1817-24. doi: 10.1101/gr.092924.109. Epub Jun. 18, 2009.
Fu, et al. Counting individual DNA molecules by the stochastic attachment of diverse labels. Proc Natl Acad Sci U S A. May 31, 2011;108(22):9026-31. Epub May 11, 2011.
Fujiwara, et al. Identification of epigenetic aberrant promoter methylation in serum DNA is useful for early detection of lung cancer Clin Cancer Res. Feb. 1, 2005;11(3):1219-25.
Fujiwara, et al. Plasma DNA microsatellites as tumor-specific markers and indicators of tumor progression in melanoma patients. Cancer Res. Apr. 1, 1999;59(7):1567-71.
Genome Analyzer IIx Systems Specification Sheet (2009).
Gerry, et al. Universal DNA microarray method for multiplex detection of low abundance point mutations. Journal of Molecular Biology, 292(2): 251-262 (1999).
Gillespie. Exact stochastic simulation of coupled chemical reactions. The Journal of Physical Chemistry, 81(25): 2340-2361 (1977).
Gordian, et al. Serum free circulating DNA is a useful biomarker to distinguish benign versus malignant prostate disease. Cancer Epidemiol Biomarkers Prev. Aug. 2010;19(8):1984-91. doi: 10.1158/1055-9965.EPI-10-0287. Epub Jul. 20, 2010.
Gordon, D.J. et al., "Causes and consequences of aneuploidy in cancer," Nat. Rev. Genet. 2012 13(3), 189-203.
Gormally, et al. Amount of DNA in plasma and cancer risk: a prospective study. Int J Cancer. Sep. 20, 2004;111(5):746-9.
Grant, et al. SNP genotyping on a genome-wide amplified DOP-PCR template. Nucleic Acids Res. Nov. 15, 2002;30(22):e25.
Gregory et al. "Targeted Single Molecule Mutation Detection with Massively Parallel Sequencing" Nucleic Acids Research (2015) 44(3):2-11.
Grutzmann, et al. Sensitive detection of colorectal cancer in peripheral blood by septin 9 DNA methylation assay. PLoS One. 2008;3(11):e3759. doi: 10.1371/journal.pone.0003759. Epub Nov. 19, 2008.
*Guardant Health* vs. *FMI* 1st Amended Answer to Second Amended Complaint dated May 6, 2019 (C.A. No. 17-cv-1616-LPS-CJB).
*Guardant Health* vs. *FMI* Invalidity Contentions dated Jun. 25, 2018 (C.A. No. 17-cv-1616-LPS-CJB).
*Guardant Health* vs. *FMI* Invalidity Exhibit A-1, dated Jun. 25, 2018 (C.A. No. 17-cv-1616-LPS-CJB).
*Guardant Health* vs. *FMI* Invalidity Exhibit A-2, dated Jun. 25, 2018 (C.A. No. 17-cv-1616-LPS-CJB).
*Guardant Health* vs. *FMI* Invalidity Exhibit A-3, dated Jun. 25, 2018 (C.A. No. 17-cv-1616-LPS-CJB).
*Guardant Health* vs. *FMI* Invalidity Exhibit A-8, dated Jun. 25, 2018 (C.A. No. 17-cv-1616-LPS-CJB).
*Guardant Health* vs. *FMI* Invalidity Exhibit B-1, dated Jun. 25, 2018 (C.A. No. 17-cv-1616-LPS-CJB).
*Guardant Health* vs. *FMI* Invalidity Exhibit B-2, dated Jun. 25, 2018 (C.A. No. 17-cv-1616-LPS-CJB).
*Guardant Health* vs. *FMI* Invalidity Exhibit B-3, dated Jun. 25, 2018 (C.A. No. 17-cv-1616-LPS-CJB).
*Guardant Health* vs. *FMI* Invalidity Exhibit B-7, dated Jun. 25, 2018 (C.A. No. 17-cv-1616-LPS-CJB).
*Guardant Health* vs. *FMI* Invalidity Exhibit C-1, dated Jun. 25, 2018 (C.A. No. 17-cv-1616-LPS-CJB).
*Guardant Health* vs. *FMI* Invalidity Exhibit C-11, dated Jun. 25, 2018 (C.A. No. 17-cv-1616-LPS-CJB).
*Guardant Health* vs. *FMI* Invalidity Exhibit C-2, dated Jun. 25, 2018 (C.A. No. 17-cv-1616-LPS-CJB).
UCSC Genome Bioinformatics. About the UCSC Genome Bioinformatics Site. http://genome.ucsc.edu/index.html. Accessed on May 26, 2015. 2 pgs.
Umetani et al. Prediction of Breast Tumor Progression by Integrity of Free Circulating DNA in Serum. Journal of Clinical Oncology 24(26):4270-4276 (Sep. 10, 2006).
U.S. Appl. No. 61/384,001, filed Sep. 17, 2010.
U.S. Appl. No. 61/432,119, filed Jan. 12, 2011.
Utting, et al. Microsatellite analysis of free tumor DNA in urine, serum, and plasma of patients: a minimally invasive method for the detection of bladder cancer. Clin Cancer Res. Jan. 2002;8(1):35-40.
Van Houten, et al. Mutated p53 as a molecular marker for the diagnosis of head and neck cancer. J Pathol. Dec. 2002;198(4):476-86.
Van Orsouw, N. et al. "Complexity Reduction of Polymorphic Sequences (CRoPSTM): A Novel Approach for Large-Scale Polymorphism Discovery in Complex Genomes" PLoS One (2007) 11(e1172):1-10.
Vasyukhin, V. et al., "K-Ras Point Mutations in the Blood Plasma DNA of Patients with Colorectal Tumors" Challenges of Modern Medicine, 141-150 (Verna and Shamoo eds, 1994).
Velculescu, et al. Characterization of the Yeast Transcriptome. Cell, 88: 243-251 (1997).
Velculescu, et al. Serial Analysis of Gene Expression. Science, 270: 484-487 (1995).
Vogelstein, et al. Digital PCR. Proc. Natl. Acad. Sci., 96(16): 9236-9241(1999).
Wagle, N. et al., "High-throughput Detection of actionable Genomic alterations in clinical tumor samples by targeted, Massively Parallel sequencing," Cancer Discov. 2012, (2)1:82-93.
Walker, et al. Isothermal in vitro amplification of DNA by a restriction enzyme/DNA polymerase system. Proc Natl Acad Sci U S A. Jan. 1, 1992;89(1):392-6.
Walsh, et al. Detection of inherited mutations for breast and ovarian cancer using genomic capture and massively parallel sequencing. Proc Natl Acad Sci U S A. Jul. 13, 2010;107(28):12629-33. doi: 10.1073/pnas.1007983107. Epub Jun. 28, 2010.
Wang, et al. iCLIP predicts the dual splicing effects of TIA-RNA interactions, Oct. 2010, PLoS Biol, 8(10):e1000530.
Wang, et al. Molecular detection of APC, K-ras, and p53 mutations in the serum of colorectal cancer patients as circulating biomarkers. World J Surg. Jul. 2004;28(7):721-6. Epub Jun. 8, 2004.
Wang, et al. RNA-Seq: a revolutionary tool for transcriptomics. Nature Reviews Genetics, 10: 57-63 (2009).
Wang, T.L. et al. "Digital Karyotyping" PNAS (2002) 99(25):16156-16161.
Wang, Y. et al., "Detection of somatic mutations and HPV in the saliva and plasma of patients with head and neck squamous cell carcinomas," Sci. Transl. Med. 2015, 7(293):293ra104.
Wang, Y. et al., "Detection of tumor-derived DNA in cerebrospinal fluid of patients with primary tumors of the brain and spinal cord," Proc. Natl. Acad. Sci. USA 2015, 112(31), 9704-9709.
Wang, Y. et al., "Diagnostic potential of tumor DNA from ovarian cyst fluid," eLife 2016, 5:e15175.
Weber, et al. A real-time polymerase chain reaction assay for quantification of allele ratios and correction of amplification bias. Anal Biochem. Sep. 15, 2003;320(2):252-8.

(56) References Cited

OTHER PUBLICATIONS

Wheeler, D.A. et al., "The complete genome of an individual by massively parallel DNA sequencing," Nature 2008, 452(7189),872-876.
Williford, A. et al., "Gene Fusion," eLS 2013, 1-8.
Wittes, et al. Searching for Evidence of Altered Gene Expression: a Comment on Statistical Analysis of Microarray Data. Journal of the National Cancer Institute, 91(5): 400-401 (1999).
Wodicka, et al. Genome-wide expression monitoring in *Saccharomyces cerevisiae*. Nature Biotechnology, 15: 1359-1367 (1997).
Wojdacs, et al. Primer design versus PCR bias in methylation independent PCR amplifications. Epigenetics. May 16, 2009;4(4):231-4. Epub May 14, 2009.
Wood, et al. The genomic landscapes of human breast and colorectal cancers. Science. Nov. 16, 2007;318 (5853)1108-13. Epub Oct. 11, 2007.
Wood, et al. Using next-generation sequencing for high resolution multiplex analysis of copy number variation from nanogram quantities of DNA from formalin-fixed paraffin-embedded specimens. Nucleic Acids Res. Aug. 2010;38(14): e151. doi: 10.1093/nar/gkq510. Epub Jun. 4, 2010.
Xi, et al. Copy number variation detection in whole-genome sequencing data using the Bayesian information criterion. Proc Natl Acad Sci U S A. Nov. 15, 2011;108(46):E1128-36. doi: 10.1073/pnas.1110574108. Epub Nov. 7, 2011.
Yandell, et al. A probabilistic disease-gene finder for personal genomes. Genome Res. Sep. 2011;21(9):1529-42. doi: 10.1101/gr.123158.111. Epub Jun. 23, 2011.
Yang, et al., EGFR gene copy number as a predictive biomarker for the treatment of metastatic colorectal cancer with anti-EGFR monoclonal antibodies: a meta-analysis.,J Hematol Oncol, Aug. 16, 2012,5:52,1-9.
Yang. Simple binary segmentation frameworks for identifying variation in DNA copy number. BMC Bioinformatics. Oct. 30, 2012;13:277. doi: 10.1186/1471-2105-13-277.
Ye, et al. Fluorescent microsphere-based readout technology for multiplexed human single nucleotide polymorphism analysis and bacterial identification. Human Mutation, 17(4): 305-316 (2001).
Yoon, et al. Sensitive and accurate detection of copy numbers variants using read depth of coverage. Genome Res. Sep. 2009;19(9):1586-92. doi: 10.1101/gr.092981.109. Epub Aug. 5, 2009.
Zhang, et al. "Comprehensive One-Step Molecular Analysis of Mitochondrial Genome by Massively Parallel Sequencing" Clinical Chem (2012) 58(9):1322-1331.
Zhang et al. The impact of next-generation sequencing on genomics. J Genet Genomics. Mar. 20, 2011;38(3):95-109. doi:10.1016/.jgg.2011.02.003. Epub Mar. 15, 2011.
Zhao, et al. Homozygous Deletions and Chromosome Amplifications in Human Lung Carcinomas Revealed by Single Nucleotide Polymorphism Array Analysis. Cancer Research, 65: 5561-5570 (2005).
Zhou, et al. Counting alleles reveals a connection between chromosome 18q loss and vascularinvasion. Nature Biotechnology, 19: 78-81 (2001).
Clark, T.A. et al. "Analytical Validation of a Hybrid Capture Based Next-Generation Sequencing Clinical Assay for Genomic Profiling of Cell-Free Circulating Tumor DNA," J. Mol. Diagnostics (2018) 20(5):686-702.
Kamps-Hughes, N. et al. "ERASE-Seq: Leveraging replicate measurements to enhance ultralow frequency variant detection in NGS data"PLoS One (2018).
Lennon, N.J. et al. "Technological considerations for genome-guided diagnosis and management of cancer" Gen Med (2016) 8:112.
Mishra, S. et al. "Different Facets of Copy Number Changes: Permanent, Transient, and Adaptive" Mol Cell Biol (2016) 36(7):1050-1063.
Moench, S. Genomic Profiling Using Guardant 360 Cell-Free DNA-Based Assay vs Tumor-Based Genotyping Assays in Advanced NSCLC, Cancer Therapy Advisor (Feb. 28, 2019), https://www.cancertherapyadvisor.com/home/news/conferencecoverage/american-association-for-cancer-research-aacr/aacr-2019/genomic-profiling-using-guardant-360-cell-free-dna-based assay-vs-tumor-based-genotyping-assays-in-advanced-nsclc/ (lastaccessed Nov. 30, 2019).
Newman, A. et al. "Integrated digital error suppression for improved detection of circulating tumor DNA" Nature Biotech (2016) 34(5):547-555.
Odegaard, J.I. et al. "Validation of a Plasma-Based Comprehensive Cancer Genotyping Assay Utilizing Orthogonal Tissue- and Plasma-Based Methodologies" Clin Canc Res (2018) 24(15):3539-3549.
Ou, Shi et al. "Liquid Biopsy to Identify Actionable Genomic Alterations" Am Soc Clin Onc (2018) 978.
Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.
Phallen, J. et al. "Direct detection of early-stage cancers using circulating tumor DNA" Sci Trans Med (2017) vol. 9, Issue 403, eaan2415DOI: 10.1126/scitranslmed.aan2415.
Sathirapongsasuti, J.F. et al. "Exome sequencing-based copy-number variation and loss of heterozygosity detection: ExomeCNV" BioInformatics (2011) 27(19):2648-2654.
Shiroguchi, et al. Digital RNA sequencing minimizes sequence-dependent bias and amplification noise with optimized single-molecule barcodes. Proc Natl Acad Sci U S A. 2012 Supplemental Information (8 pages).
Trapnell, C. et al. "How to map billions of short reads onto genomes" Nature Biotech (2009) 27(5):455-457.
Van Loo, P. et al. "Allele-specific copy number analysis of tumors" PNAS (2010) 107(39):16910-16915.
Wang, T.T. et al. "High efficiency error suppression for accurate detection of low-frequency variants" NAR (2019) 47(15):e87.
Guardant Health, Inc. Response to Notices of Opposition in EP2893040 filed May 29, 2020.
IPR2019-00634, Final Written Decision of U.S. Pat. No. 9,840,743, dated Aug. 18, 2020.
IPR2019-00652, Final Written Decision of U.S. Pat. No. 9,834,822, dated Aug. 18, 2020.
EPO Preliminary Opinion, dated Aug. 25, 2020, in EP2893040.
Lo, Dennis Interview with Professor Dennis Lo, Qiagen News (2002).
Opponents Reply dated Aug. 20, 2020 to Proprietor's Observation in EP2893040.
Opposition Form and Statement to EP3470533 filed Aug. 6, 2020 by Foundation Medicine Inc.
U.S. Appl. No. 61/625,623, filed Apr. 17, 2012.
Jiang et al. "Basics in Bioinformatics Lecture Notes of the Graduate Summer School on Bioinformatics of China" Springer Heidelburg New York Dordrecht London (2013).
Opposition Form and Statement to EP3378952 filed Nov. 4, 2020 by Dirk Buhler.
Opposition Form and Statement to EP3378952 filed Nov. 5, 2020 by Foundation Medicine Inc.
Opposition Form and Statement to EP3378952 filed Nov. 5, 2020 by Grunecker.

\* cited by examiner

METHODS AND SYSTEMS FOR DETECTING GENETIC VARIANTS

CROSS-REFERENCE

This application is a continuation of U.S. application Ser. No. 16/672,267, filed Nov. 1, 2019, which is a continuation of U.S. application Ser. No. 16/601,168, filed Oct. 14, 2019, which is a continuation of U.S. application Ser. No. 15/892,178, filed Feb. 8, 2018, which is a continuation of U.S. application Ser. No. 14/861,989, filed Sep. 22, 2015 (now U.S. Pat. No. 9,920,366, issued Mar. 20, 2018), which is a continuation application of International Application No. PCT/US2014/072383, filed Dec. 24, 2014, which application claims the benefit under 35 U.S.C. § 119(e) of U.S. Provisional Application No. 61/921,456, filed Dec. 28, 2013, and U.S. Provisional Application No. 61/948,509, filed Mar. 5, 2014, each of which is entirely incorporated herein by reference.

BACKGROUND

The detection and quantification of polynucleotides is important for molecular biology and medical applications, such as diagnostics. Genetic testing is particularly useful for a number of diagnostic methods. For example, disorders that are caused by rare genetic alterations (e.g., sequence variants) or changes in epigenetic markers, such as cancer and partial or complete aneuploidy, may be detected or more accurately characterized with DNA sequence information.

Early detection and monitoring of genetic diseases, such as cancer, is often useful and needed in the successful treatment or management of the disease. One approach may include the monitoring of a sample derived from cell-free nucleic acids, a population of polynucleotides that can be found in different types of bodily fluids. In some cases, disease may be characterized or detected based on detection of genetic aberrations, such as copy number variation and/or sequence variation of one or more nucleic acid sequences, or the development of other certain rare genetic alterations. Cell-free DNA (cfDNA) may contain genetic aberrations associated with a particular disease. With improvements in sequencing and techniques to manipulate nucleic acids, there is a need in the art for improved methods and systems for using cell-free DNA to detect and monitor disease.

In particular, many methods have been developed for accurate copy number variation estimation, especially for heterogeneous genomic samples, such as tumor-derived gDNA or for cfDNA for many applications (e.g., prenatal, transplant, immune, metagenomics or cancer diagnostics). Most of these methods include sample preparation whereby the original nucleic acids are converted into a sequenceable library, followed by massively parallel sequencing, and finally bioinformatics to estimate copy number variation at one or more loci.

SUMMARY

Although many of these methods are able to reduce or combat the errors introduced by the sample preparation and sequencing processes for all molecules that are converted and sequenced, these methods are not able to infer the counts of molecules that were converted but not sequenced. Since this count of converted by unsequenced molecules can be highly variable from genomic region to region, these counts can dramatically and adversely affect the sensitivity that can be achieved.

To address this issue, input double-stranded deoxyribonucleic acid (DNA) can be converted by a process that tags both halves of the individual double-stranded molecule, in some cases differently. This can be performed using a variety of techniques, including ligation of hairpin, bubble, or forked adapters or other adaptors having double-stranded and single stranded segments (the unhybridized portion of a bubble, forked or hairpin adapter are deemed single-stranded herein). If tagged correctly, each original Watson and Crick (i.e., strand) side of the input double-stranded DNA molecule can be differently tagged and identified by the sequencer and subsequent bioinformatics. For all molecules in a particular region, counts of molecules where both Watson and Crick sides were recovered ("Pairs") versus those where only one half was recovered ("Singlets") can be recorded. The number of unseen molecules can be estimated based on the number of Pairs and Singlets detected.

An aspect of the present disclosure provides a method for detecting and/or quantifying rare deoxyribonucleic acid (DNA) in a heterogeneous population of original DNA fragments, comprising tagging the original DNA fragments in a single reaction using a library of a plurality of different tags such that greater than 30% of the fragments are tagged at both ends, wherein each of the tags comprises a molecular barcode. The single reaction can be in a single reaction vessel. Greater than 50% of the fragments can be tagged at both ends. The plurality of different tags can be no more than any of 100, 500, 1000, 10,000 or 100,000 different tags.

Another aspect provides a set of library adaptors that can be used to tag the molecules of interest (e.g., by ligation, hybridization, etc.). The set of library adaptors can comprise plurality of polynucleotide molecules with molecular barcodes, wherein the plurality of polynucleotide molecules are less than or equal to 80 nucleotide bases in length, wherein the molecular barcodes are at least 4 nucleotide bases in length, and wherein (a) the molecular barcodes are different from one another and have an edit distance of at least 1 between one another; (b) the molecular barcodes are located at least one nucleotide base away from a terminal end of their respective polynucleotide molecules; (c) optionally, at least one terminal base is identical in all of the polynucleotide molecules; and (d) none of the polynucleotide molecules contains a complete sequencer motif.

In some embodiments, the library adaptors (or adapters) are identical to one another but for the molecular barcodes. In some embodiments, each of the plurality of library adaptors comprises at least one double-stranded portion and at least one single-stranded portion (e.g., a non-complementary portion or an overhang). In some embodiments, the double-stranded portion has a molecular barcode selected from a collection of different molecular barcodes. In some embodiments, the given molecular barcode is a randomer. In some embodiments, each of the library adaptors further comprises a strand-identification barcode on the at least one single-stranded portion. In some embodiments, the strand-identification barcode includes at least 4 nucleotide bases. In some embodiments, the single-stranded portion has a partial sequencer motif. In some embodiments, the library adaptors do not include a complete sequencer motif.

In some embodiments, none of the library adaptors contains a sequence for hybridizing to a flow cell or forming a hairpin for sequencing.

In some embodiments, all of the library adaptors have a terminal end with nucleotide(s) that are the same. In some embodiments, the identical terminal nucleotide(s) are over two or more nucleotide bases in length.

In some embodiments, each of the library adapters is Y-shaped, bubble shaped or hairpin shaped. In some embodiments, none of the library adapters contains a sample identification motif. In some embodiments, each of the library adapters comprises a sequence that is selectively hybridizable to a universal primer. In some embodiments, each of the library adapters comprises a molecular barcode that is at least 5, 6, 7, 8, 9 and 10 nucleotide bases in length. In some embodiments, each of the library adapters is from 10 nucleotide bases to 80 in length, or 30 to 70 nucleotide bases in length, or 40 to 60 nucleotide bases in length. In some embodiments, at least 1, 2, 3, or 4 terminal bases are identical in all of the library adaptors. In some embodiments, at least 4 terminal bases are identical in all of the library adaptors.

In some embodiments, the edit distance of the molecular barcodes of the library adapters is a Hamming distance. In some embodiments, the edit distance is at least 1, 2, 3, 4 or 5. In some embodiments, the edit distance is with respect to individual bases of the plurality of polynucleotide molecules. In some embodiments, the molecular barcodes are located at least 10 nucleotide base away from a terminal end of an adapter. In some embodiments, the plurality of library adapters includes at least 2, 4, 6, 8, 10, 20, 30, 40 or 50 different molecular barcodes, or from 2-100, 4-80, 6-60 or 8-40 different molecular barcodes. In any of the embodiments herein, there are more polynucleotides (e.g., cfDNA fragments) to be tagged than there are different molecular barcodes such that the tagging is not unique.

In some embodiments, the terminal end of an adaptor is configured for ligation (e.g., to a target nucleic acid molecule). In some embodiments, the terminal end of an adaptor is a blunt end.

In some embodiments, the adaptors are purified and isolated. In some embodiments, the library comprises one or more non-naturally occurring bases.

In some embodiments, the polynucleotide molecules comprise a primer sequence positioned 5' with respect to the molecular barcodes.

In some embodiments, the set of library adaptors consists essentially of the plurality of polynucleotide molecules.

In another aspect, a method comprises (a) tagging a collection of polynucleotides with a plurality of polynucleotide molecules from a library of adaptors to create a collection of tagged polynucleotides; and (b) amplifying the collection of tagged polynucleotides in the presence of sequencing adaptors, wherein the sequencing adaptors have primers with nucleotide sequences that are selectively hybridizable to complementary sequences in the plurality of polynucleotide molecules. The library of adaptors may be as described above or elsewhere herein. In some embodiments, each of the sequencer adaptors further comprises an index tag, which can be a sample identification motif.

Another aspect, provides a method for detecting and/or quantifying rare DNA in a heterogeneous population of original DNA fragments, wherein the rare DNA has a concentration that is less than 1%, the method comprising (a) tagging the original DNA fragments in a single reaction such that greater than 30% of the original DNA fragments are tagged at both ends with library adaptors that comprise molecular barcodes, thereby providing tagged DNA fragments; (b) performing high-fidelity amplification on the tagged DNA fragments; (c) optionally, selectively enriching a subset of the tagged DNA fragments; (d) sequencing one or both strands of the tagged, amplified and optionally selectively enriched DNA fragments to obtain sequence reads comprising nucleotide sequences of the molecular barcodes and at least a portion of the original DNA fragments; (e) from the sequence reads, determining consensus reads that are representative of single-strands of the original DNA fragments; and (f) quantifying the consensus reads to detect and/or quantify the rare DNA at a specificity that is greater than 99.9%.

In some embodiments, (e) comprises comparing sequence reads having the same or similar molecular barcodes and the same or similar end of fragment sequences. In some embodiments, the comparing further comprises performing a phylogentic analysis on the sequence reads having the same or similar molecular barcodes. In some embodiments, the molecular barcodes include a barcode having an edit distance of up to 3. In some embodiments, the end of fragment sequence includes fragment sequences having an edit distance of up to 3.

In some embodiments, the method further comprises sorting sequence reads into paired reads and unpaired reads, and quantifying a number of paired reads and unpaired reads that map to each of one or more genetic loci.

In some embodiments, the tagging occurs by having an excess amount of library adaptors as compared to original DNA fragments. In some embodiments, n the excess is at least a 5-fold excess. In some embodiments, the tagging comprises using a ligase. In some embodiments, the tagging comprises attachment to blunt ends.

In some embodiments, the method further comprises binning the sequence reads according to the molecular barcodes and sequence information from at least one end of each of the original DNA fragments to create bins of single stranded reads. In some embodiments, the method further comprises, in each bin, determining a sequence of a given original DNA fragment among the original DNA fragments by analyzing sequence reads. In some embodiments, the method further comprises detecting and/or quantifying the rare DNA by comparing a number of times each base occurs at each position of a genome represented by the tagged, amplified, and optionally enriched DNA fragments.

In some embodiments, the library adaptors do not contain complete sequencer motifs. In some embodiments, the method further comprises selectively enriching a subset of the tagged DNA fragments. In some embodiments, the method further comprises, after enriching, amplifying the enriched tagged DNA fragments in the presence of sequencing adaptors comprising primers. In some embodiments, (a) provides tagged DNA fragments having from 2 to 1000 different combinations of molecular barcodes.

In some embodiments, the DNA fragments are tagged with polynucleotide molecules from a library of adaptors as described above or elsewhere herein.

In another aspect, a method for processing and/or analyzing a nucleic acid sample of a subject comprises (a) exposing polynucleotide fragments from the nucleic acid sample to a set of library adaptors to generate tagged polynucleotide fragments; and (b) subjecting the tagged polynucleotide fragments to nucleic acid amplification reactions under conditions that yield amplified polynucleotide fragments as amplification products of the tagged polynucleotide fragments. The set of library adaptors comprises a plurality of polynucleotide molecules with molecular barcodes, wherein the plurality of polynucleotide molecules are less than or equal to 80 nucleotide bases in length, wherein the molecular barcodes are at least 4 nucleotide bases in length, and wherein (1) the molecular barcodes are different from one another and have an edit distance of at least 1 between one another; (2) the molecular barcodes are located at least one nucleotide base away from a terminal end of their respective polynucleotide molecules; (3) optionally, at least one terminal base is identical in all of the polynucleotide molecules; and (4) none of the polynucleotide molecules contains a complete sequencer motif.

In some embodiments, the method further comprises determining nucleotide sequences of the amplified tagged polynucleotide fragments. In some embodiments, the nucleotide sequences of the amplified tagged polynucleotide fragments are determined without polymerase chain reaction (PCR). In some embodiments, the method further comprises analyzing the nucleotide sequences with a programmed computer processor to identify one or more genetic variants in the nucleotide sample of the subject. In some embodiments, the one or more genetic variants are selected from the group consisting of base change(s), insertion(s), repeat(s), deletion(s), copy number variation(s) and transversion(s). In some embodiments, the one or more genetic variants include one or more tumor associated genetic alterations.

In some embodiments, the subject has or is suspected of having a disease. In some embodiments, the disease is cancer. In some embodiments, the method further comprises collecting the nucleic acid sample from the subject. In some embodiments, the nucleic acid sample is collected from a location selected from the group consisting of blood, plasma, serum, urine, saliva, mucosal excretions, sputum, stool, cerebral spinal fluid and tears of the subject. In some embodiments, the nucleic acid sample is a cell-free nucleic acid sample. In some embodiments, the nucleic acid sample is collected from no more than 100 nanograms (ng) of double-stranded polynucleotide molecules of the subject.

In some embodiments, the polynucleotide fragments comprise double-stranded polynucleotide molecules. In some embodiments, in (a), the plurality of polynucleotide molecules couple to the polynucleotide fragments via blunt end ligation, sticky end ligation, molecular inversion probes, PCR, ligation-based PCR, multiplex PCR, single stranded ligation, and single stranded circularization. In some embodiments, exposing the polynucleotide fragments of the nucleic acid sample to the plurality of polynucleotide molecules yields the tagged polynucleotide fragments with a conversion efficiency of at least 10%. In some embodiments, any of at least 5%, 6%, 7%, 8%, 9%, 10%, 20%, or 25% of the tagged polynucleotide fragments share a common polynucleotide molecule or sequence. In some embodiments, the method further comprises generating the polynucleotide fragments from the nucleic acid sample.

In some embodiments, the subjecting comprises amplifying the tagged polynucleotide fragments from sequences corresponding to genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1.

In another aspect, a method comprises (a) generating a plurality of sequence reads from a plurality of polynucleotide molecules, wherein the plurality of polynucleotide molecules cover genomic loci of a target genome, wherein the genomic loci correspond to a plurality of genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1; (b) grouping with a computer processor the plurality of sequence reads into families, wherein each family comprises sequence reads from one of the template polynucleotides; (c) for each of the families, merging sequence reads to generate a consensus sequence; (d) calling the consensus sequence at a given genomic locus among the genomic loci; and (e) detecting at the given genomic locus any of genetic variants among the calls, frequency of a genetic alteration among the calls, total number of calls, and total number of alterations among the calls.

In some embodiments, each family comprises sequence reads from only one of the template polynucleotides. In some embodiments, the given genomic locus comprises at least one nucleic acid base. In some embodiments, the given genomic locus comprises a plurality of nucleic acid bases. In some embodiments, the calling comprises calling at least one nucleic acid base at the given genomic locus. In some embodiments, the calling comprises calling a plurality of nucleic acid bases at the given genomic locus. In some embodiments, the calling comprises any one of phylogenetic analysis, voting, weighing, assigning a probability to each read at the locus in a family and calling the base with the highest probability.

In some embodiments, the method further comprises performing (d)-(e) at an additional genomic locus among the genomic loci. In some embodiments, the method further comprises determining a variation in copy number at one of the given genomic locus and additional genomic locus based on counts at the given genomic locus and additional genomic locus.

In some embodiments, the grouping comprises classifying the plurality of sequence reads into families by identifying (i) different molecular barcodes coupled to the plurality of polynucleotide molecules and (ii) similarities between the plurality of sequence reads, wherein each family includes a plurality of nucleic acid sequences that are associated with a different combination of molecular barcodes and similar or identical sequence reads. Different molecular barcodes have different sequences.

In some embodiments, the consensus sequence is generated by evaluating a quantitative measure or a statistical significance level for each of the sequence reads. In some embodiments, the quantitative measure comprises use of a binomial distribution, exponential distribution, beta distribution, or empirical distribution. In some embodiments, the method further comprises mapping the consensus sequence to the target genome. In some embodiments, the plurality of genes includes at least 2, 3, 4, 5, 6, 7, 8, 9, 10, 20, 30, 40, 50 or all of the plurality of genes selected from the group.

Another aspect of the present disclosure provides a method, comprising (a) providing template polynucleotide molecules and a set of library adaptors in a single reaction vessel, wherein the library adaptors are polynucleotide molecules that have different molecular barcodes (e.g., from 2 to 1,000 different molecular barcodes), and wherein none of the library adaptors contains a complete sequencer motif; (b) in the single reaction vessel, coupling the library adaptors to the template polynucleotide molecules at an efficiency of at least 10%, thereby tagging each template polynucleotide with a tagging combination that is among a plurality of different tagging combinations (e.g., 4 to 1,000,000 different tagging combinations), to produce tagged polynucleotide molecules; (c) subjecting the tagged polynucleotide molecules to an amplification reaction under conditions that yield amplified polynucleotide molecules as amplification products of the tagged polynucleotide molecules; and (d) sequencing the amplified polynucleotide molecules.

In some embodiments, the template polynucleotide molecules are blunt ended or sticky-ended. In some embodiments, the library adaptors are identical but for the molecular barcodes. In some embodiments, each of the library adaptors has a double stranded portion and at least one single-stranded portion. In some embodiments, the double-stranded portion has a molecular barcode among the molecular barcodes. In some embodiments, each of the library adaptors further comprises a strand-identification barcode on the at least one single-stranded portion. In some embodiments, the single-stranded portion has a partial sequencer motif. In some embodiments, the library adaptors have a sequence of terminal nucleotides that are the same. In some embodiments, the template polynucleotide molecules are double-stranded. In some embodiments, the library adaptors couple to both ends of the template polynucleotide molecules.

In some embodiments, subjecting the tagged polynucleotide molecules to the amplification reaction comprises non-specifically amplifying the tagged polynucleotide molecules.

In some embodiments, the amplification reaction comprises use of a priming site to amplify each of the tagged polynucleotide molecules. In some embodiments, the priming site is a primer. In some embodiments, the primer is a universal primer. In some embodiments, the priming site is a nick.

In some embodiments, the method further comprises, prior to (e), (i) separating polynucleotide molecules comprising one or more given sequences from the amplified polynucleotide molecules, to produce enriched polynucleotide molecules; and (ii) amplifying the enriched polynucleotide molecules with sequencing adaptors.

In some embodiments, the efficiency is at least 30%, 40%, or 50%. In some embodiments, the method further comprises identifying genetic variants upon sequencing the amplified polynucleotide molecules. In some embodiments, the sequencing comprises (i) subjecting the amplified polynucleotide molecules to an additional amplification reaction under conditions that yield additional amplified polynucleotide molecules as amplification products of the amplified polynucleotide molecules, and (ii) sequencing the additional amplified polynucleotide molecules. In some embodiments, the additional amplification is performed in the presence of sequencing adaptors.

In some embodiments, (b) and (c) are performed without aliquoting the tagged polynucleotide molecules. In some embodiments, the tagging is non-unique tagging.

Another aspect, provides a system for analyzing a target nucleic acid molecule of a subject, comprising a communication interface that receives nucleic acid sequence reads for a plurality of polynucleotide molecules that cover genomic loci of a target genome; computer memory that stores the nucleic acid sequence reads for the plurality of polynucleotide molecules received by the communication interface; and a computer processor operatively coupled to the communication interface and the memory and programmed to (i) group the plurality of sequence reads into families, wherein each family comprises sequence reads from one of the template polynucleotides, (ii) for each of the families, merge sequence reads to generate a consensus sequence, (iii) call the consensus sequence at a given genomic locus among the genomic loci, and (iv) detect at the given genomic locus any of genetic variants among the calls, frequency of a genetic alteration among the calls, total number of calls; and total number of alterations among the calls, wherein the genomic loci correspond to a plurality of genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1.

In another aspect, a set of oligonucleotide molecules that selectively hybridize to at least 5 genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1.

In some embodiments, the oligonucleotide molecules are from 10-200 bases in length. In some embodiments, the oligonucleotide molecules selectively hybridize to exon regions of the at least 5 genes. In some embodiments, the oligonucleotide molecules selectively hybridize to at least 30 exons in the at least 5 genes. In some embodiments, multiple oligonucleotide molecules selectively hybridize to each of the at least 30 exons. In some embodiments, the oligonucleotide molecules that hybridize to each exon have sequences that overlap with at least 1 other oligonucleotide molecule.

In another aspect, a kit comprises a first container containing a plurality of library adaptors each having a different molecular barcode; and a second container containing a plurality of sequencing adaptors, each sequencing adaptor comprising at least a portion of a sequencer motif and optionally a sample barcode. The library adaptors can be as described above or elsewhere herein.

In some embodiments, the sequencing adaptor comprises the sample barcode. In some embodiments, the library adaptors are blunt ended and Y-shaped, and are less than or equal to 80 nucleic acid bases in length. In some embodiments, the sequencing adaptor is up to 70 bases from end to end.

In another aspect, a method for detecting sequence variants in a cell free DNA sample, comprising detecting rare DNA at a concentration less than 1% with a specificity that is greater than 99.9%.

In another aspect, a method comprises detecting genetic variants in a sample comprising DNA with a detection limit of at least 1% and specificity greater than 99.9%. In some embodiments, the method further comprises converting cDNA (e.g. cfDNA) into adaptor tagged DNA with a conversion efficiency of at least 30%, 40%, or 50% and reducing sequencing noise (or distortion) by eliminating false positive sequence reads.

Another aspect provides a method, comprising (a) providing a sample comprising a set of double-stranded polynucleotide molecules, each double-stranded polynucleotide molecule including first and second complementary strands; (b) tagging the double-stranded polynucleotide molecules with a set of duplex tags, wherein each duplex tag differently tags the first and second complementary strands of a double-stranded polynucleotide molecule in the set; (c) sequencing at least some of the tagged strands to produce a set of sequence reads; (d) reducing and/or tracking redundancy in the set of sequence reads; (e) sorting sequence reads into paired reads and unpaired reads, wherein (i) each paired read corresponds to sequence reads generated from a first tagged strand and a second differently tagged complementary strand derived from a double-stranded polynucleotide molecule in the set, and (ii) each unpaired read represents a first tagged strand having no second differently tag complementary strand derived from a double-stranded polynucleotide molecule represented among the sequence reads in the set of sequence reads; (f) determining quantitative measures of (i) the paired reads and (ii) the unpaired reads that map to each of one or more genetic loci; and (g) estimating with a programmed computer processor a quantitative measure of total double-stranded polynucleotide molecules in the set that map to each of the one or more genetic loci based on the quantitative measure of paired reads and unpaired reads mapping to each locus.

In some embodiments, the method further comprises (h) detecting copy number variation in the sample by determining a normalized total quantitative measure determined in step (g) at each of the one or more genetic loci and determining copy number variation based on the normalized measure. In some embodiments, the sample comprises double-stranded polynucleotide molecules sourced substantially from cell-free nucleic acids. In some embodiments, the duplex tags are not sequencing adaptors.

In some embodiments, reducing redundancy in the set of sequence reads comprises collapsing sequence reads produced from amplified products of an original polynucleotide molecule in the sample back to the original polynucleotide molecule. In some embodiments, the method further comprises determining a consensus sequence for the original polynucleotide molecule. In some embodiments, the method further comprises identifying polynucleotide molecules at one or more genetic loci comprising a sequence variant. In some embodiments, the method further comprises determining a quantitative measure of paired reads that map to a locus, wherein both strands of the pair comprise a sequence variant. In some embodiments, the method further comprises determining a quantitative measure of paired molecules in which only one member of the pair bears a sequence variant and/or determining a quantitative measure of unpaired molecules bearing a sequence variant. In some embodiments, the sequence variant is selected from the group consisting of a single nucleotide variant, an indel, a transversion, a translocation, an inversion, a deletion, a chromosomal structure alteration, a gene fusion, a chromosome fusion, a gene truncation, a gene amplification, a gene duplication and a chromosomal lesion.

Another aspect provides a system comprising a computer readable medium comprising machine-executable code that, upon execution by a computer processor, implements a method comprising (a) receiving into memory a set of sequence reads of polynucleotides tagged with duplex tags; (b) reducing and/or tracking redundancy in the set of sequence reads; (c) sorting sequence reads into paired reads and unpaired reads, wherein (i) each paired read corresponds to sequence reads generated from a first tagged strand and a second differently tagged complementary strand derived from a double-stranded polynucleotide molecule in the set, and (ii) each unpaired read represents a first tagged strand having no second differently tag complementary strand derived from a double-stranded polynucleotide molecule represented among the sequence reads in the set of sequence reads; (d) determining quantitative measures of (i) the paired reads and (ii) the unpaired reads that map to each of one or more genetic loci; and (e) estimating a quantitative measure of total double-stranded polynucleotide molecules in the set that map to each of the one or more genetic loci based on the quantitative measure of paired reads and unpaired reads mapping to each locus.

Another aspect provides a method, comprising (a) providing a sample comprising a set of double-stranded polynucleotide molecules, each double-stranded polynucleotide molecule including first and second complementary strands; (b) tagging the double-stranded polynucleotide molecules with a set of duplex tags, wherein each duplex tag differently tags the first and second complementary strands of a double-stranded polynucleotide molecule in the set; (c) sequencing at least some of the tagged strands to produce a set of sequence reads; (d) reducing and/or tracking redundancy in the set of sequence reads; (e) sorting sequence reads into paired reads and unpaired reads, wherein (i) each paired read corresponds to sequence reads generated from a first tagged strand and a second differently tagged complementary strand derived from a double-stranded polynucleotide molecule in the set, and (ii) each unpaired read represents a first tagged strand having no second differently tag complementary strand derived from a double-stranded polynucleotide molecule represented among the sequence reads in the set of sequence reads; and (f) determining quantitative measures of at least two of (i) the paired reads, (ii) the unpaired reads that map to each of one or more genetic loci, (iii) read depth of the paired reads and (iv) read depth of unpaired reads.

In some embodiments, (f) comprises determining quantitative measures of at least three of (i)-(iv). In some embodiments, (f) comprises determining quantitative measures of all of (i)-(iv). In some embodiments, the method further comprises (g) estimating with a programmed computer processor a quantitative measure of total double-stranded polynucleotide molecules in the set that map to each of the one or more genetic loci based on the quantitative measure of paired reads and unpaired reads and their read depths mapping to each locus.

In another aspect, a method comprises (a) tagging control parent polynucleotides with a first tag set to produce tagged control parent polynucleotides, wherein the first tag set comprises a plurality of tags, wherein each tag in the first tag set comprises a same control tag and an identifying tag, and wherein the tag set comprises a plurality of different identifying tags; (b) tagging test parent polynucleotides with a second tag set to produce tagged test parent polynucleotides, wherein the second tag set comprises a plurality of tags, wherein each tag in the second tag set comprises a same test tag that is distinguishable from the control tag and an identifying tag, and wherein the second tag set comprises a plurality of different identifying tags; (c) mixing tagged control parent polynucleotides with tagged test parent polynucleotides to form a pool; (d) amplifying tagged parent polynucleotides in the pool to form a pool of amplified, tagged polynucleotides; (e) sequencing amplified, tagged polynucleotides in the amplified pool to produce a plurality of sequence reads; (f) grouping sequence reads into families, each family comprising sequence reads generated from a same parent polynucleotide, which grouping is optionally based on information from an identifying tag and from start/end sequences of the parent polynucleotides, and, optionally, determining a consensus sequence for each of a plurality of parent polynucleotides from the plurality of sequence reads in a group; (g) classifying each family or consensus sequence as a control parent polynucleotide or as a test parent polynucleotide based on having a test tag or a control tag; (h) determining a quantitative measure of control parent polynucleotides and control test polynucleotides mapping to each of at least two genetic loci; and (i) determining copy number variation in the test parent polynucleotides at at least one locus based on relative quantity of test parent polynucleotides and control parent polynucleotides mapping to the at least one locus.

In another aspect, a method comprises (a) generating a plurality of sequence reads from a plurality of template polynucleotides, each polynucleotide mapped to a genomic locus; (b) grouping the sequence reads into families, each family comprising sequence reads generated from one of the template polynucleotides; (c) calling a base (or sequence) at the genomic locus for each of the families; (d) detecting at the genomic locus any of genomic alterations among the calls, frequency of a genetic alteration among the calls, total number of calls and total number of alterations among the calls.

In some embodiments, calling comprises any of phylogenetic analysis, voting, weighing, assigning a probability to each read at the locus in a family, and calling the base with the highest probability. In some embodiments, the method is performed at two loci, comprising determining CNV at one of the loci based on counts at each of the loci.

Another aspect provides a method for determining a quantitative measure indicative of a number of individual double-stranded DNA fragments in a sample comprising (a) determining a quantitative measure of individual DNA molecules for which both strands are detected; (b) determining a quantitative measure of individual DNA molecules for which only one of the DNA strands are detected; (c) inferring from (a) and (b) above a quantitative measure of individual DNA molecules for which neither strand was detected; and (d) using (a)-(c) determining the quantitative measure indicative of a number of individual double-stranded DNA fragments in the sample.

In some embodiments, the method further comprises detecting copy number variation in the sample by determining a normalized quantitative measure determined in step (d) at each of one or more genetic loci and determining copy number variation based on the normalized measure. In some embodiments, the sample comprises double-stranded polynucleotide molecules sourced substantially from cell-free nucleic acids.

In some embodiments, determining the quantitative measure of individual DNA molecules comprises tagging the DNA molecules with a set of duplex tags, wherein each duplex tag differently tags complementary strands of a double-stranded DNA molecule in the sample to provide tagged strands. In some embodiments, the method further comprises sequencing at least some of the tagged strands to produce a set of sequence reads. In some embodiments, the method further comprises sorting sequence reads into paired reads and unpaired reads, wherein (i) each paired read corresponds to sequence reads generated from a first tagged strand and a second differently tagged complementary strand derived from a double-stranded polynucleotide molecule in the set, and (ii) each unpaired read represents a first tagged strand having no second differently tag complementary strand derived from a double-stranded polynucleotide molecule represented among the sequence reads in the set of sequence reads. In some embodiments, the method further comprises determining quantitative measures of (i) the paired reads and (ii) the unpaired reads that map to each of one or more genetic loci to determine a quantitative measure of total double-stranded DNA molecules in the sample that map to each of the one or more genetic loci based on the quantitative measure of paired reads and unpaired reads mapping to each locus.

In another aspect, a method for reducing distortion in a sequencing assay, comprises (a) tagging control parent polynucleotides with a first tag set to produce tagged control parent polynucleotides; (b) tagging test parent polynucleotides with a second tag set to produce tagged test parent polynucleotides; (c) mixing tagged control parent polynucleotides with tagged test parent polynucleotides to form a pool; (d) determining quantities of tagged control parent polynucleotides and tagged test parent polynucleotides; and (e) using the quantities of tagged control parent polynucleotides to reduce distortion in the quantities of tagged test parent polynucleotides.

In some embodiments, the first tag set comprises a plurality of tags, wherein each tag in the first tag set comprises a same control tag and an identifying tag, and wherein the first tag set comprises a plurality of different identifying tags. In some embodiments, the second tag set comprises a plurality of tags, wherein each tag in the second tag set comprises a same test tag and an identifying tag, wherein the test tag is distinguishable from the control tag, and wherein the second tag set comprises a plurality of different identifying tags. In some embodiments, (d) comprises amplifying tagged parent polynucleotides in the pool to form a pool of amplified, tagged polynucleotides, and sequencing amplified, tagged polynucleotides in the amplified pool to produce a plurality of sequence reads. In some embodiments, the method further comprises grouping sequence reads into families, each family comprising sequence reads generated from a same parent polynucleotide, which grouping is optionally based on information from an identifying tag and from start/end sequences of the parent polynucleotides, and, optionally, determining a consensus sequence for each of a plurality of parent polynucleotides from the plurality of sequence reads in a group.

In some embodiments, (d) comprises determining copy number variation in the test parent polynucleotides at greater than or equal to one locus based on relative quantity of test parent polynucleotides and control parent polynucleotides mapping to the locus.

Another aspect provides a method comprising (a) ligating adaptors to double-stranded DNA polynucleotides, wherein ligating is performed in a single reaction vessel, and wherein the adaptors comprise molecular barcodes, to produce a tagged library comprising an insert from the double-stranded DNA polynucleotides, and having between 4 and 1 million different tags; (b) generating a plurality of sequence reads for each of the double-stranded DNA polynucleotides in the tagged library; (c) grouping sequence reads into families, each family comprising sequence reads generated from a single DNA polynucleotide among the double-stranded DNA polynucleotides, based on information in a tag and information at an end of the insert; and (d) calling bases at each position in the double-stranded DNA molecule based on bases at the position in members of a family. In some embodiments, (b) comprises amplifying each of the double-stranded DNA polynucleotide molecules in the tagged library to generate amplification products, and sequencing the amplification products. In some embodiments, the method further comprises sequencing the double-stranded DNA polynucleotide molecules a plurality of times. In some embodiments, (b) comprises sequencing the entire insert. In some embodiments, (c) further comprises collapsing sequence reads in each family to generate a consensus sequence. In some embodiments, (d) comprises calling a plurality of sequential bases from at least a subset of the sequence reads to identify single nucleotide variations (SNV) in the double-stranded DNA molecule.

Another aspect provides a method of detecting disease cell heterogeneity from a sample comprising polynucleotides from somatic cells and disease cells. The method comprises quantifying polynucleotides in the sample bearing a nucleotide sequence variant at each of a plurality of genetic loci; determining copy number variation (CNV) at each of the plurality of genetic loci, wherein the CNV indicates a genetic dose of a locus in the disease cell polynucleotides; determining with a programmed computer processor a relative measure of quantity of polynucleotides bearing a sequence variant at a locus per the genetic dose at the locus for each of a plurality of the loci; and comparing the relative measures at each of the plurality of loci, wherein different relative measures is indicative of tumor heterogeneity.

In another aspect, a method comprises subjecting a subject to one or more pulsed therapy cycles, each pulsed therapy cycle comprising (a) a first period during which a drug is administered at a first amount; and (b) a second period during which the drug is administered at a second, reduced amount, wherein (i) the first period is characterized by a tumor burden detected above a first clinical level; and (ii) the second period is characterized by a tumor burden detected below a second clinical level.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

DETAILED DESCRIPTION

Figure 1:
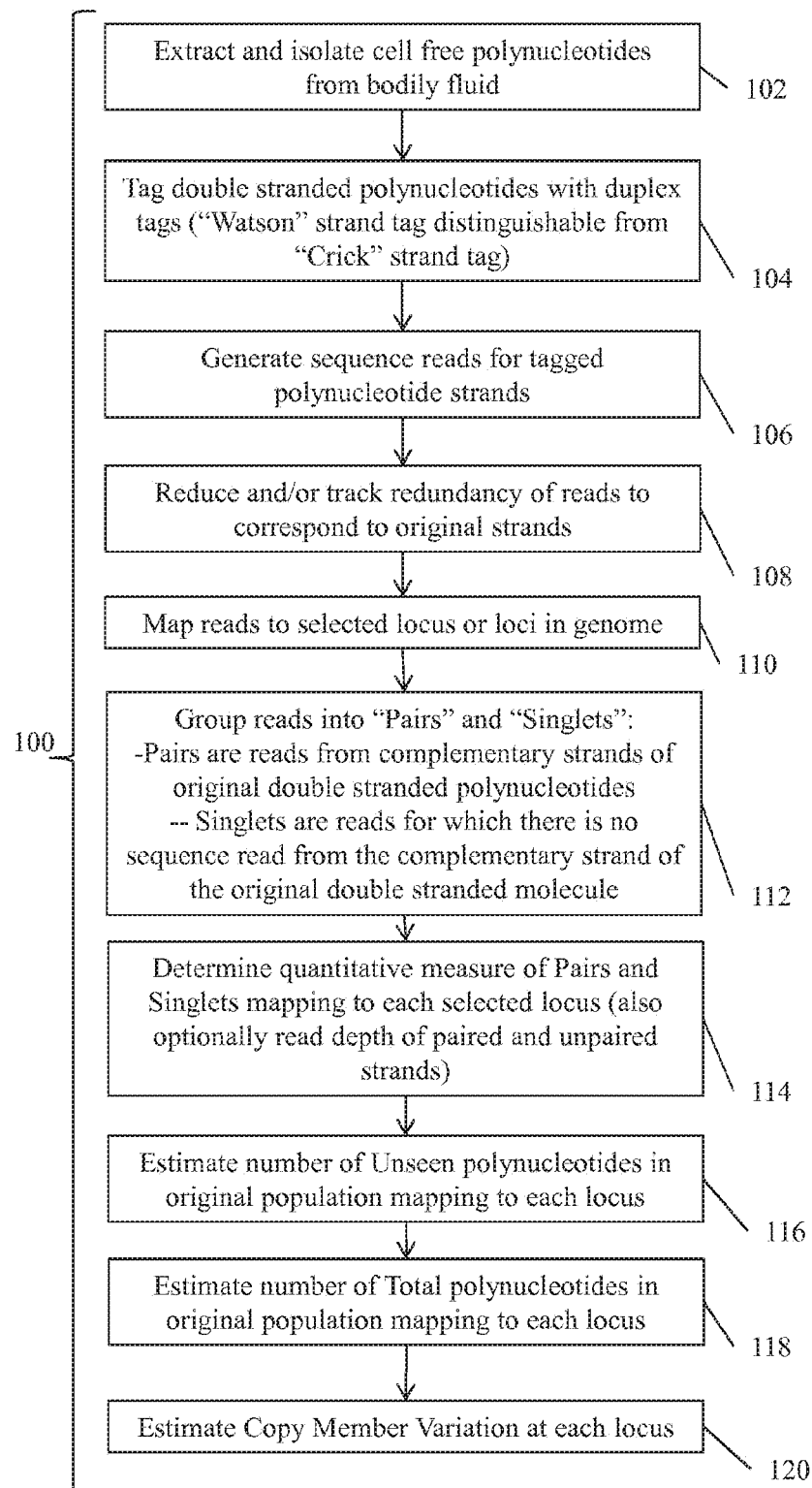
FIG. 1 is a flowchart representation of a method of the present disclosure for determining copy number variation (CNV)

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "genetic variant," as used herein, generally refers to an alteration, variant or polymorphism in a nucleic acid sample or genome of a subject. Such alteration, variant or polymorphism can be with respect to a reference genome, which may be a reference genome of the subject or other individual. Single nucleotide polymorphisms (SNPs) are a form of polymorphisms. In some examples, one or more polymorphisms comprise one or more single nucleotide variations (SNVs), insertions, deletions, repeats, small insertions, small deletions, small repeats, structural variant junctions, variable length tandem repeats, and/or flanking sequences. Copy number variants (CNVs), transversions and other rearrangements are also forms of genetic variation. A genomic alternation may be a base change, insertion, deletion, repeat, copy number variation, or transversion.

The term "polynucleotide," as used herein, generally refers to a molecule comprising one or more nucleic acid subunits. A polynucleotide can include one or more subunits selected from adenosine (A), cytosine (C), guanine (G), thymine (T) and uracil (U), or variants thereof. A nucleotide can include A, C, G, T or U, or variants thereof. A nucleotide can include any subunit that can be incorporated into a growing nucleic acid strand. Such subunit can be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit can enable individual nucleic acid bases or groups of bases (e.g., AA, TA, AT, GC, CG, CT, TC, GT, TG, AC, CA, or uracil-counterparts thereof) to be resolved. In some examples, a polynucleotide is deoxyribonucleic acid (DNA) or ribonucleic acid (RNA), or derivatives thereof. A polynucleotide can be single-stranded or double stranded.

The term "subject," as used herein, generally refers to an animal, such as a mammalian species (e.g., human) or avian (e.g., bird) species, or other organism, such as a plant. More specifically, the subject can be a vertebrate, a mammal, a mouse, a primate, a simian or a human. Animals include, but are not limited to, farm animals, sport animals, and pets. A subject can be a healthy individual, an individual that has or is suspected of having a disease or a pre-disposition to the disease, or an individual that is in need of therapy or suspected of needing therapy. A subject can be a patient.

The term "genome" generally refers to an entirety of an organism's hereditary information. A genome can be encoded either in DNA or in RNA. A genome can comprise coding regions that code for proteins as well as non-coding regions. A genome can include the sequence of all chromosomes together in an organism. For example, the human genome has a total of 46 chromosomes. The sequence of all of these together constitutes a human genome.

The terms "adaptor(s)", "adapter(s)" and "tag(s)" are used synonymously throughout this specification. An adaptor or tag can be coupled to a polynucleotide sequence to be "tagged" by any approach including ligation, hybridization, or other approaches.

The term "library adaptor" or "library adapter" as used herein, generally refers to a molecule (e.g., polynucleotide) whose identity (e.g., sequence) can be used to differentiate polynucleotides in a biological sample (also "sample" herein).

The term "sequencing adaptor," as used herein, generally refers to a molecule (e.g., polynucleotide) that is adapted to permit a sequencing instrument to sequence a target polynucleotide, such as by interacting with the target polynucleotide to enable sequencing. The sequencing adaptor permits the target polynucleotide to be sequenced by the sequencing instrument. In an example, the sequencing adaptor comprises a nucleotide sequence that hybridizes or binds to a capture polynucleotide attached to a solid support of a sequencing system, such as a flow cell. In another example, the sequencing adaptor comprises a nucleotide sequence that hybridizes or binds to a polynucleotide to generate a hairpin loop, which permits the target polynucleotide to be sequenced by a sequencing system. The sequencing adaptor can include a sequencer motif, which can be a nucleotide sequence that is complementary to a flow cell sequence of other molecule (e.g., polynucleotide) and usable by the sequencing system to sequence the target polynucleotide. The sequencer motif can also include a primer sequence for use in sequencing, such as sequencing by synthesis. The sequencer motif can include the sequence(s) needed to couple a library adaptor to a sequencing system and sequence the target polynucleotide.

As used herein the terms "at least", "at most" or "about", when preceding a series, refers to each member of the series, unless otherwise identified.

The term "about" and its grammatical equivalents in relation to a reference numerical value can include a range of values up to plus or minus 10% from that value. For example, the amount "about 10" can include amounts from 9 to 11. In other embodiments, the term "about" in relation to a reference numerical value can include a range of values plus or minus 10%, 9%, 8%, 7%, 6%, 5%, 4%, 3%, 2%, or 1% from that value.

The term "at least" and its grammatical equivalents in relation to a reference numerical value can include the reference numerical value and greater than that value. For example, the amount "at least 10" can include the value 10 and any numerical value above 10, such as 11, 100, and 1,000.

The term "at most" and its grammatical equivalents in relation to a reference numerical value can include the reference numerical value and less than that value. For example, the amount "at most 10" can include the value 10 and any numerical value under 10, such as 9, 8, 5, 1, 0.5, and 0.1.

1. Methods for Processing and/or Analyzing a Nucleic Acid Sample

An aspect of the present disclosure provides methods for determining a genomic alternation in a nucleic acid sample of a subject. FIG. 1 shows a method of determining copy number variation (CNV). The method can be implemented to determine other genomic alternations, such as SNVs.

A. Polynucleotide Isolation

Methods disclosed herein can comprise isolating one or more polynucleotides. A polynucleotide can comprise any type of nucleic acid, for example, a sequence of genomic nucleic acid, or an artificial sequence (e.g., a sequence not found in genomic nucleic acid). For example, an artificial sequence can contain non-natural nucleotides. Also, a polynucleotide can comprise both genomic nucleic acid and an artificial sequence, in any portion. For example, a polynucleotide can comprise 1 to 99% of genomic nucleic acid and 99% to 1% of artificial sequence, where the total adds up to 100%. Thus, fractions of percentages are also contemplated. For example, a ratio of 99.1% to 0.9% is contemplated.

A polynucleotide can comprise any type of nucleic acids, such as DNA and/or RNA. For example, if a polynucleotide is DNA, it can be genomic DNA, complementary DNA (cDNA), or any other deoxyribonucleic acid. A polynucleotide can also be cell-free DNA (cfDNA). For example, the polynucleotide can be circulating DNA. The circulating DNA can comprise circulating tumor DNA (ctDNA). A polynucleotide can be double-stranded or single-stranded. Alternatively, a polynucleotide can comprise a combination of a double-stranded portion and a single-stranded portion.

Polynucleotides do not have to be cell-free. In some cases, the polynucleotides can be isolated from a sample. For example, in step (102) (FIG. 1), double-stranded polynucleotides are isolated from a sample. A sample can be any biological sample isolated from a subject. For example, a sample can comprise, without limitation, bodily fluid, whole blood, platelets, serum, plasma, stool, red blood cells, white blood cells or leucocytes, endothelial cells, tissue biopsies, synovial fluid, lymphatic fluid, ascites fluid, interstitial or extracellular fluid, the fluid in spaces between cells, including gingival crevicular fluid, bone marrow, cerebrospinal fluid, saliva, mucous, sputum, semen, sweat, urine, or any other bodily fluids. A bodily fluid can include saliva, blood, or serum. For example, a polynucleotide can be cell-free DNA isolated from a bodily fluid, e.g., blood or serum. A sample can also be a tumor sample, which can be obtained from a subject by various approaches, including, but not limited to, venipuncture, excretion, ejaculation, massage, biopsy, needle aspirate, lavage, scraping, surgical incision, or intervention or other approaches.

A sample can comprise various amount of nucleic acid that contains genome equivalents. For example, a sample of about 30 ng DNA can contain about 10,000 ($10^4$) haploid human genome equivalents and, in the case of cfDNA, about 200 billion ($2 \times 10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources. For example, a sample can comprise germline DNA or somatic DNA. A sample can comprise nucleic acids carrying mutations. For example, a sample can comprise DNA carrying germline mutations and/or somatic mutations. A sample can also comprise DNA carrying cancer-associated mutations (e.g., cancer-associated somatic mutations).

B. Tagging

Polynucleotides disclosed herein can be tagged. For example, in step (104) (FIG. 1) the double-stranded polynucleotides are tagged with duplex tags, tags that differently label the complementary strands (i.e., the "Watson" and "Crick" strands) of a double-stranded molecule. In one embodiment the duplex tags are polynucleotides having complementary and non-complementary portions.

Tags can be any types of molecules attached to a polynucleotide, including, but not limited to, nucleic acids, chemical compounds, fluorescent probes, or radioactive probes. Tags can also be oligonucleotides (e.g., DNA or RNA). Tags can comprise known sequences, unknown sequences, or both. A tag can comprise random sequences, pre-determined sequences, or both. A tag can be double-stranded or single-stranded. A double-stranded tag can be a duplex tag. A double-stranded tag can comprise two complementary strands. Alternatively, a double-stranded tag can comprise a hybridized portion and a non-hybridized portion. The double-stranded tag can be Y-shaped, e.g., the hybridized portion is at one end of the tag and the non-hybridized portion is at the opposite end of the tag. One such example are the "Y adapters" used in Illumina sequencing. Other examples include hairpin shaped adapters or bubble shaped adapters. Bubble shaped adapters have non-complementary sequences flanked on both sides by complementary sequences.

Tagging disclosed herein can be performed using any method. A polynucleotide can be tagged with an adaptor by hybridization. For example, the adaptor can have a nucleotide sequence that is complementary to at least a portion of a sequence of the polynucleotide. As an alternative, a polynucleotide can be tagged with an adaptor by ligation.

For example, tagging can comprise using one or more enzymes. The enzyme can be a ligase. The ligase can be a DNA ligase. For example, the DNA ligase can be a T4 DNA ligase, *E. coli* DNA ligase, and/or mammalian ligase. The mammalian ligase can be DNA ligase I, DNA ligase III, or DNA ligase IV. The ligase can also be a thermostable ligase. Tags can be ligated to a blunt-end of a polynucleotide (blunt-end ligation). Alternatively, tags can be ligated to a sticky end of a polynucleotide (sticky-end ligation). Efficiency of ligation can be increased by optimizing various conditions. Efficiency of ligation can be increased by optimizing the reaction time of ligation. For example, the reaction time of ligation can be less than 12 hours, e.g., less than 1, less than 2, less than 3, less than 4, less than 5, less than 6, less than 7, less than 8, less than 9, less than 10, less than 11, less than 12, less than 13, less than 14, less than 15, less than 16, less than 17, less than 18, less than 19, or less than 20 hours. In a particular example, reaction time of ligation is less than 20 hours. Efficiency of ligation can be increased by optimizing the ligase concentration in the reaction. For example, the ligase concentration can be at least 10, at least 50, at least 100, at least 150, at least 200, at least 250, at least 300, at least 400, at least 500, or at least 600 unit/microliter. Efficiency can also be optimized by adding or varying the concentration of an enzyme suitable for ligation, enzyme cofactors or other additives, and/or optimizing a temperature of a solution having the enzyme.

Efficiency can also be optimized by varying the addition order of various components of the reaction. The end of tag sequence can comprise dinucleotide to increase ligation efficiency. When the tag comprises a non-complementary portion (e.g., Y-shaped adaptor), the sequence on the complementary portion of the tag adaptor can comprise one or more selected sequences that promote ligation efficiency. Preferably such sequences are located at the terminal end of the tag. Such sequences can comprise 1, 2, 3, 4, 5, or 6 terminal bases. Reaction solution with high viscosity (e.g., a low Reynolds number) can also be used to increase ligation efficiency. For example, solution can have a Reynolds number less than 3000, less than 2000, less than 1000, less than 900, less than 800, less than 700, less than 600, less than 500, less than 400, less than 300, less than 200, less than 100, less than 50, less than 25, or less than 10. It is also contemplated that roughly unified distribution of fragments (e.g., tight standard deviation) can be used to increase ligation efficiency. For example, the variation in fragment sizes can vary by less than 20%, less than 15%, less than 10%, less than 5%, or less than 1%. Tagging can also comprise primer extension, for example, by polymerase chain reaction (PCR). Tagging can also comprise any of ligation-based PCR, multiplex PCR, single strand ligation, or single strand circularization.

In some instances, the tags herein comprise molecular barcodes. Such molecular barcodes can be used to differentiate polynucleotides in a sample. Preferably molecular barcodes are different from one another. For example, molecular barcodes can have a difference between them that can be characterized by a predetermined edit distance or a Hamming distance. In some instances, the molecular barcodes herein have a minimum edit distance of 1, 2, 3, 4, 5, 6, 7, 8, 9, or 10. To further improve efficiency of conversion (e.g., tagging) of untagged molecular to tagged molecules, one preferably utilizes short tags. For example, in some embodiments, a library adapter tag can be up to 65, 60, 55, 50, 45, 40, or 35 nucleotide bases in length. A collection of such short library barcodes preferably includes a number of different molecular barcodes, e.g., at least 2, 4, 6, 8, 10, 12, 14, 16, 18 or 20 different barcodes with a minimum edit distance of 1, 2, 3 or more.

Thus, a collection of molecules can include one or more tags. In some instances, some molecules in a collection can include an identifying tag ("identifier") such as a molecular barcode that is not shared by any other molecule in the collection. For example, in some instances of a collection of molecules, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the molecules in the collection can include an identifier or molecular barcode that is not shared by any other molecule in the collection. As used herein, a collection of molecules is considered to be "uniquely tagged" if each of at least 95% of the molecules in the collection bears an identifier that is not shared by any other molecule in the collection ("unique tag" or "unique identifier"). A collection of molecules is considered to be "non-uniquely tagged" if each of at least 1%, at least 5%, at least 10%, at least 15%, at least 20%, at least 25%, at least 30%, at least 35%, at least 40%, at least 45%, or at least or about 50% of the molecules in the collection bears an identifying tag or molecular barcode that is shared by at least one other molecule in the collection ("non-unique tag" or "non-unique identifier"). Accordingly, in a non-uniquely tagged population no more than 1% of the molecules are uniquely tagged. For example, in a non-uniquely tagged population, no more than 1%, 5%, 10%, 15%, 20%, 25%, 30%, 35%, 40%, 45%, or 50% of the molecules can be uniquely tagged.

A number of different tags can be used based on the estimated number of molecules in a sample. In some tagging methods, the number of different tags can be at least the same as the estimated number of molecules in the sample. In other tagging methods, the number of different tags can be at least two, three, four, five, six, seven, eight, nine, ten, one hundred or one thousand times as many as the estimated number of molecules in the sample. In unique tagging, at least two times (or more) as many different tags can be used as the estimated number of molecules in the sample.

The molecules in the sample may be non-uniquely tagged. In such instances a fewer number of tags or molecular barcodes is used then the number of molecules in the sample to be tagged. For example, no more than 100, 50, 40, 30, 20 or 10 unique tags or molecular barcodes are used to tag a complex sample such as a cell free DNA sample with many more different fragments.

The polynucleotide to be tagged can be fragmented, such as either naturally or using other approaches, such as, for example, shearing. The polynucleotides can be fragmented by certain methods, including but not limited to, mechanical shearing, passing the sample through a syringe, sonication, heat treatment (e.g., for 30 minutes at 90° C.), and/or nuclease treatment (e.g., using DNase, RNase, endonuclease, exonuclease, and/or restriction enzyme).

The polynucleotides fragments (prior to tagging) can comprise sequences of any length. For example, polynucleotide fragments (prior to tagging) can comprise at least 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1000, 1100, 1200, 1300, 1400, 1500, 1600, 1700, 1800, 1900, 2000 or more nucleotides in length. The polynucleotide fragment are preferably about the average length of cell-free DNA. For example, the polynucleotide fragments can comprise about 160 bases in length. The polynucleotide fragment can also be fragmented from a larger fragment into smaller fragments about 160 bases in length.

Polynucleotides tagged can comprise sequences associated with cancer. The cancer-associated sequences can comprise single nucleotide variation (SNV), copy number variation (CNV), insertions, deletions, and/or rearrangements.

The polynucleotides can comprise sequences associated with cancer, such as acute lymphoblastic leukemia (ALL), acute myeloid leukemia (AML), adrenocortical carcinoma, Kaposi Sarcoma, anal cancer, basal cell carcinoma, bile duct cancer, bladder cancer, bone cancer, osteosarcoma, malignant fibrous histiocytoma, brain stem glioma, brain cancer, craniopharyngioma, ependymoblastoma, ependymoma, medulloblastoma, medulloepithelioma, pineal parenchymal tumor, breast cancer, bronchial tumor, Burkitt lymphoma, Non-Hodgkin lymphoma, carcinoid tumor, cervical cancer, chordoma, chronic lymphocytic leukemia (CLL), chronic myelogenous leukemia (CML), colon cancer, colorectal cancer, cutaneous T-cell lymphoma, ductal carcinoma in situ, endometrial cancer, esophageal cancer, Ewing Sarcoma, eye cancer, intraocular melanoma, retinoblastoma, fibrous histiocytoma, gallbladder cancer, gastric cancer, glioma, hairy cell leukemia, head and neck cancer, heart cancer, hepatocellular (liver) cancer, Hodgkin lymphoma, hypopharyngeal cancer, kidney cancer, laryngeal cancer, lip cancer, oral cavity cancer, lung cancer, non-small cell carcinoma, small cell carcinoma, melanoma, mouth cancer, myelodysplastic syndromes, multiple myeloma, medulloblastoma, nasal cavity cancer, paranasal sinus cancer, neuroblastoma, nasopharyngeal cancer, oral cancer, oropharyngeal cancer, osteosarcoma, ovarian cancer, pancreatic cancer, papillomatosis, paraganglioma, parathyroid cancer, penile cancer, pharyngeal cancer, pituitary tumor, plasma cell neoplasm, prostate cancer, rectal cancer, renal cell cancer, rhabdomyosarcoma, salivary gland cancer, Sezary syndrome, skin cancer, nonmelanoma, small intestine cancer, soft tissue sarcoma, squamous cell carcinoma, testicular cancer, throat cancer, thymoma, thyroid cancer, urethral cancer, uterine cancer, uterine sarcoma, vaginal cancer, vulvar cancer, Waldenstrom macroglobulinemia, and/or Wilms Tumor.

A haploid human genome equivalent has about 3 picograms of DNA. A sample of about 1 microgram of DNA contains about 300,000 haploid human genome equivalents. Improvements in sequencing can be achieved as long as at least some of the duplicate or cognate polynucleotides bear unique identifiers with respect to each other, that is, bear different tags. However, in certain embodiments, the number of tags used is selected so that there is at least a 95% chance that all duplicate molecules starting at any one position bear unique identifiers. For example, in a sample comprising about 10,000 haploid human genome equivalents of fragmented genomic DNA, e.g., cfDNA, z is expected to be between 2 and 8. Such a population can be tagged with between about 10 and 100 different identifiers, for example, about 2 identifiers, about 4 identifiers, about 9 identifiers, about 16 identifiers, about 25 identifiers, about 36 different identifiers, about 49 different identifiers, about 64 different identifiers, about 81 different identifiers, or about 100 different identifiers.

Nucleic acid barcodes having identifiable sequences including molecular barcodes, can be used for tagging. For example, a plurality of DNA barcodes can comprise various numbers of sequences of nucleotides. A plurality of DNA barcodes having 2, 3, 4, 5, 6, 7, 8, 9, 10, 11, 12, 13, 14, 15, 16, 17, 18, 19, 20, 21, 22, 23, 24, 25, 26, 27, 28, 29, 30 or more identifiable sequences of nucleotides can be used. When attached to only one end of a polynucleotide, the plurality of DNA barcodes can produce 2, 3, 4, 5, 6, 7, 8, 9, 10, 11, 12, 13, 14, 15, 16, 17, 18, 19, 20, 21, 22, 23, 24, 25, 26, 27, 28, 29, 30 or more different identifiers. Alternatively, when attached to both ends of a polynucleotide, the plurality DNA barcodes can produce 4, 9, 16, 25, 36, 49, 64, 81, 100, 121, 144, 169, 196, 225, 256, 289, 324, 361, 400 or more different identifiers (which is the ^2 of when the DNA barcode is attached to only 1 end of a polynucleotide). In one example, a plurality of DNA barcodes having 6, 7, 8, 9 or 10 identifiable sequences of nucleotides can be used. When attached to both ends of a polynucleotide, they produce 36, 49, 64, 81 or 100 possible different identifiers, respectively. In a particular example, the plurality of DNA barcodes can comprise 8 identifiable sequences of nucleotides. When attached to only one end of a polynucleotide, the plurality of DNA barcodes can produce 8 different identifiers. Alternatively, when attached to both ends of a polynucleotide, the plurality of DNA barcodes can produce 64 different identifiers. Samples tagged in such a way can be those with a range of about 10 ng to any of about 100 ng, about 1 µg, about 10 µg of fragmented polynucleotides, e.g., genomic DNA, e.g., cfDNA.

A polynucleotide can be uniquely identified in various ways. A polynucleotide can be uniquely identified by a unique DNA barcode. For example, any two polynucleotides in a sample are attached two different DNA barcodes. Alternatively, a polynucleotide can be uniquely identified by the combination of a DNA barcode and one or more endogenous sequences of the polynucleotide. For example, any two polynucleotides in a sample can be attached the same DNA barcode, but the two polynucleotides can still be identified by different endogenous sequences. The endogenous sequence can be on an end of a polynucleotide. For example, the endogenous sequence can be adjacent (e.g., base in between) to the attached DNA barcode. In some instances the endogenous sequence can be at least 2, 4, 6, 8, 10, 20, 30, 40, 50, 60, 70, 80, 90, or 100 bases in length. Preferably, the endogenous sequence is a terminal sequence of the fragment/polynucleotides to be analyzed. The endogenous sequence may be the length of the sequence. For example, a plurality of DNA barcodes comprising 8 different DNA barcodes can be attached to both ends of each polynucleotide in a sample. Each polynucleotide in the sample can be identified by the combination of the DNA barcodes and about 10 base pair endogenous sequence on an end of the polynucleotide. Without being bound by theory, the endogenous sequence of a polynucleotide can also be the entire polynucleotide sequence.

Also disclosed herein are compositions of tagged polynucleotides. The tagged polynucleotide can be single-stranded. Alternatively, the tagged polynucleotide can be double-stranded (e.g., duplex-tagged polynucleotides). Accordingly, this invention also provides compositions of duplex-tagged polynucleotides. The polynucleotides can comprise any types of nucleic acids (DNA and/or RNA). The polynucleotides comprise any types of DNA disclosed herein. For example, the polynucleotides can comprise DNA, e.g., fragmented DNA or cfDNA. A set of polynucleotides in the composition that map to a mappable base position in a genome can be non-uniquely tagged, that is, the number of different identifiers can be at least 2 and fewer than the number of polynucleotides that map to the mappable base position. The number of different identifiers can also be at least 3, 4, 5, 6, 7, 8, 9, 10, 11, 12, 13, 14, 15, 16, 17, 18, 19, 20, 21, 22, 23, 24, 25 and fewer than the number of polynucleotides that map to the mappable base position.

In some instances, as a composition goes from about 1 ng to about 10 µg or higher, a larger set of different molecular barcodes can be used. For example, between 5 and 100 different library adaptors can be used to tag polynucleotides in a cfDNA sample.

The systems and methods disclosed herein may be used in applications that involve the assignment of molecular barcodes. The molecular barcodes can be assigned to any types of polynucleotides disclosed in this invention. For example, the molecular barcodes can be assigned to cell-free polynucleotides (e.g., cfDNAs). Often, an identifier disclosed herein can be a barcode oligonucleotide that is used to tag the polynucleotide. The barcode identifier may be a nucleic acid oligonucleotide (e.g., a DNA oligonucleotide). The barcode identifier can be single-stranded. Alternatively, the barcode identifier can be double-stranded. The barcode identifier can be attached to polynucleotides using any method disclosed herein. For example, the barcode identifier can be attached to the polynucleotide by ligation using an enzyme. The barcode identifier can also be incorporated into the polynucleotide through PCR. In other cases, the reaction may comprise addition of a metal isotope, either directly to the analyte or by a probe labeled with the isotope. Generally, assignment of unique or non-unique identifiers or molecular barcodes in reactions of this disclosure may follow methods and systems described by, for example, U.S. patent applications 2001/0053519, 2003/0152490, 2011/0160078 and U.S. Pat. No. 6,582,908, each of which is entirely incorporated herein by reference.

Identifiers or molecular barcodes used herein may be completely endogenous whereby circular ligation of individual fragments may be performed followed by random shearing or targeted amplification. In this case, the combination of a new start and stop point of the molecule and the original intramolecular ligation point can form a specific identifier.

Identifiers or molecular barcodes used herein can comprise any types of oligonucleotides. In some cases, identifiers may be predetermined, random, or semi-random sequence oligonucleotides. Identifiers can be barcodes. For example, a plurality of barcodes may be used such that barcodes are not necessarily unique to one another in the plurality. Alternatively, a plurality of barcodes may be used such that each barcode is unique to any other barcode in the plurality. The barcodes can comprise specific sequences (e.g., predetermined sequences) that can be individually tracked. Further, barcodes may be attached (e.g., by ligation) to individual molecules such that the combination of the barcode and the sequence it may be ligated to creates a specific sequence that may be individually tracked. As described herein, detection of barcodes in combination with sequence data of beginning (start) and/or end (stop) portions of sequence reads can allow assignment of a unique identity to a particular molecule. The length or number of base pairs of an individual sequence read may also be used to assign a unique identity to such a molecule. As described herein, fragments from a single strand of nucleic acid having been assigned a unique identity, may thereby permit subsequent identification of fragments from the parent strand. In this way the polynucleotides in the sample can be uniquely or substantially uniquely tagged. A duplex tag can include a degenerate or semi-degenerate nucleotide sequence, e.g., a random degenerate sequence. The nucleotide sequence can comprise any number of nucleotides. For example, the nucleotide sequence can comprise 1 (if using a non-natural nucleotide), 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides. In a particular example, the sequence can comprise 7 nucleotides. In another example, the sequence can comprise 8 nucleotides. The sequence can also comprise 9 nucleotides. The sequence can comprise 10 nucleotides.

A barcode can comprise contiguous or non-contiguous sequences. A barcode that comprises at least 1, 2, 3, 4, 5 or more nucleotides is a contiguous sequence or non-contiguous sequence. if the 4 nucleotides are uninterrupted by any other nucleotide. For example, if a barcode comprises the sequence TTGC, a barcode is contiguous if the barcode is TTGC. On the other hand, a barcode is non-contiguous if the barcode is TTXGC, where X is a nucleic acid base.

An identifier or molecular barcode can have an n-mer sequence which may be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length. A tag herein can comprise any range of nucleotides in length. For example, the sequence can be between 2 to 100, 10 to 90, 20 to 80, 30 to 70, 40 to 60, or about 50 nucleotides in length.

The tag can comprise a double-stranded fixed reference sequence downstream of the identifier or molecular barcode. Alternatively, the tag can comprise a double-stranded fixed reference sequence upstream or downstream of the identifier or molecular barcode. Each strand of a double-stranded fixed reference sequence can be, for example, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides in length.

C. Adaptors

A library of polynucleotide molecules can be synthesized for use in sequencing. For example, a library of polynucleotides comprising a plurality of polynucleotide molecules that are each less than or equal to 100, 90, 80, 70, 60, 50, 45, 40, or 35 nucleic acid (or nucleotide) bases in length can be made. A plurality of polynucleotide molecules can be each less than or equal to 35 nucleic acid bases in length. A plurality of polynucleotide molecules can be each less than or equal to 30 nucleic acid bases in length. A plurality of polynucleotide molecules can also be less than or equal to 250, 200, 150, 100, or 50 nucleic acid bases. Additionally, the plurality of polynucleotide molecules can also be less than or equal to 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, or 10 nucleic acid bases.

A library of polynucleotides comprising a plurality of polynucleotide molecules can also have distinct (with respect to each other) molecular barcode sequences (or molecular barcodes) with respect to at least 4 nucleic acid bases. A molecular barcode (also "barcode" or "identifier" herein) sequence is a nucleotide sequence that distinguishes one polynucleotide from another. In other embodiments, the polynucleotide molecules can also have different barcode sequences with respect to 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleic acid bases.

A library of polynucleotides comprising a plurality of polynucleotide molecules can also have a plurality of different barcode sequences. For example, a plurality of polynucleotide molecules can have at least 4 different molecular barcode sequences. In some cases, the plurality of polynucleotide molecules has from 2-100, 4-50, 4-30, 4-20, or 4-10 different molecular barcode sequences. The plurality of polynucleotides molecules can also have other ranges of different barcode sequences such as, 1-4, 2-5, 3-6, 4-7, 5-8, 6-9, 7-10, 8-11, 9-12, 10-13, 11-14, 12-15, 13-16, 14-17, 15-18, 16-19, 17-20, 18-21, 19-22, 20-23, 21-24, or 22-25 different barcode sequences. In other cases, a plurality of polynucleotide molecules can have at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 more different barcode sequences. In a particular example, the plurality library adapters comprise at least 8 different sequences.

The location of the different barcode sequences can vary within the plurality of polynucleotides. For example, the different barcode sequences can be within 20, 15, 10, 9, 8, 7, 6, 5, 4, 3, or 2 nucleic acid bases from a terminal end of a respective one of the plurality of polynucleotide molecules. In an example, a plurality of polynucleotide molecules has distinct barcode sequences that are within 10 nucleic acid bases from the terminal end. In another example, a plurality of polynucleotide molecules has distinct barcode sequences that are within 5 or 1 nucleic acid bases from the terminal end. In other instances, the distinct barcode sequences can be at the terminal end of a respective one of the plurality of polynucleotide molecules. Other variations include that the distinct molecular barcode sequences can be within 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, or more nucleic acid bases from a terminal end of a respective one of the plurality of polynucleotide molecules.

The terminal end of the plurality of polynucleotide molecules can be adapted for ligation to a target nucleic acid molecule. For example, the terminal end can be a blunt end. In some other cases, the terminal end is adapted for hybridization to a complementary sequence of a target nucleic acid molecule.

A library of polynucleotides comprising a plurality of polynucleotide molecules can also have an edit distance of at least 1. In some cases, the edit distance is with respect to individual bases of the plurality of polynucleotide molecules. In other cases, the plurality of polynucleotide molecules can have an edit distance of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more. The edit distance can be a Hamming distance.

In some cases, the plurality of polynucleotides does not contain sequencing adaptors. A sequence adaptor can be a polynucleotide that comprises a sequence that hybridizes to one or more sequencing adaptors or primers. A sequencing adaptor can further comprise a sequence hybridizing to a solid support, e.g., a flow cell sequence. The term "flow cell sequence" and its grammatical equivalents as used herein, refers to a sequence that permits hybridization to a substrate, for example, by way of a primer attached to the substrate. The substrate can be bead or a planar surface. In some embodiments, a flow cell sequence can allow a polynucleotide to attach to a flow cell or surface (e.g., surface of a bead, for example, an Illumina flow cell.

When a plurality of polynucleotide molecules does not contain sequencing adaptors or primers, each polynucleotide molecule of the plurality does not contain a nucleic acid sequence or other moiety that is adapted to permit sequencing of a target nucleic acid molecule with a given sequencing approach, such as Illumina, SOLiD, Pacific Biosciences, GeneReader, Oxford Nanopore, Complete Genomics, Gnu- Bio, Ion Torrent, Oxford Nanopore or Genia. In some examples, when a plurality of polynucleotide molecules does not contain sequencing adaptors or primers, the plurality of polynucleotide molecules does not contain flow cell sequences. For example, the plurality of polynucleotide molecules cannot bind to flow cells, such as used in Illumina flow cell sequencers. However, these flow cell sequences, if desired, can be added to the plurality of polynucleotide molecules by methods such as PCR amplification or ligation. At this point, Illumina flow cell sequencers can be used. Alternatively, when the plurality of polynucleotide molecules does not contain sequencing adaptors or primers, the plurality of polynucleotide molecules does not contain hairpin shaped adaptors or adaptors for generating hairpin loops in a target nucleic acid molecule, such as Pacific Bioscience SMRTbell™ adaptors. However, these hairpin shaped adaptors, if desired, can be added to the plurality of polynucleotide molecules by methods such as PCR amplification or ligation. The plurality of polynucleotide molecules can be circular or linear.

A plurality of polynucleotide molecules can be double stranded. In some cases, the plurality of polynucleotide molecules can be single stranded, or can comprise hybridized and non-hybridized regions. A plurality of polynucleotide molecules can be non-naturally occurring polynucleotide molecules.

Adaptors can be polynucleotide molecules. The polynucleotide molecules can be Y-shaped, bubble-shaped or hairpin-shaped. A hairpin adaptor may contain a restriction site(s) or a Uracil containing base. Adaptors can comprise a complementary portion and a non-complementary portion. The non-complementary portion can have an edit distance (e.g., Hamming distance). For example, the edit distance can be at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30. The complementary portion of the adaptor can comprise sequences that are selected to enable and/or promote ligation to a polynucleotide, e.g., a sequence to enable and/or promote ligation to a polynucleotide at a high yield.

A plurality of polynucleotide molecules as disclosed herein can be purified. In some cases, a plurality of polynucleotide molecules as disclosed herein can be isolated polynucleotide molecules. In other cases, a plurality of polynucleotide molecules as disclosed herein can be purified and isolated polynucleotide molecules.

In certain aspects, each of the plurality of polynucleotide molecules is Y-shaped or hairpin-shaped. Each of the plurality of polynucleotide molecules can comprise a different barcode. The different barcode can be a randomer in the complementary portion (e.g., double stranded portion) of the Y-shaped or hairpin-shaped adaptor. Alternatively, the different barcode can be in one strand of the non-complementary portion (e.g., one of the Y-shaped arms). As discussed above, the different barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., 7 bases. The barcode can be contiguous or non-contiguous sequences, as described above. The plurality of polynucleotide molecules is from 10 nucleic acid bases to 35 nucleic acid bases (or any length as described above) in length. Further, the plurality of polynucleotide molecules can comprise an edit distance (as described above), that is a Hamming distance. A plurality of polynucleotide molecules can have distinct barcode sequences that are within 10 nucleic acid bases from the terminal end.

In another aspect, a plurality of polynucleotide molecules can be sequencing adaptors. A sequencing adaptor can comprise a sequence hybridizing to one or more sequencing primers. A sequencing adaptor can further comprise a sequence hybridizing to a solid support, e.g., a flow cell sequence. For example, a sequencing adaptor can be a flow cell adaptor. The sequencing adaptors can be attached to one or both ends of a polynucleotide fragment. In another example, a sequencing adaptor can be hairpin shaped. For example, the hairpin shaped adaptor can comprise a complementary double-stranded portion and a loop portion, where the double-stranded portion can be attached (e.g., ligated) to a double-stranded polynucleotide. Hairpin shaped sequencing adaptors can be attached to both ends of a polynucleotide fragment to generate a circular molecule, which can be sequenced multiple times. A sequencing adaptor can be up to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more bases from end to end. For example, a sequencing adaptor can be up to 70 bases from end to end. The sequencing adaptor can comprise 20-30, 20-40, 30-50, 30-60, 40-60, 40-70, 50-60, 50-70, bases from end to end. In a particular example, the sequencing adaptor can comprise 20-30 bases from end to end. In another example, the sequencing adaptor can comprise 50-60 bases from end to end. A sequencing adaptor can comprise one or more barcodes. For example, a sequencing adaptor can comprise a sample barcode. The sample barcode can comprise a pre-determined sequence. The sample barcodes can be used to identify the source of the polynucleotides. The sample barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., at least 8 bases. The barcode can be contiguous or non-contiguous sequences, as described above.

The plurality of polynucleotide molecules as described herein can be used as adaptors. Adaptors can comprise one or more identifiers. An adaptor can comprise an identifier with a random sequence. Alternatively, an adaptor can comprise an identifier with pre-determined sequences. Some adaptors can comprise an identifier with a random sequence and another identifier with a pre-determined sequence. The adaptors comprising identifiers can be double-stranded or single-stranded adaptors. The adaptors comprising identifiers can be Y-shaped adaptors. A Y-shaped adaptor can comprise one or more identifiers with a random sequence. The one or more identifiers can be on the hybrid portion and/or non-hybridized portion of the Y-shaped adaptor. A Y-shaped adaptor can comprise one or more identifiers with a pre-determined sequence. The one or more identifiers with pre-determined sequence can be on the hybridized portion and/or non-hybridized portion of the Y-shaped adaptor. A Y-shaped adaptor can comprise one or more identifiers with a random sequence and one or more identifiers with a pre-determined sequence. For example, the one or more identifiers with a random sequence can be on the hybridized portion of the Y-shaped adaptor and/or the non-hybridized portion of the Y-shaped adaptor. The one or more identifiers with a pre-determined sequence can be on the hybridized portion of the Y-shaped adaptor and/or the non-hybridized portion of the Y-shaped adaptor. In a particular example, a Y-shaped adaptor can comprise an identifier with a random sequence on its hybridized portion and an identifier with a pre-determined sequence on its non-hybridized portion. The identifiers can be in any length disclosed herein. For example, a Y-shaped adaptor can comprise an identifier with a random sequence of 7 nucleotides on its hybridized portion and an identifier with a pre-determined sequence of 8 nucleotides on its non-hybridized portion.

An adaptor can include a double-stranded portion with a molecular barcode and at least one or two single-stranded portion. For example, the adaptor can be Y-shaped and include a double-stranded portion and two single-stranded portions. The single-stranded portions can include sequences that are not complementary to one another.

The adaptor can include a terminal end that has a sequence that is selected to permit the adaptor to be efficiently (e.g., at an efficiency of at least about 20%, 30%, 40%, 50%) ligated or otherwise coupled to a polynucleotide. In some examples, terminal nucleotides in a double-stranded portion of an adaptor are selected from a combination of purines and pyrimidines to provide for efficient ligation.

In some examples, a set of library adaptors comprises a plurality of polynucleotide molecules (library adaptors) with molecular barcodes. The library adaptors are less than or equal to 80, 70, 60, 50, 45, or 40 nucleotide bases in length. The molecular barcodes can be at least 4 nucleotide bases in length, but may be from 4 to 20 nucleotide bases in length. The molecular barcodes can be different from one another and have an edit distance of at least 1, 2, 3, 4, or 5 between one another. The molecular barcodes are located at least 1, 2, 3, 4, 5, 10, or 20 nucleotide bases away from a terminal end of their respective library adaptors. In some cases, the at least one terminal base is identical in all of the library adaptors.

The library adaptors can be identical but for the molecular barcodes. For example, the library adaptors can have identical sequences but differ only with respect to nucleotide sequences of the molecular barcodes.

Each of the library adaptors can have a double stranded portion and at least one single-stranded portion. By "single stranded portion" is meant an area of non-complementarity or an overhang. In some cases, each of the library adaptors has a double-stranded portion and two single-stranded portions. The double-stranded portion can have a molecular barcode. In some cases, the molecular barcode is a randomer. Each of the library adaptors can further include a strand-identification barcode on a single-stranded portion. The strand-identification barcode can include at least 4 nucleotide bases, in some cases from 4 to 20 nucleotide bases.

In some examples, each of the library adaptors has a double-stranded portion with a molecular barcode and two single-stranded portions. The single-stranded portions may not hybridize to one another. The single-stranded portions may not be completely complementary to one another.

The library adaptors can have a sequence of terminal nucleotides in a double-stranded portion that are the same. The sequence of terminal nucleotides can be at least 2, 3, 4, 5 or 6 nucleotide bases in length. For example, one strand of a double-stranded portion of the library adaptor can have the sequence ACTT, TCGC, or TACC at the terminal end, while the other strand can have a complementary sequence. In some cases, such a sequence is selected to optimize the efficiency at which the library adaptors ligate to target polynucleotides. Such sequences can be selected to optimize a binding interaction between the ends of the library adaptors and the target polynucleotides.

In some cases, none of the library adaptors contains a sample identification motif (or sample molecular barcode). Such sample identification motif can be provided via sequencing adaptors. A sample identification motif can include a sequencer of at least 4, 5, 6, 7, 8, 9, 10, 20, 30, or 40 nucleotide bases that permits the identification of polynucleotide molecules from a given sample from polynucleotide molecules from other samples. For example, this can permit polynucleotide molecules from two subjects to be sequenced in the same pool and sequence reads for the subjects subsequently identified.

A sequencer motif includes nucleotide sequence(s) needed to couple a library adaptor to a sequencing system and sequence a target polynucleotide coupled to the library adaptor. The sequencer motif can include a sequence that is complementary to a flow cell sequence and a sequence (sequencing initiation sequence) that is selectively hybridizable to a primer (or priming sequence) for use in sequencing. For example, such sequencing initiation sequence can be complementary to a primer that is employed for use in sequence by synthesis (e.g., Illumina). Such primer can be included in a sequencing adaptor. A sequencing initiation sequence can be a primer hybridization site.

In some cases, none of the library adaptors contains a complete sequencer motif. The library adaptors can contain partial or no sequencer motifs. In some cases, the library adaptors include a sequencing initiation sequence. The library adaptors can include a sequencing initiation sequence but no flow cell sequence. The sequence initiation sequence can be complementary to a primer for sequencing. The primer can be a sequence specific primer or a universal primer. Such sequencing initiation sequences may be situated on single-stranded portions of the library adaptors. As an alternative, such sequencing initiation sequences may be priming sites (e.g., kinks or nicks) to permit a polymerase to couple to the library adaptors during sequencing.

In some cases, partial or complete sequencer motifs are provided by sequencing adaptors. A sequencing adaptor can include a sample molecular barcode and a sequencer motif. The sequencing adaptors can be provided in a set that is separate from the library adaptors. The sequencing adaptors in a given set can be identical—i.e., they contain the same sample barcode and sequencer motif.

Sequencing adaptors can include sample identification motifs and sequencer motifs. Sequencer motifs can include primers that are complementary to a sequencing initiation sequence. In some cases, sequencer motifs also include flow cell sequences or other sequences that permit a polynucleotide to a configured or arranged in a manner that permits the polynucleotide to be sequenced by a sequencer.

Library adaptors and sequencing adaptors can each be partial adaptors, that is, containing part but not all of the sequences necessary to enable sequencing by a sequencing platform. Together they provide complete adaptors. For example, library adaptors can include partial or no sequencer motifs, but such sequencer motifs are provided by sequencing adaptors.

Figure 9A:
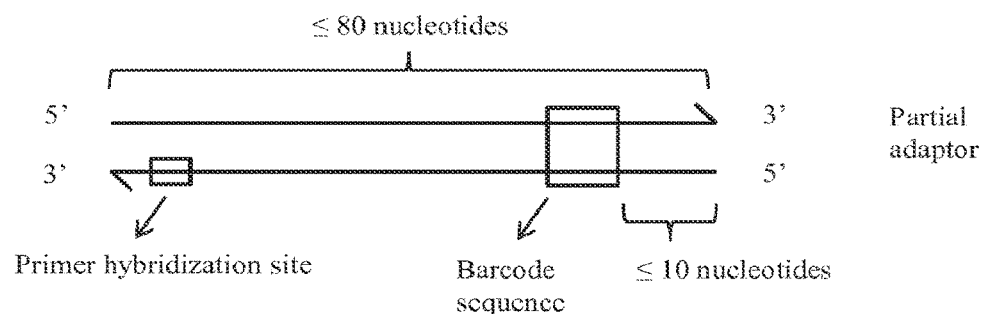
FIGS. 9A-9C schematically illustrate a method for tagging a polynucleotide molecule with a library adaptor and subsequently a sequencing adaptor.
Figure 9B:
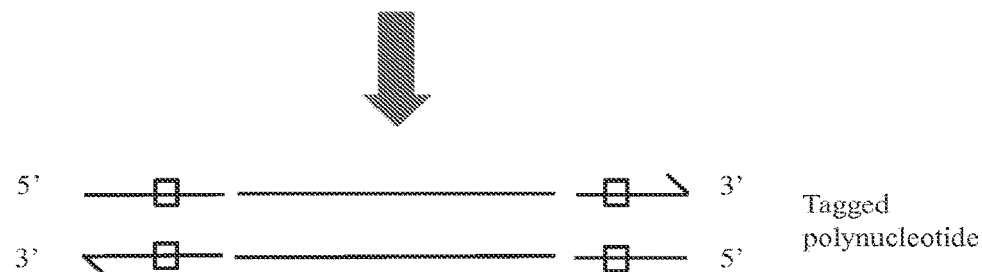
Figure 9C:
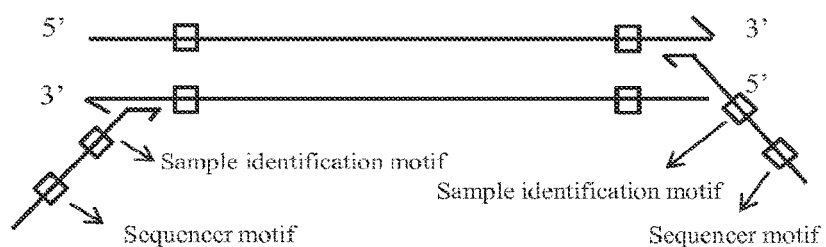

FIGS. 9A-9C schematically illustrate a method for tagging a target polynucleotide molecule with library adaptors. FIG. 9A shows a library adaptor as a partial adaptor containing a primer hybridization site on one of the strands and a molecular barcode towards another end. The primer hybridization site can be a sequencing initiation sequence for subsequent sequencing. The library adaptor is less than or equal to 80 nucleotide bases in length. In FIG. 9B, the library adaptors are ligated at both ends of the target polynucleotide molecule to provide a tagged target polynucleotide molecule. The tagged target polynucleotide molecule may be subjected to nucleic acid amplification to generate copies of the target. Next, in FIG. 9C, sequencing adaptors containing sequencer motifs are provided and hybridized to the tagged target polynucleotide molecule. The sequencing adaptors contain sample identification motifs. The sequencing adaptors can contain sequences to permit sequencing of the tagged target with a given sequencer.

D. Sequencing

Tagged polynucleotides can be sequenced to generate sequence reads (e.g., as shown in step (106), FIG. 1). For example, a tagged duplex polynucleotide can be sequenced. Sequence reads can be generated from only one strand of a tagged duplex polynucleotide. Alternatively, both strands of a tagged duplex polynucleotide can generate sequence reads. The two strands of the tagged duplex polynucleotide can comprise the same tags. Alternatively, the two strands of the tagged duplex polynucleotide can comprise different tags. When the two strands of the tagged duplex polynucleotide are differently tagged, sequence reads generated from one strand (e.g., a Watson strand) can be distinguished from sequence reads generated from the other strands (e.g., a Crick strand). Sequencing can involve generating multiple sequence reads for each molecule. This occurs, for example, as a result the amplification of individual polynucleotide strands during the sequencing process, e.g., by PCR.

Methods disclosed herein can comprise amplifying of polynucleotides. Polynucleotides amplification can result in the incorporation of nucleotides into a nucleic acid molecule or primer thereby forming a new nucleic acid molecule complementary to a template nucleic acid. The newly formed polynucleotide molecule and its template can be used as templates to synthesize additional polynucleotides. The polynucleotides being amplified can be any nucleic acids, for example, deoxyribonucleic acids, including genomic DNAs, cDNAs (complementary DNA), cfDNAs, and circulating tumor DNAs (ctDNAs). The polynucleotides being amplified can also be RNAs. As used herein, one amplification reaction may comprise many rounds of DNA replication. DNA amplification reactions can include, for example, polymerase chain reaction (PCR). One PCR reaction may comprise 2-100 "cycles" of denaturation, annealing, and synthesis of a DNA molecule. For example, 2-7, 5-10, 6-11, 7-12, 8-13, 9-14, 10-15, 11-16, 12-17, 13-18, 14-19, or 15-20 cycles can be performed during the amplification step. The condition of the PCR can be optimized based on the GC content of the sequences, including the primers.

Nucleic acid amplification techniques can be used with the assays described herein. Some amplification techniques are the PCR methodologies which can include, but are not limited to, solution PCR and in situ PCR. For example, amplification may comprise PCR-based amplification. Alternatively, amplification may comprise non PCR-based amplification. Amplification of the template nucleic acid may comprise use of one or more polymerases. For example, the polymerase may be a DNA polymerase or an RNA polymerase. In some cases, high fidelity amplification is performed such as with the use of high fidelity polymerase (e.g., Phusion® High-Fidelity DNA Polymerase) or PCR protocols. In some cases, the polymerase may be a high fidelity polymerase. For example, the polymerase may be KAPA HiFi DNA polymerase. The polymerase may also be Phusion DNA polymerase. The polymerase may be used under reaction conditions that reduce or minimize amplification biases, e.g., due to fragment length, GC content, etc.

Amplification of a single strand of a polynucleotide by PCR will generate copies both of that strand and its complement. During sequencing, both the strand and its complement will generate sequence reads. However, sequence reads generated from the complement of, for example, the Watson strand, can be identified as such because they bear the complement of the portion of the duplex tag that tagged the original Watson strand. In contrast, a sequence read generated from a Crick strand or its amplification product will bear the portion of the duplex tag that tagged the original Crick strand. In this way, a sequence read generated from an amplified product of a complement of the Watson strand can be distinguished from a complement sequence read generated from an amplification product of the Crick strand of the original molecule.

All amplified polynucleotides can be submitted to a sequencing device for sequencing. Alternatively, a sampling, or subset, of all of the amplified polynucleotides is submitted to a sequencing device for sequencing. With respect to any original double-stranded polynucleotide there can be three results with respect to sequencing. First, sequence reads can be generated from both complementary strands of the original molecule (that is, from both the Watson strand and from the Crick strand). Second, sequence reads can be generated from only one of the two complementary strands (that is, either from the Watson strand or from the Crick strand, but not both). Third, no sequence read may be generated from either of the two complementary strands. Consequently, counting unique sequence reads mapping to a genetic locus will underestimate the number of double-stranded polynucleotides in the original sample mapping to the locus. Described herein are methods of estimating the unseen and uncounted polynucleotides.

The sequencing method can be massively parallel sequencing, that is, simultaneously (or in rapid succession) sequencing any of at least 100, 1000, 10,000, 100,000, 1 million, 10 million, 100 million, or 1 billion polynucleotide molecules. Sequencing methods may include, but are not limited to: high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Maxam-Gilbert or Sanger sequencing, primer walking, sequencing using PacBio, SOLiD, Ion Torrent, or Nanopore platforms and any other sequencing methods known in the art.

Figure 4A:
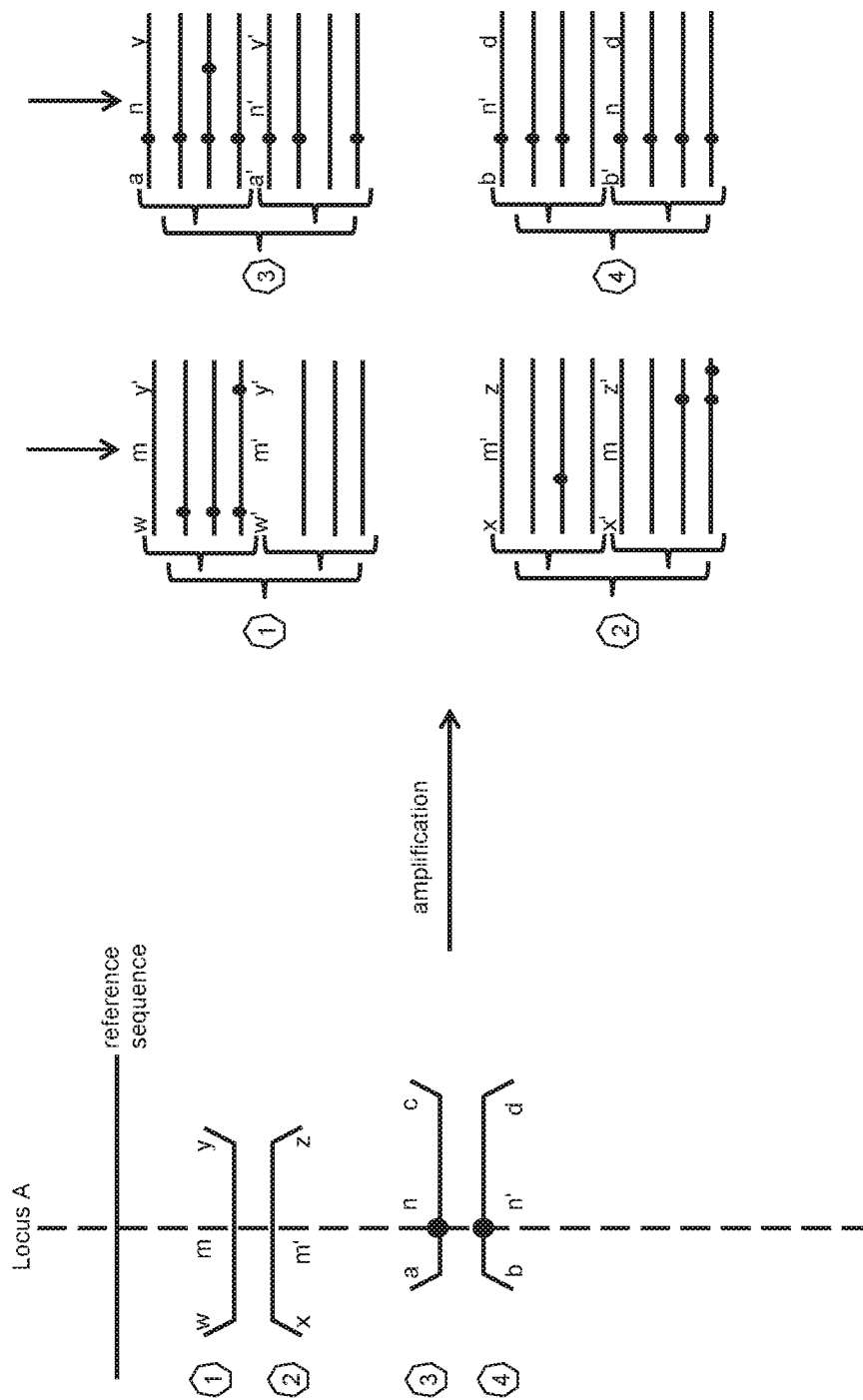
FIGS. 4A-C shows amplification, sequencing, redundancy reduction and pairing of complementary molecules.
Figure 4B:
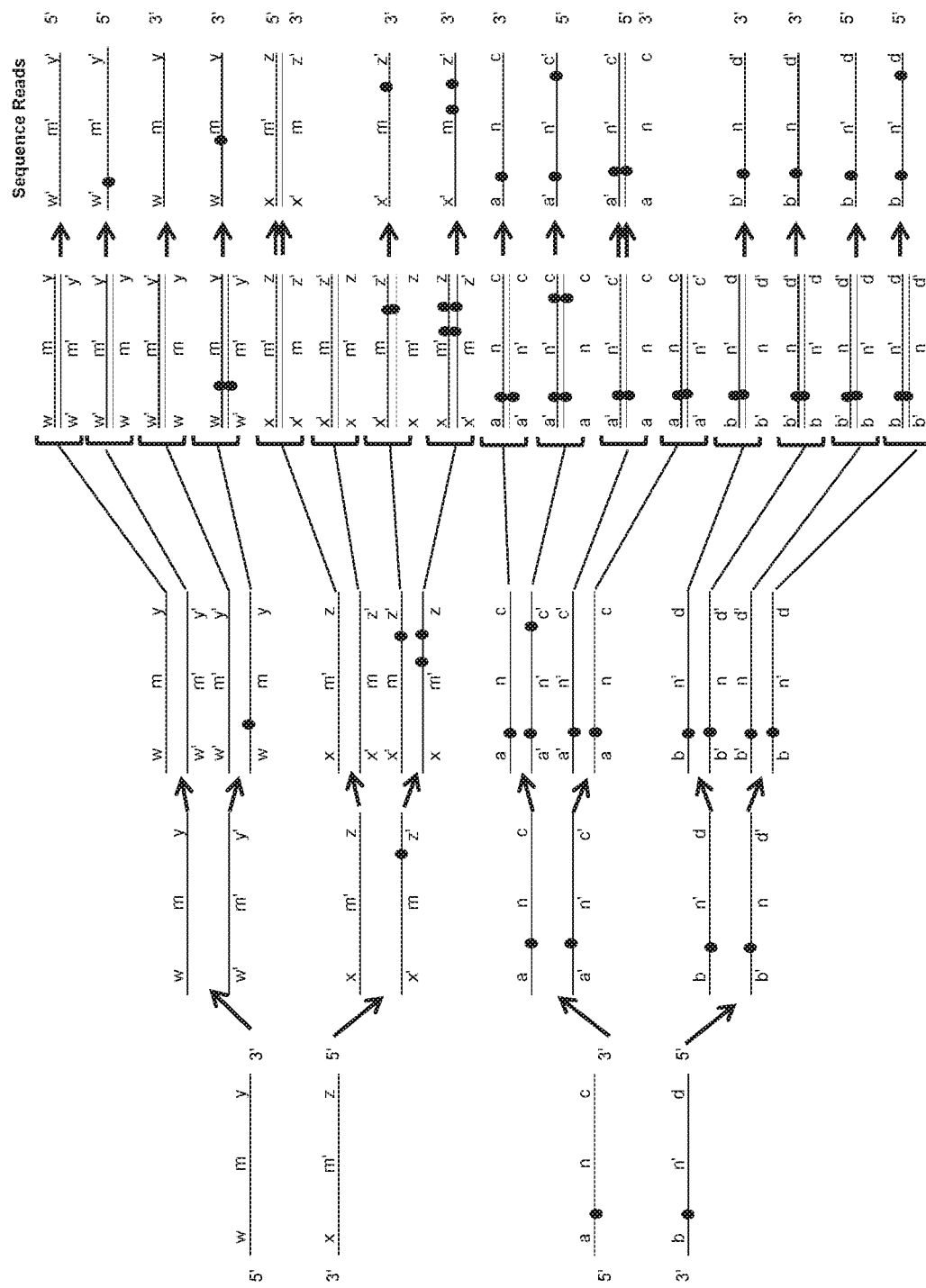

For example, duplex-tagged polynucleotides can be amplified, by for example PCR (see e.g., FIG. 4A duplex-tagged polynucleotides are referred to as mm' and nn'). In FIG. 4A, the strand of the duplex polynucleotide including sequence m bears sequence tags w and y, while the strand of the duplex polynucleotide including sequence m' bears sequence tags x and z. Similarly, the strand of the duplex polynucleotide including sequence n bears sequence tags a and c, while the strand of the duplex polynucleotide including sequence n' bears sequence tags b and d. During amplification, each strand produces itself and its complementary sequence. However, for example, an amplification progeny of original strand m that includes the complementary sequence, m', is distinguishable from an amplification progeny of original strand m' because the progeny from original strand m will have the sequence 5'-y'm'w'-3' and the progeny of the original m' strand one strand will have the sequence 5'-zm'x-3'. FIG. 4B shows amplification in more detail. During amplification, errors can be introduced into the amplification progeny, represented by dots. The application progeny are sampled for sequencing, so that not all strands produce sequence reads, resulting in the sequence reads indicated. Because sequence reads can come from either of a strand or its complement, both sequences and complement sequences will be included in the set of sequence reads. It should be noted that it is possible that a polynucleotide would bear the same tag on each end. Thus, for a tag "a", and polynucleotide "m", a first strand could be tagged a-m-a', and the complement could be tagged a-m'-a.

E. Determining Consensus Sequence Reads

Methods disclosed herein can comprise determining consensus sequence reads in sequence reads (e.g., as shown in step (108), FIG. 1), such as by reducing or tracking redundancy. Sequencing of amplified polynucleotides can produce reads of the several amplification products from the same original polynucleotide, referred to as "redundant reads". By identifying redundant reads, unique molecules in the original sample can be determined. If the molecules in a sample are uniquely tagged, then reads generated from amplification of a single unique original molecule can be identified based on their distinct barcode. Ignoring barcodes, reads from unique original molecules can be determined based on sequences at the beginning and end of a read, optionally in combination with the length of the read. In certain cases, however, a sample may be expected to have a plurality of original molecules having the same start stop sequences and the same length. Without barcoding, these molecules are difficult to distinguish from one another. However, if a collection of polynucleotides is non-uniquely tagged (that is, an original molecule shares the same identifier with at least one other original molecule), combining information from a barcode with start/stop sequence and/or polynucleotide length significantly increases the probability that any sequence read can be traced back to an original polynucleotide. This is because, in part, even without unique tagging, it is unlikely that any two original polynucleotides having the same start/stop sequence and length also will be tagged with the same identifier.

F. Collapsing

Collapsing allows for reduction in noise (i.e., background) that is generated at each step of the process. Methods disclosed herein can comprise collapsing, e.g., generating a consensus sequence by comparing multiple sequence reads. For example, sequence reads generated from a single original polynucleotide can be used to generate a consensus sequence of that original polynucleotide. Iterative rounds of amplification can introduce errors into progeny polynucleotides. Also, sequencing typically may not be performed with perfect fidelity so sequencing errors are introduced at this stage as well. However, comparison of sequence reads of molecules derived from a single original molecule, including those that have sequence variants, can be analyzed so as to determine the original, or "consensus" sequence. This can be done phylogenetically. Consensus sequences can be generated from families of sequence reads by any of a variety of methods. Such methods include, for example, linear or non-linear methods of building consensus sequences (such as voting (e.g., biased voting), averaging, statistical, maximum a posteriori or maximum likelihood detection, dynamic programming, Bayesian, hidden Markov or support vector machine methods, etc.) derived from digital communication theory, information theory, or bioinformatics. For example, if all or most of the sequence reads tracking back to an original molecule bear the same sequence variant, that variant probably existed in the original molecule. On the other hand, if a sequence variant exists in a subset of redundant sequence reads, that variant may have been introduced during amplification/sequencing and represents an artifact not existing in the original. Furthermore, if only sequence reads derived from the Watson or Crick strand of an original polynucleotide contain the variant, the variant may have been introduced through single-sided DNA damage, first-cycle PCR error or through contaminating polynucleotides that were amplified from a different sample.

After fragments are amplified and the sequences of amplified fragments are read and aligned, the fragments are subjected to base calling, e.g., determining for each locus the most likely nucleotide. However, variations in the number of amplified fragments and unseen amplified fragments (e.g., those without being read their sequences; reasons could be too many such as amplification errors, sequencing reading errors, too long, too short, being chopped, etc.) may introduce errors in base calling. If there are too many unseen amplified fragments with respect to the seen amplified fragments (amplified fragments actually being read), the reliability of base calling may be diminished.

Therefore, disclosed herein is a method to correct for the number of unseen fragments in base calling. For example, when base calling for locus A (an arbitrary locus), it is first assumed that there are N amplified fragments. The sequence readouts can come from two types of fragments: double-strand fragments and single-strand fragments. Therefore, we assign N1, N2, and N3 as the numbers of double-strands, single-strands, and unseen fragments, respectively. Thus, N=N1+N2+N3 (N1 and N2 are known from the sequence readouts, and N and N3 are unknown). If the formula is solved for N (or N3), then N3 (or N) will be inferred.

Probability is used to estimate N. For example, we assign "p" to be the probability of having detected (or having read) a nucleotide of locus A in a sequence readout of a single-strand.

For sequence readouts from double-strands, the nucleotide call from a double-strand amplified fragment has a probability of $p*p=p^2$, seeing all N1 double-strands has the following equation: $N1=N*(p^2)$.

For sequence readouts from a single-strand. Assuming that one of the 2 strands is seen, and the other is unseen, the probability of seeing one strand is "p", but the probability of missing the other strand is (1−p). Furthermore, by not distinguishing the single strand sourcing from 5-primer and sourcing from 3-primer, there is a factor of 2. Therefore, the nucleotide call from a single-strand amplified fragment has a probability 2×p×(1−p). Thus, seeing all N2 single-strands has the following equation: N2=N×2×p×(1−p).

"p" is also unknown. To solve p, the ratio of N1 to N2 is used to solve for "p":

$$R=N1/N2=Np^2/2Np(1-p)=p^2/2p(1-p)=p/2(1-p)$$

Once "p" is found, N can be found. After N is found, can be found N3=N−N1−N2.

Besides the ratio of paired versus unpaired strands (which is a measure post-collapsing), there is useful information in the pre-collapsing read depth at each locus. This information can be used to further improve the call for total molecule count and/or increase confidence of calling variants.

Figure 4C:
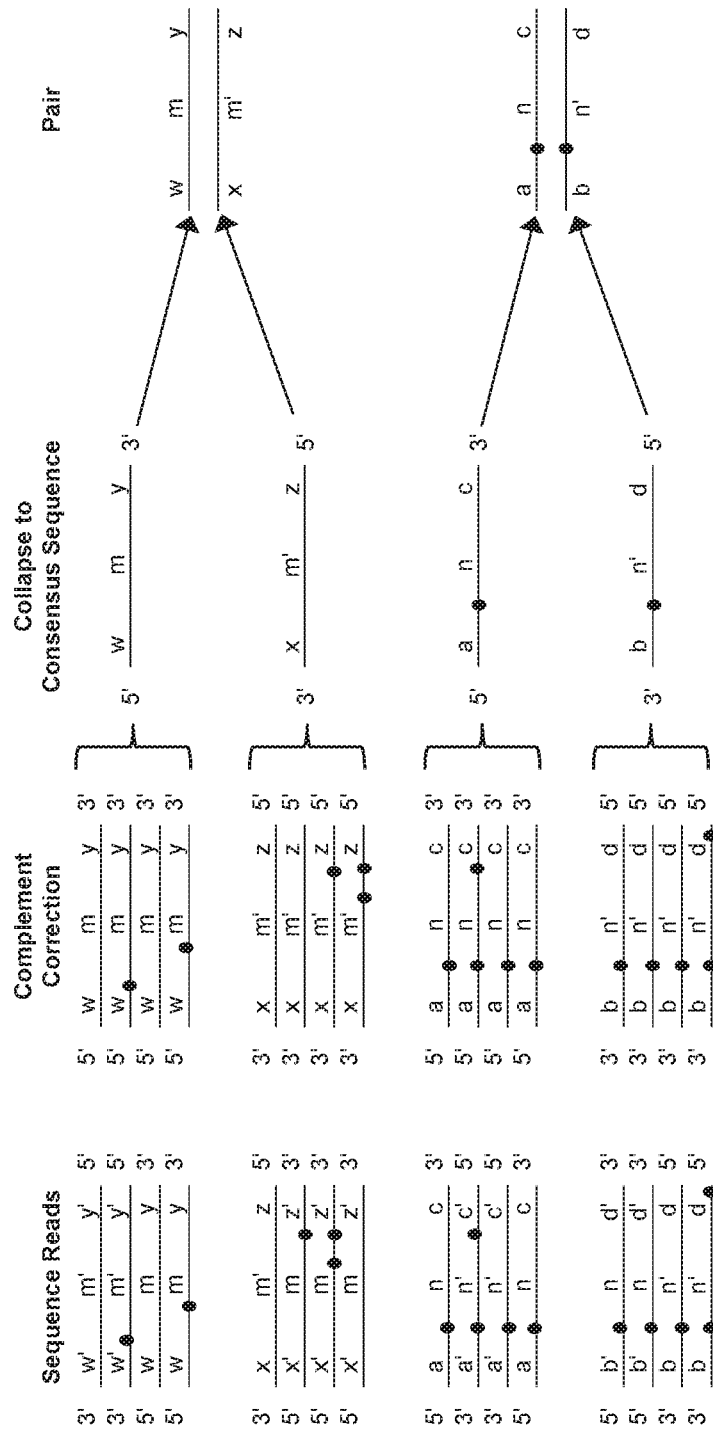

For example, FIG. 4C demonstrates sequence reads corrected for complementary sequences. Sequences generated from an original Watson strand or an original Crick strand can be differentiated on the basis of their duplex tags. Sequences generated from the same original strand can be grouped. Examination of the sequences can allow one to infer the sequence of the original strand (the "consensus sequence"). In this case, for example, the sequence variant in the nn' molecule is included in the consensus sequence because it included in every sequence read while other variants are seen to be stray errors. After collapsing sequences, original polynucleotide pairs can be identified based on their complementary sequences and duplex tags.

Figure 5:
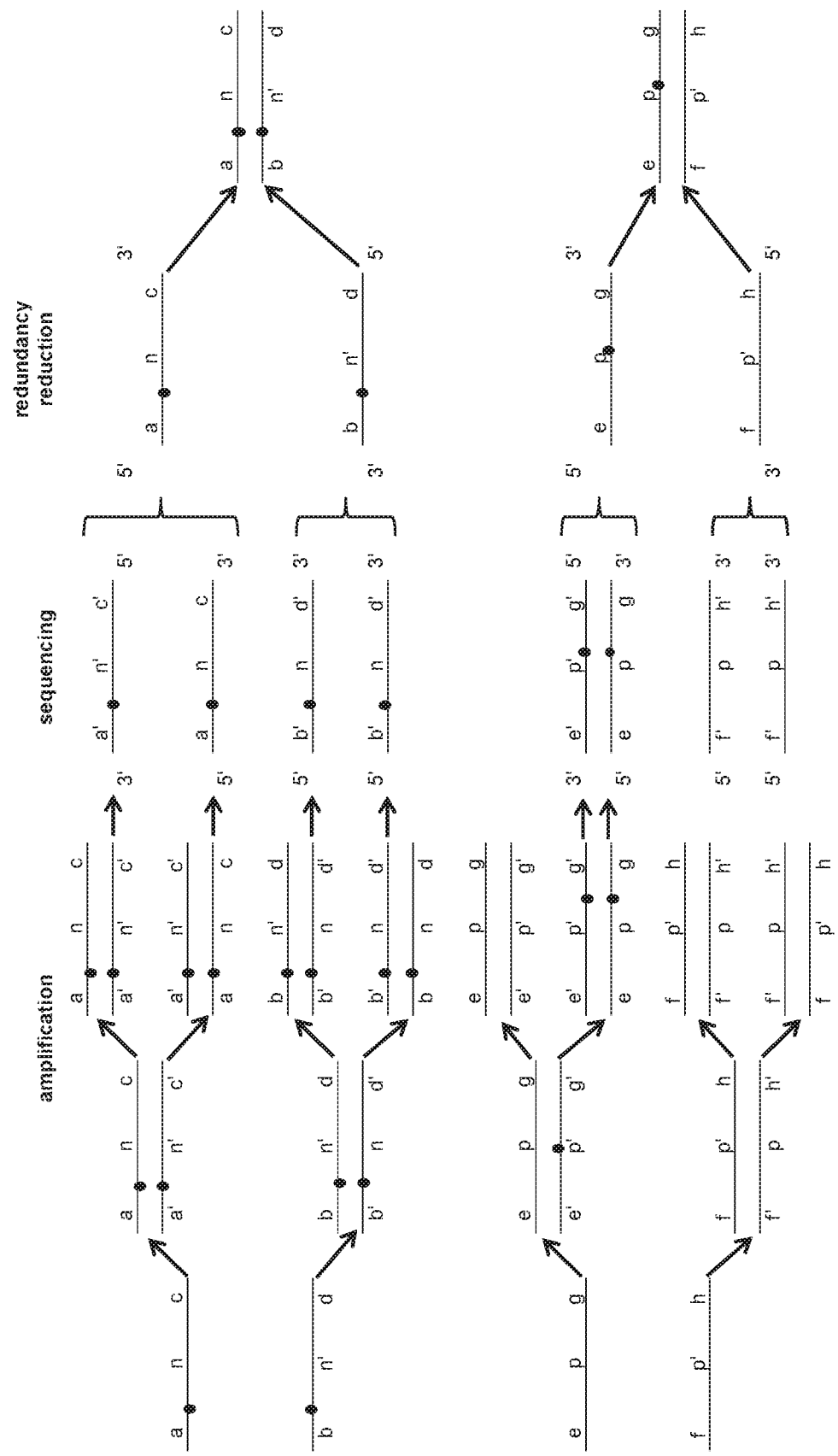
FIG. 5 shows increased confidence in detecting sequence variants by pairing reads from Watson and Crick strands.

FIG. 5 demonstrates increased confidence in detecting sequence variants by pairing reads from Watson and Crick strands. Sequence nn' can include a sequence variant indicated by a dot. In some cases, sequence pp' does not include a sequence variant. Amplification, sequencing, redundancy reduction and pairing can result in both Watson and Crick strands of the same original molecule including the sequence variant. In contrast, as a result of errors introduced during amplification and sampling during sequencing, the consensus sequence of the Watson strand p can contain a sequence variant, while the consensus sequence of the Crick strand p' does not. It is less likely that amplification and sequencing will introduce the same variant into both strands (nn' sequence) of a duplex than onto one strand (pp' sequence). Therefore, the variant in the pp' sequence is more likely to be an artifact, and the variant in the nn' sequence is more likely to exist in the original molecule.

Methods disclosed herein can be used to correct errors resulted from experiments, e.g., PCR, amplification, and/or sequencing. For example, such a method can comprises attaching one or more double stranded adaptors to both ends of a double stranded polynucleotide, thereby providing a tagged double stranded polynucleotide; amplifying the double stranded tagged polynucleotide; sequencing both strands of the tagged polynucleotide; comparing the sequence of one strand with its complement to determine any errors introduced during sequencing; and correcting errors in the sequence based on (d). The adaptors used in this method can be any adaptors disclosed herein, e.g., Y-shaped adaptors. The adaptor can comprise any barcodes (e.g., distinct barcodes) disclosed herein.

G. Mapping

Sequence reads or consensus sequences can be mapped to one or more selected genetic loci (e.g., as shown step (110), FIG. 1). A genetic locus can be, for example, a specific nucleotide position in the genome, a sequence of nucleotides (for example, an open reading frame), a fragment of a chromosome, a whole chromosome, or an entire genome. A genetic locus can be a polymorphic locus. Polymorphic locus can be a locus at which sequence variation exists in the population and/or exists in a subject and/or a sample. A polymorphic locus can be generated by two or more distinct sequences coexisting at the same location of the genome. The distinct sequences can differ from one another by one or more nucleotide substitutions, a deletion/insertion, and/or a duplication of any number of nucleotides, generally a relatively small number of nucleotides, such as less than 50, 45, 40, 35, 30, 25, 24, 23, 22, 21, 20, 19, 18, 17, 16, 15, 14, 13, 12, 11, 10, 9, 8, 7, 6, 5, 4, 3, 2, or 1 nucleotide(s), among others. A polymorphic locus can be created by a single nucleotide position that varies within the population, e.g. a single nucleotide variation (SNV) or a single nucleotide polymorphism (SNP).

A reference genome for mapping can include the genome of any species of interest. Human genome sequences useful as references can include the hg19 assembly or any previous or available hg assembly. Such sequences can be interrogated using the genome browser available at genome.ucsc.edu/index.html. Other species genomes include, for example PanTro2 (chimp) and mm9 (mouse).

In methods disclosed herein, collapsing can be performed before or after mapping. In some aspects, collapsing can be performed before mapping. For example, sequence reads can be grouped into families based on their tags and one or more endogenous sequences, without regard to where the reads map in the genome. Then, the members of a family can be collapsed into a consensus sequence. The consensus sequence can be generated using any collapsing method disclosed herein. Then the consensus sequence can be mapped to locations in the genome. Reads mapped to a locus can be quantified (e.g., counted). Percentage of reads carrying a mutation at a locus can also be determined. Alternatively, collapsing can be performed after mapping. For example, all reads can first be mapped to the genome. Then the reads can be grouped into families based on their tags and one or more endogenous sequences. Since the reads have been mapped to the genome, consensus bases can be determined for each family at each locus. In other aspects, consensus sequence can be generated for one strand of a DNA molecule (e.g., for a Watson strand or a Crick strand). Mapping can be performed before or after the consensus sequence for one strand of the DNA molecule is determined. Numbers of Doublets and Singlets can be determined. These numbers can be used to calculate unseen molecules. For example, the unseen molecules can be calculated using the following equation: $N=D+S+U$; $D=Np(2)$, $S=N2pq$, where $p=1-q$, where p is the probability of seeing; q is the probability of missing a strand.

H. Grouping

Methods disclosed herein can also comprise grouping sequence reads. Sequence reads can be grouped based on various types of sequences, e.g., sequences of an oligonucleotide tag (e.g., a barcode), sequence of a polynucleotide fragments, or any combinations. For example, as shown in step (112) (FIG. 1), sequence reads can be grouped as follows: Sequence reads generated from a "Watson" strand and those generated from a "Crick" strand of a double-stranded polynucleotide in the sample are identifiable based on the duplex tags that they bear. In this way, a sequence read or consensus sequence from a Watson strand of a duplex polynucleotide can be paired with a sequence read or consensus sequence from its complementary Crick strand. Paired sequence reads are referred to as a "Pair".

Sequence reads for which no sequence read corresponding to a complementary strand can be found among the sequence reads are termed "Singlets".

Double-stranded polynucleotides for which a sequence read for neither of the two complementary strands has been generated are referred to as "Unseen" molecules.

I. Quantifying

Methods disclosed herein also comprise quantifying sequence reads. For example, as shown in step (114) (FIG. 1), Pairs and Singlets mapping to a selected genetic locus, or to each of a plurality of selected genetic loci, are quantified, e.g., counted.

The quantifying can comprise estimating number of polynucleotides in the sample (e.g., Pairs polynucleotides, Singlets polynucleotides, or Unseen polynucleotides. For example, as shown in step (116) (FIG. 1), the number of double-stranded polynucleotides in the sample for which no sequence reads were generated ("Unseen" polynucleotides) is estimated. The probability that a double strand polynucleotide generates no sequence reads can be determined based on the relative number of Pairs and Singlets at any locus. Using this probability, the number of Unseen polynucleotide can be estimated.

In step (118) an estimate for the total number of double-stranded polynucleotides in a sample mapping to a selected locus is the sum of the number of Pairs, the number of Singlets and the number of Unseen molecules mapping to the locus.

Figure 2:
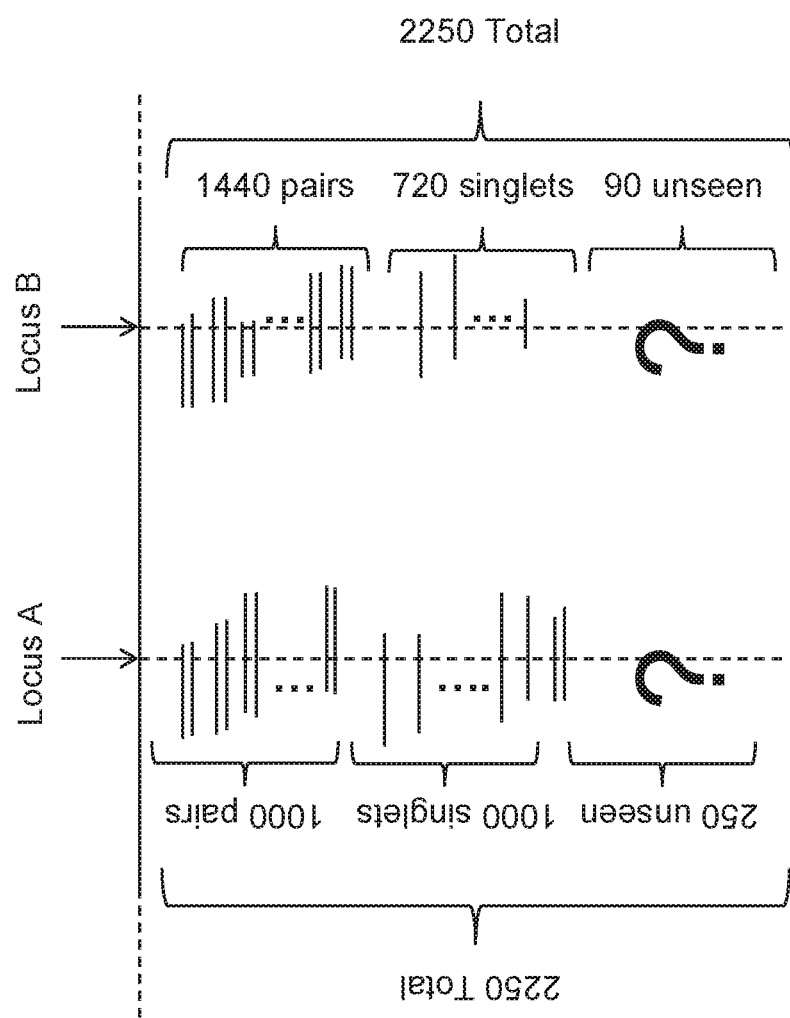
FIG. 2 depicts mapping of pairs and singlets to Locus A and Locus B in a genome.

The number of Unseen original molecules in a sample can be estimated based on the relative number of Pairs and Singlets (FIG. 2). Referring to FIG. 2, as an example, counts for a particular genomic locus, Locus A, are recorded, where 1000 molecules are paired and 1000 molecules are unpaired. Assuming a uniform probability, p, for an individual Watson or Crick strand to make it through the process subsequent to conversion, one can calculate the proportion of molecules that fail to make it through the process (Unseen) as follows: Let R=ratio of paired to unpaired molecules=1, so $R=1=p^2/(2p(1-p))$. This implies that $p=2/3$ and that the quantity of lost molecules is equal to $(1-p)^2=1/9$. Thus in this example, approximately 11% of converted molecules are lost and never detected. Consider another genomic locus, Locus B, in the same sample where 1440 molecules are paired and 720 are unpaired. Using the same method, we can infer the number of molecules that are lost, is only 4%. Comparing the two areas, it may be assumed that Locus A had 2000 unique molecules as compared to 2160 molecules in Locus B—a difference of almost 8%. However, by correctly adding in the lost molecules in each region, we infer there are $2000/(8/9)=2250$ molecules in Locus A and $2160/0.96=2250$ molecules in Locus B. Hence, the counts in both regions are actually equal. This correction and thus much higher sensitivity can be achievable by converting the original double-stranded nucleic acid molecules and bioinformatically keeping track of all those that are paired and unpaired at the end of the process. Similarly, the same procedure can be used to infer true copy number variations in regions that appear to have similar counts of observed unique molecules. By taking the number of unseen molecules into consideration in the two or more regions, the copy number variation becomes apparent.

In addition to using binomial distribution, other methods of estimating numbers of unseen molecules include exponential, beta, gamma or empirical distributions based on the redundancy of sequence reads observed. In the latter case, the distribution of read counts for paired and unpaired molecules can be derived from such redundancy to infer the underlying distribution of original polynucleotide molecules at a particular locus. This can often lead to a better estimation of the number of unseen molecules.

J. CNV Detection

Methods disclosed herein also comprise detecting CNV. For example, as shown in step (120) (FIG. 1), once the total number of polynucleotides mapping to a locus is determined, this number can be used in standard methods of determining CNV at the locus. A quantitative measure can be normalized against a standard. The standard can be an amount of any polynucleotides. In one method, a quantitative measure at a test locus can be standardized against a quantitative measure of polynucleotides mapping to a control locus in the genome, such as gene of known copy number. Quantitative measures can be compared against the amount of nucleic acid in any sample disclosed herein. For example, in another method, the quantitative measure can be compared against the amount of nucleic acid in the original sample. For example, if the original sample contained 10,000 haploid gene equivalents, the quantitative measure can be compared against an expected measure for diploidy. In another method, the quantitative measure can be normalized against a measure from a control sample, and normalized measures at different loci can be compared.

In some cases, in which copy number variation analysis is desired, sequence data may be: 1) aligned with a reference genome; 2) filtered and mapped; 3) partitioned into windows or bins of sequence; 4) coverage reads counted for each window; 5) coverage reads can then be normalized using a stochastic or statistical modeling algorithm; 6) and an output file can be generated reflecting discrete copy number states at various positions in the genome. In other cases, in which rare mutation analysis is desired, sequence data may be 1) aligned with a reference genome; 2) filtered and mapped; 3) frequency of variant bases calculated based on coverage reads for that specific base; 4) variant base frequency normalized using a stochastic, statistical or probabilistic modeling algorithm; 5) and an output file can be generated reflecting mutation states at various positions in the genome.

After the sequence read coverage ratios have been determined, a stochastic modeling algorithm can be optionally applied to convert the normalized ratios for each window region into discrete copy number states. In some cases, this algorithm may comprise a Hidden Markov Model. In other cases, the stochastic model may comprise dynamic programming, support vector machine, Bayesian modeling, probabilistic modeling, trellis decoding, Viterbi decoding, expectation maximization, Kalman filtering methodologies, or neural networks.

Methods disclosed herein can comprise detecting SNVs, CNVs, insertions, deletions, and/or rearrangements at a specific region in a genome. The specific genomic region can comprise a sequence in a gene, such as ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDHL IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, or NTRK1.

In some cases, the method uses a panel which comprises exons of one or more genes. The panel can comprise introns of one or more genes as well. The panel can also comprise exons and introns of one or more genes. The one or more genes can be those disclosed above. The panel can comprise about 80,000 bases which cover a panel of genes. The panel can comprise about 1000, 2000, 3000, 4000, 5000, 10000, 15000, 20000, 25000, 30000, 35000, 40000, 45000, 50000, 55000, 60000, 65000, 70000, 75000, 80000, 85000, 90000, 95000, 100000, 105000, 110000, 115000, 120000, 125000, or more bases.

In some aspects, copy number of a gene can be reflected in the frequency of a genetic form of the gene in a sample. For example, in a healthy individual, no copy number variation is reflected in a variant in a gene in one chromosome (e.g., heterozygosity) being detected in about 50% of detected molecules in a sample. Also, in a healthy individual, duplication of a gene bearing a variant can be reflected in the variant being detected in about 66% of detected molecules in a sample. Accordingly, if the tumor burden in a DNA sample is 10%, the frequency of a somatic mutation in a gene in one chromosome of cancer cells, without CNV, can be about 5%. The converse can be true in the case of aneuploidy.

The methods disclosed herein can be used to determine whether a sequence variant is more likely present in the germ line level or resulted from a somatic cell mutation, e.g., in a cancer cell. For example, a sequence variant in a gene detected at levels arguably consistent with heterozygosity in the germ line is more likely the product of a somatic mutation if CNV is also detected in that gene. In some cases, to the extent we expect that a gene duplication in the germ line bears a variant consistent with genetic dose (e.g., 66% for trisomy at a locus), detection gene amplification with a sequence variant dose that deviates significantly from this expected amount indicates that the CNV is more likely present as a result of somatic cell mutation.

The methods disclosed herein can also be used to infer tumor heterogeneity in a situation in which sequence variants in two genes are detected at different frequencies. For example, tumor heterogeneity can be inferred when two genes are detected at different frequencies but their copy numbers are relatively equal. Alternatively, tumor homogeneity can be inferred when the difference in frequency between two sequence variants is consistent with difference in copy number for the two genes. Thus, for example, if an EGFR variant is detected at 11% and a KRAS variant is detected at 5%, and no CNV is detected at these genes, the difference in frequency likely reflects tumor heterogeneity (e.g., all tumor cells carry an EGFR mutant and half the tumor cells also carry a KRAS mutant). Alternatively, if the EGFR gene carrying the mutant is detected at 2-times normal copy number, one interpretation is a homogenous population of tumor cells, each cell carrying a mutant in the EGFR and KRAS genes, but in which the KRAS gene is duplicated.

In response to chemotherapy, a dominant tumor form can eventually give way through Darwinian selection to cancer cells carrying mutants that render the cancer unresponsive to the therapy regimen. Appearance of these resistance mutants can be delayed through methods of this invention. In one embodiment of this method, a subject is subjected to one or more pulsed therapy cycles, each pulsed therapy cycle comprising a first period during which a drug is administered at a first amount and a second cycle during which the drug is administered at a second, reduced amount. The first period can be characterized by a tumor burden detected above a first clinical level. The second period can be characterized by a tumor burden detected below a second clinical level. First and second clinical levels can be different in different pulsed therapy cycles. For example, the first clinical level can be lower in succeeding cycles. A plurality of cycles can include at least 2, 3, 4, 5, 6, 7, 8 or more cycles. For example, the BRAF mutant V600E may be detected in polynucleotides of a disease cell at an amount indicating a tumor burden of 5% in cfDNA. Chemotherapy can commence with dabrafenib. Subsequent testing can show that the amount of the BRAF mutant in the cfDNA falls below 0.5% or to undetectable levels. At this point, dabrafenib therapy can stop or be significantly curtailed. Further subsequent testing may find that DNA bearing the BRAF mutation has risen to 2.5% of polynucleotides in cfDNA. At this point, dabrafenib therapy can be re-started, e.g., at the same level as the initial treatment. Subsequent testing may find that DNA bearing the BRAF mutation has decreased to 0.5% of polynucleotides in cfDNA. Again, dabrafenib therapy can be stopped or reduced. The cycle can be repeated a number of times.

A therapeutic intervention can also be changed upon detection of the rise of a mutant form resistant to an original drug. For example, cancers with the EGFR mutation L858R respond to therapy with erlotinib. However, cancers with the EGFR mutation T790M are resistant to erlotinib. However, they are responsive to ruxolitinib. A method of this invention involves monitoring changes in tumor profile and changing a therapeutic intervention when a genetic variant associated with drug resistance rises to a predetermined clinical level.

Methods disclosed in this invention can comprise a method of detecting disease cell heterogeneity from a sample comprising polynucleotides from somatic cells and disease cells, the method comprising: a) quantifying polynucleotides in the sample bearing a sequence variant at each of a plurality of genetic loci; b) determining CNV at each of the plurality of genetic loci; different relative amounts of disease molecules at a locus, wherein the CNV indicates a genetic dose of a locus in the disease cell polynucleotides; c) determining a relative measure of quantity of polynucleotides bearing a sequence variant at a locus per genetic dose at the locus for each of a plurality of the loci; and d) comparing the relative measures at each of the plurality of loci, wherein different relative measures indicates tumor heterogeneity. In the methods disclosed herein, the genetic dose can be determined on a total molecule basis. For example, if there are 1× total molecules at a first locus, and 1.2× molecules mapped to a second locus, then the genetic dose is 1.2. Variants at this locus can be divided by 1.2. In some aspects, the method disclosed herein can be used to detect any disease cell heterogeneity, e.g., tumor cell heterogeneity. The methods can be used to detect disease cell heterogeneity from a sample comprising any types of polynucleotides, e.g., cfDNA, genomic DNA, cDNA, or ctDNA. In the methods, the quantifying can comprise, for example, determining the number or relative amount of the polynucleotides. Determining CNV can comprise mapping and normalizing different relative amounts of total molecules to a locus.

In another aspect, in response to chemotherapy, a dominant tumor form can eventually give way through Darwinian selection to cancer cells carrying mutants that render the cancer unresponsive to the therapy regimen. Appearance of these resistance mutants can be delayed through methods disclosed throughout. The methods disclosed herein can comprise a method comprising: a) subjecting a subject to one or more pulsed therapy cycles, each pulsed therapy cycle comprising (i) a first period during which a drug is administered at a first amount and (ii) a second period during which the drug is administered at a second, reduced amount; wherein (A) the first period is characterized by a tumor burden detected above a first clinical level; and (B) the second period is characterized by a tumor burden detected below a second clinical level.

K. Sequence Variant Detection

Systems and methods disclosed herein can be used to detect sequence variants, e.g., SNVs. For example, a sequence variant can be detected from consensus sequences from multiple sequence reads, for example, from at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000, at least 10000 or more sequence reads. A consensus sequence can be from sequence reads of a single strand polynucleotide. A consensus sequence can also be from sequence reads of one strand of a double-stranded polynucleotide (e.g., pairing reads). In an exemplary method, pairing reads allows one to identify with increased confidence the existence of a sequence variant in a molecule. For example, if both strands of a Pair include the same variant, one can be reasonably sure that the variant existed in the original molecule, as the chance that the same variant is introduced into both strands during amplification/sequencing is rare. In contrast, if only one strand of a Pair includes the sequence variant, this is more likely to be an artifact. Similarly, the confidence that a Singlet bearing a sequence variant existed in the original molecule is less than the confidence if the variant exists in a Duplex, as there is higher probability that the variant can be introduced once than twice during amplification/sequencing.

Other methods of copy number variation detection and the sequence variant detection are described in PCT/US2013/058061, which is entirely incorporated herein by reference.

Sequence reads can be collapsed to generate a consensus sequence, which can be mapped to a reference sequence to identify genetic variants, such as CNV or SNV. As an alternative, the sequence reads are mapped prior to or even without mapping. In such a case, the sequence reads can be individually mapped to the reference to identify a CNV or SNV.

Figure 3:
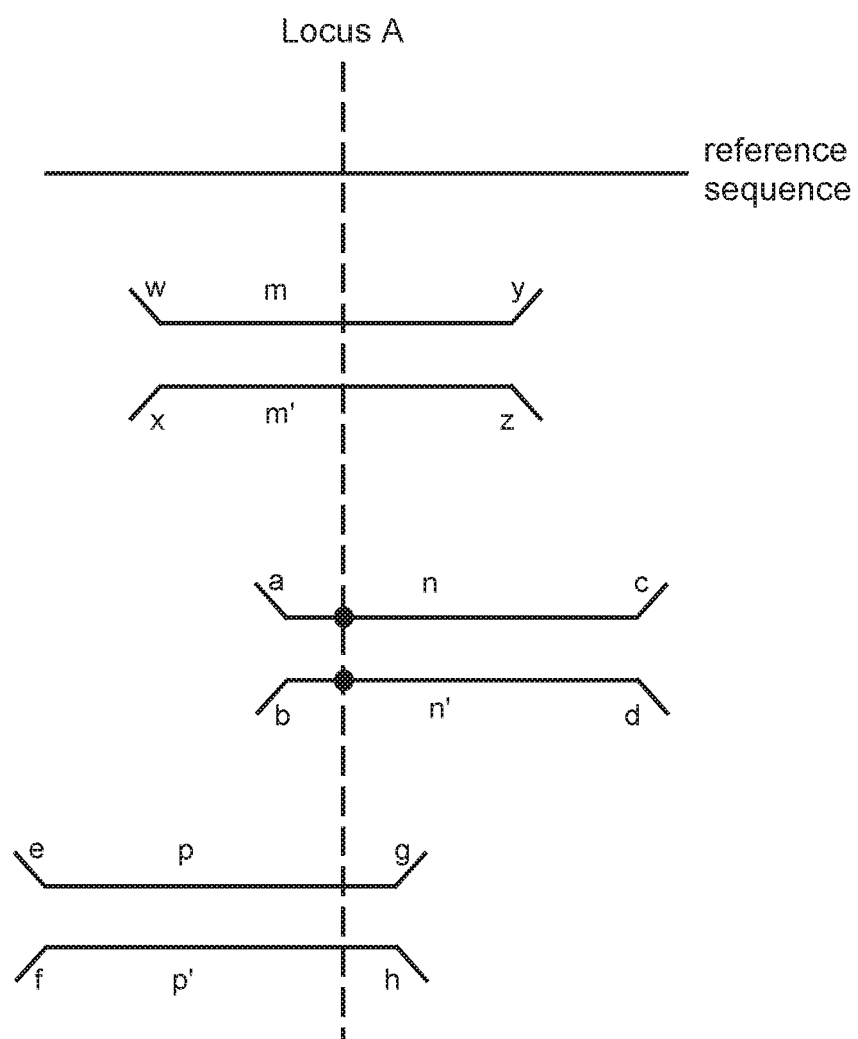
FIG. 3 shows a reference sequence encoding a genetic Locus A.

FIG. 3 shows a reference sequence encoding a genetic Locus A. The polynucleotides in FIG. 3 may be Y-shaped or have other shapes, such as hairpin.

In some cases, an SNV or multiple-nucleotide variant (MNV) can be determined across multiple sequence reads at a given locus (e.g., nucleotide base) by aligning sequence reads that correspond to that locus. Next, a plurality of sequential nucleotide bases from at least a subset of the sequence reads are mapped to the reference to a SNV or MNV in a polynucleotide molecule or portion thereof that corresponds to the reads. The plurality of sequential nucleotide bases can span an actual, inferred or suspected location of the SNV or MNV. The plurality of sequential nucleotide bases can span at least 3, 4, 5, 6, 7, 8, 9, or 10 nucleotide bases.

L. Detecting/Quantifying Nucleic Acids

The methods described throughout can be used to tag nucleic acids fragments, such as deoxyribonucleic acid (DNA), at extremely high efficiency. This efficient tagging allows a person to efficiently and accurately detect rare DNA in heterogenous populations of original DNA fragments (such as in cfDNA). A rare polynucleotide (e.g., rare DNA) can be a polynucleotide that comprises a genetic variant occurring in a population of polynucleotides at a frequency of less than 10%, 5%, 4%, 3%, 2%, 1%, or 0.1%. A rare DNA can be a polynucleotide with a detectable property at a concentration less than 50%, 25%, 10%, 5%, 1%, or 0.1%

Tagging can occur in a single reaction. In some cases, two or more reactions can be performed and pooled together. Tagging each original DNA fragments in a single reaction can result in tagging such that greater than 50% (e.g., 60%, 70%, 80%, 90%, 95%, or 99%) of the original DNA fragments are tagged at both ends with tags that comprise molecular barcodes, thereby providing tagged DNA fragments. Tagging can also result in greater than 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of the original DNA fragments tagged at both ends with tags that comprise molecular barcodes. Tagging can also result in 100% of the original DNA fragments tagged at both ends with tags that comprise molecular barcodes. Tagging can also result in single end tagging.

Tagging can also occur by using an excess amount of tags as compared to the original DNA fragments. For example, the excess can be at least 5-fold excess. In other cases, the excess can be at least 1.25, 1.5, 1.75, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more fold excess. Tagging can comprise attachment to blunt ends or sticky ends. Tagging can also be performed by hybridization PCR. Tagging can also be performed in low reaction volumes, such as 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 pico- and/or microliters.

The method can also include performing high fidelity amplification on the tagged DNA fragments. Any high fidelity DNA polymerases can be used. For example, the polymerase may be KAPA HiFi DNA polymerase or Phusion DNA polymerase.

Further, the method can comprise selectively enriching a subset of the tagged DNA fragments. For example, selective enrichment can be performed by hybridization or amplification techniques. The selective enrichment can be performed using a solid support (e.g., beads). The solid support (e.g., beads) can comprise probes (e.g., oligonucleotides specifically hybridizing to certain sequences. For example, the probes can hybridize with certain genomic regions, e.g., genes. In some cases, the genomic regions, e.g., genes, can be regions associated with diseases, e.g., cancer. After enrichment, the selected fragmented can be attached any sequencing adaptor disclosed in this invention. For example, a sequence adaptor can comprise a flow cell sequence, a sample barcode, or both. In another example, a sequence adaptor can be a hairpin shaped adaptor and/or comprises a sample barcode. Further, the resulting fragments can be amplified and sequenced. In some cases, the adaptor does not comprise a sequencing primer region.

The method can include sequencing one or both strands of the DNA fragments. In one case, both strands of the DNA fragment are independently sequenced. The tagged, amplified, and/or selectively enriched DNA fragments are sequenced to obtain sequence reads that comprise sequence information of the molecular barcodes and at least a portion of the original DNA fragments.

The method can include reducing or tracking redundancy (as described above) in the sequence reads to determine consensus reads that are representative of single-strands of the original DNA fragments. For example, to reduce or track redundancy, the method can include comparing sequence reads having the same or similar molecular barcodes and the same or similar end of fragment sequences. The method can comprise performing a phylogentic analysis on the sequence reads having the same or similar molecular barcodes. The molecular barcodes can have a barcode with varying edit distances (including any edit distances as described throughout), for example, an edit distance of up to 3. The end of the fragment sequences can include fragment sequences having an edit distance with varying distances (including any edit distances as described throughout), for example, an edit distance of up to 3.

The method can comprise binning the sequence reads according to the molecular barcodes and sequence information. For example, binning the sequence reads according to the molecular barcodes and sequence information can be performed from at least one end of each of the original DNA fragments to create bins of single stranded reads. The method can further comprise in each bin, determining a sequence of a given original DNA fragment among the original DNA fragments by analyzing sequence reads.

In some cases, sequence reads in each bin can be collapsed to a consensus sequence and subsequently mapped to a genome. As an alternative, sequence reads can be mapped to a genome prior to binning and subsequently collapsed to a consensus sequence.

The method can also comprise sorting sequence reads into paired reads and unpaired reads. After sorting, the number of paired reads and unpaired reads that map to each of one or more genetic loci can be quantified.

The method can include quantifying the consensus reads to detect and/or quantify the rare DNA, which are described throughout. The method can comprise detecting and/or quantifying the rare DNA by comparing a number of times each base occurs at each position of a genome represented by the tagged, amplified, and/or enriched DNA fragments.

The method can comprise tagging the original DNA fragments in a single reaction using a library of tags. The library can include at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 50, at least 100, at least 500, at least 1000, at least 5000, at least 10000, or any number of tags as disclosed throughout. For example, the library of tags can include at least 8 tags. The library of tags can include 8 tags (which can generate 64 different possible combinations). The method can be conducted such that a high percentage of fragments, e.g., greater than 50% (or any percentages as described throughout) are tagged at both ends, wherein each of the tags comprises a molecular barcode.

M. Processing and/or Analyzing Nucleic Acids

The methods described throughout can be used for processing and/or analyzing a nucleic acid sample of a subject. The method can comprising exposing polynucleotide fragments of the nucleic acid sample to a plurality of polynucleotide molecules to yield tagged polynucleotide fragments. The plurality of polynucleotide molecules that can be used are described throughout the application.

For example, the plurality of polynucleotide molecules can be each less than or equal to 40 nucleic acid bases in length and have distinct barcode sequences with respect to at least 4 nucleic acid bases and an edit distance of at least 1, wherein each of the distinct barcode sequences is within 20 nucleic acid bases from a terminal end of a respective one of the plurality of polynucleotide molecules, and wherein the plurality of polynucleotide molecules are not sequencing adaptors.

The tagged polynucleotide fragments can be subjected to nucleic acid amplification reactions under conditions that yield amplified polynucleotide fragments as amplification products of the tagged polynucleotide fragments. After amplification, the nucleotide sequence of the amplified tagged polynucleotide fragments is determined. In some cases, the nucleotide sequences of the amplified tagged polynucleotide fragments are determined without the use of polymerase chain reaction (PCR).

The method can comprise analyzing the nucleotide sequences with a programmed computer processor to identify one or more genetic variants in the nucleotide sample of the subject. Any genetic alterations can be identified, including but not limited to, base change(s), insertion(s), repeat(s), deletion(s), copy number variation(s), epigenetic modification(s), nucleosome binding site(s), copy number change(s) due to origin(s) of replication, and transversion(s). Other genetic alterations can include, but are not limited to, one or more tumor associated genetic alterations.

The subject of the methods can be suspected of having a disease. For example, the subject can be suspected of having cancer. The method can comprise collecting a nucleic acid sample from a subject. The nucleic acid sample can be collected from blood, plasma, serum, urine, saliva, mucosal excretions, sputum, stool, cerebral spinal fluid, skin, hair, sweat, and/or tears. The nucleic acid sample can be a cell-free nucleic acid sample. In some cases, the nucleic acid sample is collected from no more than 100 nanograms (ng) of double-stranded polynucleotide molecules of the subject.

The polynucleotide fragments can comprise double-stranded polynucleotide molecules. In some cases, the plurality of polynucleotide molecules are coupled to the polynucleotide fragments via blunt end ligation, sticky end ligation, molecular inversion probes, polymerase chain reaction (PCR), ligation-based PCR, multiplex PCR, single strand ligation, or single strand circularization.

The method as described herein results in high efficiency tagging of nucleic acids. For example, exposing the polynucleotide fragments of the nucleic acid sample to the plurality of polynucleotide molecules yields the tagged polynucleotide fragments with a conversion efficiency of at least 30%, e.g., of at least 50% (e.g., 60%, 70%, 80%, 90%, 95%, or 99%). Conversion efficiency of at least 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% can be achieved.

The method can result in a tagged polynucleotide fragment that share common polynucleotide molecules. For example, any of at least 5%, 6%, 7%, 8%, 9%, 10%, 20%, 25%, 30%, 35%, 40%, 45%, 50%, 55%, 60%, 65%, 70%, 75%, 80%, 85%, 90%, 95%, 96%, 97%, 98%, 99% or 100% of the tagged polynucleotide fragments share a common polynucleotide molecule. The method can comprise generating the polynucleotide fragments from the nucleic acid sample.

In some cases, the subjecting of the method comprises amplifying the tagged polynucleotide fragments in the presence primers corresponding to a plurality of genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1. Additionally, any combination of these genes can be amplified. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or all 54 of these genes can be amplified.

The methods described herein can comprise generating a plurality of sequence reads from a plurality of polynucleotide molecules. The plurality of polynucleotide molecules can cover genomic loci of a target genome. For example, the genomic loci can correspond to a plurality of genes as listed above. Further, the genomic loci can be any combination of these genes. Any given genomic locus can comprise at least two nucleic acid bases. Any given genomic locus can also comprise a plurality of nucleic acid bases, for example, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more nucleic acid bases.

The method can comprise grouping with a computer processor the plurality of sequence reads into families. Each of the family can comprises sequence reads from one of the template polynucleotides. Each family can comprise sequence reads from only one of the template polynucleotides. For each of the family, the sequence reads can be merged to generate a consensus sequence. The grouping can comprise classifying the plurality of sequence reads into families by identifying (i) distinct molecular barcodes coupled to the plurality of polynucleotide molecules and (ii) similarities between the plurality of sequence reads, wherein each family includes a plurality of nucleic acid sequences that are associated with a distinct combination of molecular barcodes and similar or identical sequence reads.

Once merged, a consensus sequence can be called at a given genomic locus among the genomic loci. At any given genomic loci, any of the following can be determined: i) genetic variants among the calls; ii) frequency of a genetic alteration among the calls; iii) total number of calls; and iv) total number of alterations among the calls. The calling can comprise calling at least one nucleic acid base at the given genomic locus. The calling can also comprise calling a plurality of nucleic acid bases at the given genomic locus. In some cases, the calling can comprise phylogenetic analysis, voting (e.g., biased voting), weighing, assigning a probability to each read at the locus in a family, or calling the base with the highest probability. The consensus sequence can be generated by evaluating a quantitative measure or a statistical significance level for each of the sequence reads. If a quantitative measure is performed, the method can comprise use of a binomial distribution, exponential distribution, beta distribution, or empirical distribution. However, frequency of the base at the particular location can also be used for calling, for example, if 51% or more of the reads is a "A" at the location, then the base may be called an "A" at that particular location. The method can further comprise mapping a consensus sequence to a target genome.

The method can further comprising performing consensus calling at an additional genomic locus among the genomic loci. The method can comprise determining a variation in copy number at one of the given genomic locus and additional genomic locus based on counts at the given genomic locus and additional genomic locus.

The methods described herein can comprise providing template polynucleotide molecules and a library of adaptor polynucleotide molecules in a reaction vessel. The adaptor polynucleotide molecules can have from 2 to 1,000 different barcode sequences and in some cases are not sequencing adaptors. Other variations of adaptor polynucleotide molecules are described throughout, which can also be used in the methods.

The polynucleotide molecules of the adaptors can have the same sample tag. The adaptor polynucleotide molecules can be coupled to both ends of the template polynucleotide molecules. The method can comprise coupling the adaptor polynucleotide molecules to the template polynucleotide molecules at an efficiency of at least 30%, e.g., of at least 50% (e.g., 60%, 70%, 80%, 90%, 95%, or 99%), thereby tagging each template polynucleotide with a tagging combination that is among 4 to 1,000,000 different tagging combinations, to produce tagged polynucleotide molecules. In some cases, the reaction can occur in a single reaction vessel. Coupling efficiency can also be at least 30%, 35%, 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. Tagging can be non-unique tagging.

The tagged polynucleotide molecules can then be subject to an amplification reaction under conditions that will yield amplified polynucleotide molecules as amplification products of the tagged polynucleotide molecules. The template polynucleotide molecules can be double-stranded. Further, the template polynucleotide molecules can be blunt ended. In some cases, the amplification reaction comprises non-specifically amplifying the tagged polynucleotide molecules. The amplification reaction can also comprises using a priming site to amplify each of the tagged polynucleotide molecules. The priming site can be a primer, e.g., a universal primer. The priming site can also be a nick.

The method can also comprise sequencing the amplified polynucleotide molecules. The sequencing can comprise (i) subjecting the amplified polynucleotide molecules to an additional amplification reaction under conditions that yield additional amplified polynucleotide molecules as amplification products of the amplified polynucleotide molecules, and/or (ii) sequencing the additional amplified polynucleotide molecules. The additional amplification can be performed in the presence of primers comprising flow cells sequences, which will produce polynucleotide molecules that are capable of binding to a flow cell. The additional amplification can also be performed in the presence of primers comprising sequences for hairpin shaped adaptors. The hairpin shaped adaptors can be attached to both ends of a polynucleotide fragment to generate a circular molecule, which can be sequenced multiple times. The method can further comprise identifying genetic variants upon sequencing the amplified polynucleotide molecules.

The method can further comprising separating polynucleotide molecules comprising one or more given sequences from the amplified polynucleotide molecules, to produce enriched polynucleotide molecules. The method can also comprise amplifying the enriched polynucleotide molecules with primers comprising the flow cell sequences. This amplification with primers comprising flow cell sequences will produce polynucleotide molecules that are capable of binding to a flow cell. The amplification can also be performed in the presence of primers comprising sequences for hairpin shaped adaptors. The hairpin shaped adaptors can be attached to both ends of a polynucleotide fragment to generate a circular molecule, which can be sequenced multiple times.

Flow cell sequences or hairpin shaped adaptors can be added by non-amplification methods such as through ligation of such sequences. Other techniques such as hybridization methods can be used, e.g., nucleotide overhangs.

The method can be performed without aliquoting the tagged polynucleotide molecules. For example, once the tagged polynucleotide molecule is made, the amplification and sequencing can occur in the same tube without any further preparation.

The methods described herein can be useful in detecting single nucleotide variations (SNV), copy number variations (CNV), insertions, deletions, and/or rearrangements. In some cases, the SNVs, CNVs, insertions, deletions, and/or rearrangements, can be associated with disease, for example, cancer.

N. Monitoring a Patient's Status

Methods disclosed herein can also be used to monitor a patient's disease status. The disease of a subject can be monitored over time to determine a progression of the disease (e.g., regression). Markers indicative of the disease can be monitored in a biological sample of the subject, such as a cell-free DNA sample.

For example, monitoring a subject's cancer status can comprise (a) determining an amount of one or more SNVs or copy numbers of a plurality of genes (e.g., in an exon), (b) repeating such determination at different points in time, and (c) determining if there is a difference in the number of SNVs, level of SNVs, number or level of genomic rearrangements, or copy numbers between (a) and (b). The genes can be selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1. The genes can be selected from any 5, 10, 15, 20, 30, 40, 50, or all of the genes in this group.

O. Sensitivity and Specificity

Methods disclosed herein can be used to detect cancer polynucleotides in a sample, and cancer in a subject, with high measures of agreement, e.g., high sensitivity and/or specificity. For example, such methods can detect cancer polynucleotides (e.g., rare DNA) in a sample at a concentration that is less than 5%, 1%, 0.5%, 0.1%, 0.05%, or 0.01%, at a specificity of at least 99%, 99.9%, 99.99%, 99.999%, 99.9999%, or 99.99999%. Such polynucleotides may be indicative of cancer or other disease. Further, such methods can detect cancer polynucleotides in a sample with a positive predictive value of at least 90%, 91%, 92%, 93%, 94%, 95%, 96%, 97%, 98%, 99%, 99.9%, 99.99%, 99.999%, or 99.9999%.

Subjects identified as positive in a test that are in reality positive are referred as true positives (TP). Subjects identified as positive in a test that are in reality negative are referred as false positives (FP). Subjects identified as negative in a test that are in reality negative are referred as true negatives (TN). Subjects identified as negative in a test that are in reality positive are referred as false negatives (FN). Sensitivity is the percentage of actual positives identified in a test as positive. This includes, for example, instances in which one should have found a cancer genetic variant and did. (Sensitivity=TP/(TP+FN).) Specificity is the percentage of actual negatives identified in a test as negative. This includes, for example, instances in which one should have found no cancer genetic variant and did not. Specificity can be calculated using the following equation: Specificity=TN/(TN+FP). Positive predictive value (PPV) can be measured by the percentage of subjects who test positive that are true positives. PPV can be calculated using the following equation: PPV=TP/(TP+FP). Positive predictive value can be increased by increasing sensitivity (e.g., chance of an actual positive being detected) and/or specificity (e.g., chance of not mistaking an actual negative for a positive).

Low conversion rates of polynucleotides into adaptor-tagged polynucleotides can compromise sensitivity as it decreases the chance of converting, and therefore detecting, rare polynucleotide targets. Noise in a test can compromise specificity as it increases the number of false positives detected in a test. Both low conversion rate and noise compromise positive predictive value as they decrease the percentage of true positives and increase the percentage of false positives.

The methods disclosed herein can achieve high levels of agreement, e.g., sensitivity and specificity, leading to high positive predictive values. Methods of increasing sensitivity include high efficiency conversion of polynucleotides into adaptor-tagged polynucleotides in a sample. Methods of increasing specificity include reducing sequencing errors, for example, by molecular tracking.

Methods of the present disclosure can be used to detect genetic variation in non-uniquely tagged initial starting genetic material (e.g., rare DNA) at a concentration that is less than 5%, 1%, 0.5%, 0.1%, 0.05%, or 0.01%, at a specificity of at least 99%, 99.9%, 99.99%, 99.999%, 99.9999%, or 99.99999%. In some aspects, the methods can further comprise converting polynucleotides in the initial starting material at an efficiency of at least at least 10%, at least 20%, at least 30%, at least 40%, at least 50%, at least 60%, at least 70%, at least 80%, or at least 90%. Sequence reads of tagged polynucleotides can be subsequently tracked to generate consensus sequences for polynucleotides with an error rate of no more than 2%, 1%, 0.1%, or 0.01%.

2. Pooling Methods

Figure 8:
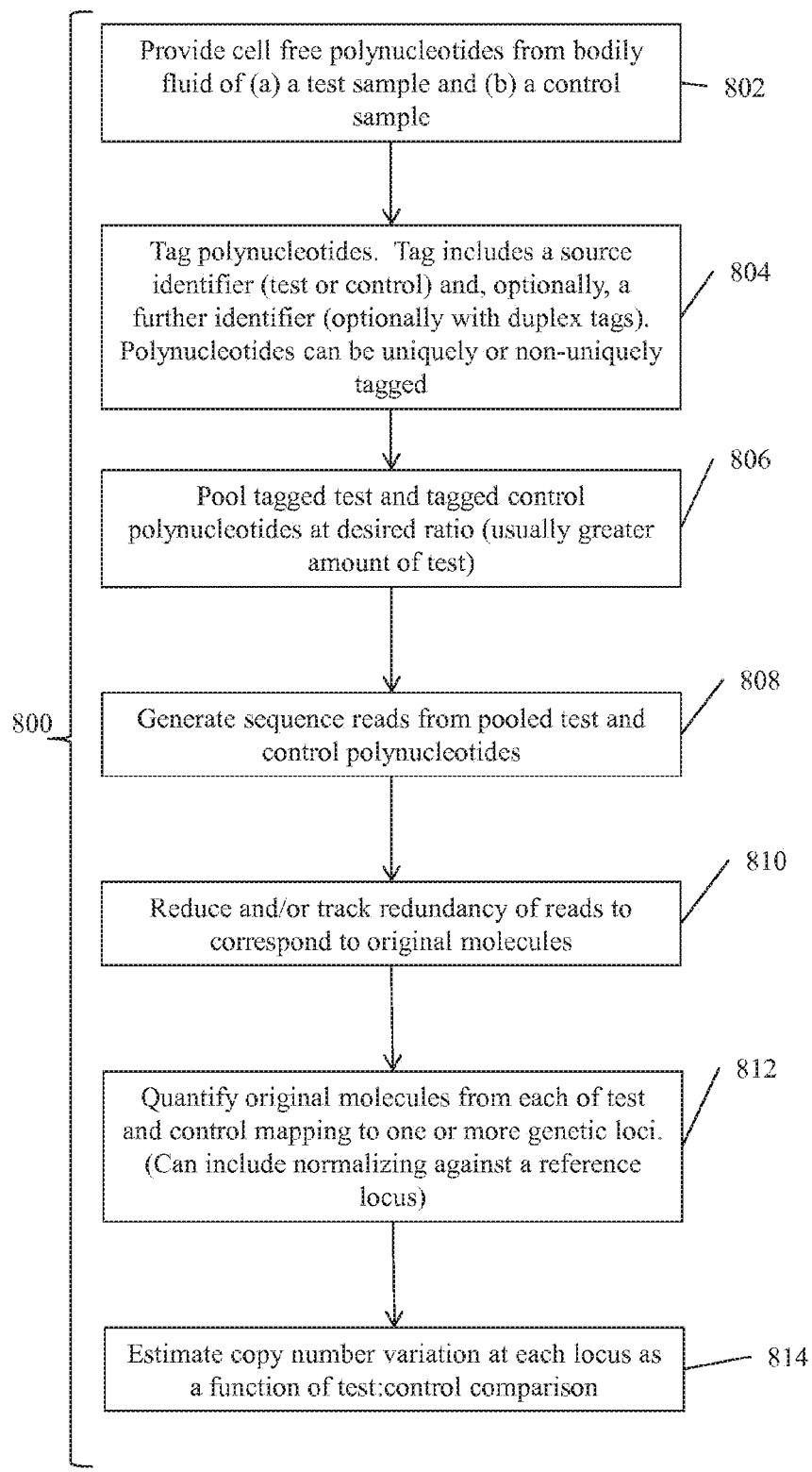
FIG. 8 is a flowchart representation of a method of this invention for determining CNV using pooled test and control pools.

Disclosed herein are methods of detecting copy number variation and/or sequence variants at one or more genetic loci in a test sample. One embodiment is shown in FIG. 8. Typically, detecting copy number variation involves determining a quantitative measure (e.g., an absolute or relative number) of polynucleotides mapping to a genetic locus of interest in a genome of a test sample, and comparing that number to a quantitative measure of polynucleotides mapping to that locus in a control sample. In certain methods, the quantitative measure is determined by comparing the number of molecules in the test sample that map to a locus of interest with a number of molecules in the test sample mapping to a reference sequence, e.g., a sequence expected to be present at wild type ploidy number. In some examples, the reference sequence is HG19, build 37, or build 38. The comparison could involve, for example, determining a ratio. Then, this measure is compared with a similar measure determined in a control sample. So, for example, if a test sample has a ratio of 1.5:1 for locus of interest versus reference locus, and a control sample has a ratio of 1:1 for the same loci, one may conclude that the test sample exhibits polyploidy at the locus of interest.

When the test sample and the control sample are analyzed separately, the work flow can introduce distortions between final numbers in the control and test samples.

In one method disclosed herein (e.g., flow chart 800), polynucleotides are provided from a test and a control sample (802). Polynucleotides in a test sample and those in a control sample are tagged with tags that identify the polynucleotides as originating from the test or control sample (a source tag). (804.) The tag can be, for example, a polynucleotide sequence or barcode that unambiguously identifies the source.

The polynucleotides in each of the control and test samples also can be tagged with identifier tags that will be carried by all amplification progeny of a polynucleotide. Information from start and end sequences of a polynucleotide and identifier tags can identify sequence reads from polynucleotides amplified from an original parent molecule. Each molecule can be uniquely tagged compared with other molecules in the sample. Alternatively, each molecule need not be uniquely tagged compared with other molecules in the sample. That is, the number of different identifier sequences can be fewer than that the number of molecules in sample. By combining identifier information with start/stop sequence information, the probability of confusing two molecules having the same start/stop sequence is significantly diminished.

Number of different identifiers used to tag a nucleic acid (e.g., cfDNA) can dependent on the number of different haploid genome equivalents. Different identifiers can be used to tag at least 2, least 10, least 100, least 200, least 300, least 400, least 500, least 600, least 700, least 800, least 900, least 1,000, least 2,000, least 3,000, least 4,000, least 5,000, least 6,000, least 7,000, least 8,000, least 9,000, least 10,000 or more different haploid genome equivalents. Accordingly, the number of different identifiers used to tag a nucleic acid sample, e.g., cell-free DNA from 500 to 10,000 different haploid genome equivalents and be between any of 1, 2, 3, 4 and 5 and no more than 100, 90, 80, 70, 60, 50, 40 or 30. For example, the number of different identifier used to tag a nucleic acid sample from 500 to 10,000 different haploid genome equivalents can be 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or less.

Polynucleotides can be tagged by ligation of adaptors comprising the tags or identifiers before amplification. Ligation can be performed using an enzyme, e.g., a ligase. For example, tagging can be performed using a DNA ligase. The DNA ligase can be a T4 DNA ligase, *E. coli* DNA ligase, and/or mammalian ligase. The mammalian ligase can be DNA ligase I, DNA ligase III, or DNA ligase IV. The ligase may also be a thermostable ligase. Tags can be ligated to a blunt-end of a polynucleotide (blunt-end ligation). Alternatively, tags can be ligated to a sticky end of a polynucleotide (sticky-end ligation). The polynucleotides can be tagged by blunt end ligation using adaptors (e.g., adaptors having forked ends). High efficiency of ligation can be achieved using high excess of adaptors (e.g., more than 1.5×, more than 2×, more than 3×, more than 4×, more than 5×, more than 6×, more than 7×, more than 8×, more than 9×, more than 10×, more than 11×, more than 12×, more than 13×, more than 14×, more than 15×, more than 20×, more than 25×, more than 30×, more than 35×, more than 40×, more than 45×, more than 50×, more than 55×, more than 60×, more than 65×, more than 70×, more than 75×, more than 80×, more than 85×, more than 90×, more than 95×, or more than 100).

Once tagged with tags that identify source of the polynucleotides, polynucleotides from different sources (e.g., different samples) can be pooled. After pooling, polynucleotides from different sources (e.g., different samples) can be distinguished by any measurement using the tags, including any process of quantitative measurement. For example, as shown in (806) (FIG. 8), polynucleotides from the control sample and the test sample can be pooled. The pooled molecules can be subject to the sequencing (808) and bioinformatic work flow. Both will be subject to the same variations in the process and, therefore, any differential bias is reduced. Because molecules originating from control and test samples are differently tagged, they can be distinguished in any process of quantitative measurement.

The relative amount of control and test sample pooled can be varied. The amount of control sample can be same as the amount of test sample. The amount of control sample can also be larger than the amount of test sample. Alternatively, the amount of control sample can be smaller than the amount of test sample. The smaller the relative amount of one sample to the total, the fewer identifying tags needed in the original tagging process. A number can be selected to reduce to acceptable levels the probability that two parent molecules having the same start/end sequences will bear the same identifying tag. This probability can be less than 10%, less than 1%, less than 0.1% or less than 0.01%. The probability can be less than 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%.

Methods disclosed herein can also comprise grouping sequence reads. For example, bioinformatic workflow can include grouping sequence reads produced from progeny of a single parent molecule, as shown in (810) (FIG. 8). This can involve any of the redundancy reduction methods described herein. Molecules sourced from test and control samples can be differentiated based on source tags they carry (812). Molecules mapping to a target locus are quantified for both test-sourced and control-sourced molecules (812). This can include the normalization methods discussed herein, e.g., in which numbers at a target locus are normalized against numbers at a reference locus.

Normalized (or raw) quantities at a target locus from test and control samples are compared to determine presence of copy number variation (814).

3. Computer Control Systems

Figure 6:
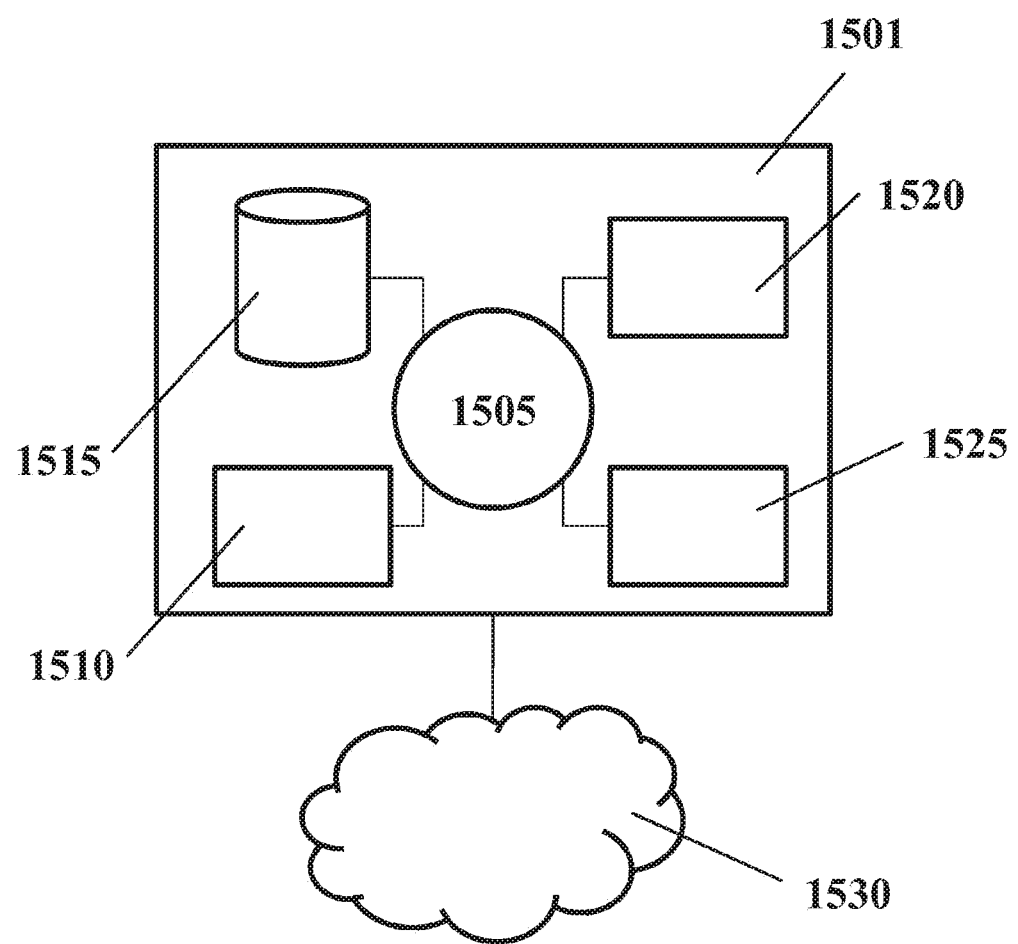
FIG. 6 shows a computer system that is programmed or otherwise configured to implement various methods of the present disclosure.

The present disclosure provides computer control systems that are programmed to implement methods of the disclosure. FIG. 6 shows a computer system 1501 that is programmed or otherwise configured to implement the methods of the present disclosure. The computer system 1501 can regulate various aspects sample preparation, sequencing and/or analysis. In some examples, the computer system 1501 is configured to perform sample preparation and sample analysis, including nucleic acid sequencing. The computer system 1501 can be an electronic device of a user or a computer system that is remotely located with respect to the electronic device. The electronic device can be a mobile electronic device.

The computer system 1501 includes a central processing unit (CPU, also "processor" and "computer processor" herein) 1505, which can be a single core or multi core processor, or a plurality of processors for parallel processing. The computer system 1501 also includes memory or memory location 1510 (e.g., random-access memory, read-only memory, flash memory), electronic storage unit 1515 (e.g., hard disk), communication interface 1520 (e.g., network adapter) for communicating with one or more other systems, and peripheral devices 1525, such as cache, other memory, data storage and/or electronic display adapters. The memory 1510, storage unit 1515, interface 1520 and peripheral devices 1525 are in communication with the CPU 1505 through a communication bus (solid lines), such as a motherboard. The storage unit 1515 can be a data storage unit (or data repository) for storing data. The computer system 1501 can be operatively coupled to a computer network ("network") 1530 with the aid of the communication interface 1520. The network 1530 can be the Internet, an internet and/or extranet, or an intranet and/or extranet that is in communication with the Internet. The network 1530 in some cases is a telecommunication and/or data network. The network 1530 can include one or more computer servers, which can enable distributed computing, such as cloud computing. The network 1530, in some cases with the aid of the computer system 1501, can implement a peer-to-peer network, which may enable devices coupled to the computer system 1501 to behave as a client or a server.

The CPU 1505 can execute a sequence of machine-readable instructions, which can be embodied in a program or software. The instructions may be stored in a memory location, such as the memory 1510. The instructions can be directed to the CPU 1505, which can subsequently program or otherwise configure the CPU 1505 to implement methods of the present disclosure. Examples of operations performed by the CPU 1505 can include fetch, decode, execute, and writeback.

The CPU 1505 can be part of a circuit, such as an integrated circuit. One or more other components of the system 1501 can be included in the circuit. In some cases, the circuit is an application specific integrated circuit (ASIC).

The storage unit 1515 can store files, such as drivers, libraries and saved programs. The storage unit 1515 can store user data, e.g., user preferences and user programs. The computer system 1501 in some cases can include one or more additional data storage units that are external to the computer system 1501, such as located on a remote server that is in communication with the computer system 1501 through an intranet or the Internet.

The computer system 1501 can communicate with one or more remote computer systems through the network 1530. For instance, the computer system 1501 can communicate with a remote computer system of a user (e.g., an operator). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 1501 via the network 1530.

Methods as described herein can be implemented by way of machine (e.g., computer processor) executable code stored on an electronic storage location of the computer system 1501, such as, for example, on the memory 1510 or electronic storage unit 1515. The machine executable or machine readable code can be provided in the form of software. During use, the code can be executed by the processor 1505. In some cases, the code can be retrieved from the storage unit 1515 and stored on the memory 1510 for ready access by the processor 1505. In some situations, the electronic storage unit 1515 can be precluded, and machine-executable instructions are stored on memory 1510.

The code can be pre-compiled and configured for use with a machine have a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 1501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 1501 can include or be in communication with an electronic display 1535 that comprises a user interface (UI) 1540. The UI can allow a user to set various conditions for the methods described herein, for example, PCR or sequencing conditions. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 1505. The algorithm can, for example, process the reads to generate a consequence sequence.

Figure 7:
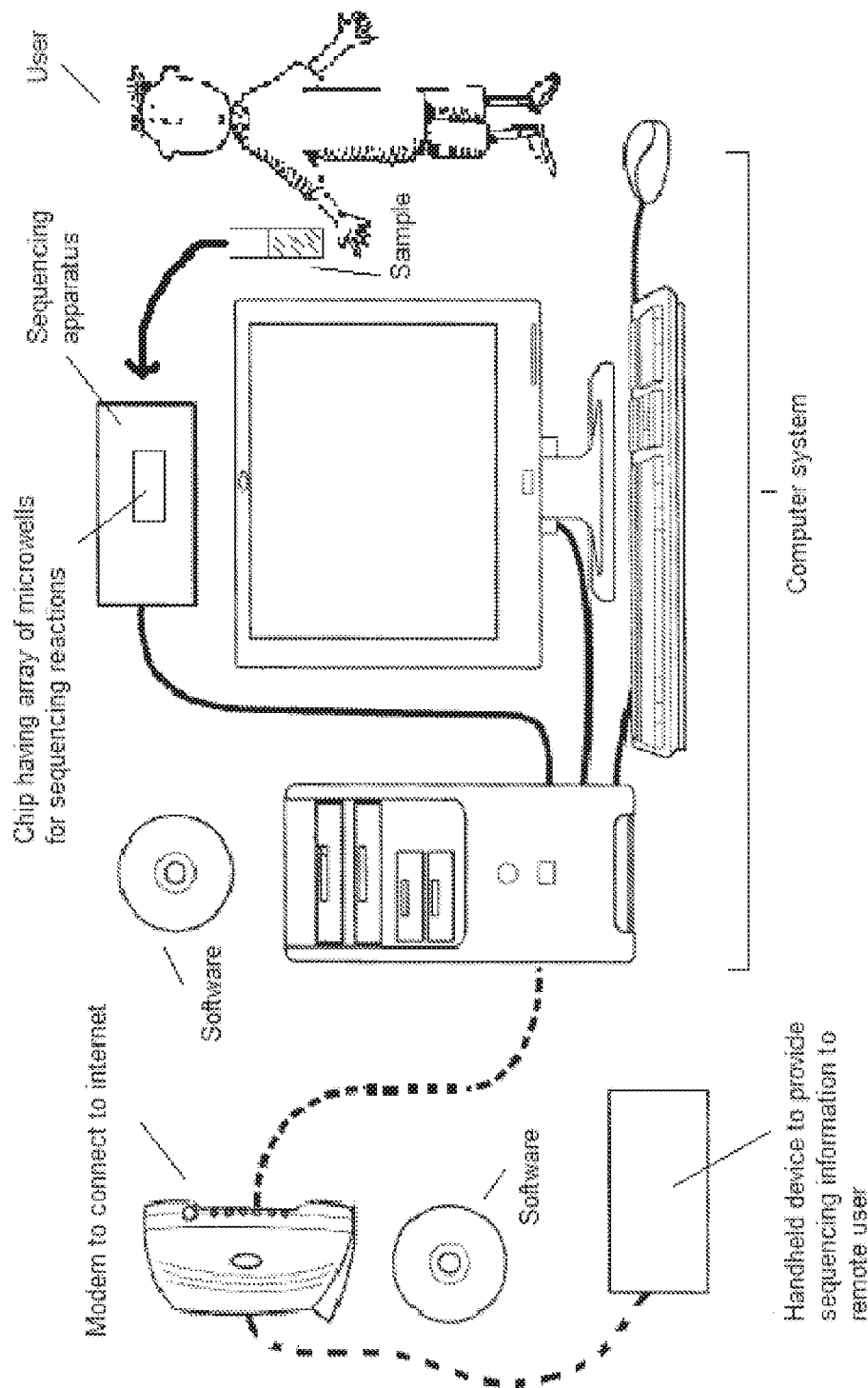
FIG. 7 is schematic representation of a system for analyzing a sample comprising nucleic acids from a user, including a sequencer; bioinformatic software and internet connection for report analysis by, for example, a hand held device or a desk top computer.

FIG. 7 schematically illustrates another system for analyzing a sample comprising nucleic acids from a subject. The system includes a sequencer, bioinformatic software and internet connection for report analysis by, for example, a hand held device or a desktop computer Disclosed herein is a system for analyzing a target nucleic acid molecule of a subject, comprising: a communication interface that receives nucleic acid sequence reads for a plurality of polynucleotide molecules that cover genomic loci of a target genome; computer memory that stores the nucleic acid sequence reads for the plurality of polynucleotide molecules received by the communication interface; and a computer processor operatively coupled to the communication interface and the memory and programmed to (i) group the plurality of sequence reads into families, wherein each family comprises sequence reads from one of the template polynucleotides, (ii) for each of the families, merge sequence reads to generate a consensus sequence, (iii) call the consensus sequence at a given genomic locus among the genomic loci, and (iv) detect at the given genomic locus any of genetic variants among the calls, frequency of a genetic alteration among the calls, total number of calls; and total number of alterations among the calls, wherein the genomic loci correspond to a plurality of genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1. The different variations of each component of the system are described throughout the disclosure within the methods and compositions. These individual components and variations thereof, are also applicable in this system.

4. Kits

Kits comprising the compositions as described herein. The kits can be useful in performing the methods as described herein. Disclosed herein is a kit comprising a plurality of oligonucleotide probes that selectively hybridize to least 5, 6, 7, 8, 9, 10, 20, 30, 40 or all genes selected from the group consisting of ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1. The number genes to which the oligonucleotide probes can selectively hybridize can vary. For example, the number of genes can comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, or 54. The kit can include a container that includes the plurality of oligonucleotide probes and instructions for performing any of the methods described herein.

The oligonucleotide probes can selectively hybridize to exon regions of the genes, e.g., of the at least 5 genes. In some cases, the oligonucleotide probes can selectively hybridize to at least 30 exons of the genes, e.g., of the at least 5 genes. In some cases, the multiple probes can selectively hybridize to each of the at least 30 exons. The probes that hybridize to each exon can have sequences that overlap with at least 1 other probe. In some embodiments, the oligoprobes can selectively hybridize to non-coding regions of genes disclosed herein, for example, intronic regions of the genes. The oligoprobes can also selectively hybridize to regions of genes comprising both exonic and intronic regions of the genes disclosed herein.

Any number of exons can be targeted by the oligonucleotide probes. For example, at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 400, 500, 600, 700, 800, 900, 1,000, or more, exons can be targeted.

The kit can comprise at least 4, 5, 6, 7, or 8 different library adaptors having distinct molecular barcodes and identical sample barcodes. The library adaptors may not be sequencing adaptors. For example, the library adaptors do not include flow cell sequences or sequences that permit the formation of hairpin loops for sequencing. The different variations and combinations of molecular barcodes and sample barcodes are described throughout, and are applicable to the kit. Further, in some cases, the adaptors are not sequencing adaptors. Additionally, the adaptors provided with the kit can also comprise sequencing adaptors. A sequencing adaptor can comprise a sequence hybridizing to one or more sequencing primers. A sequencing adaptor can further comprise a sequence hybridizing to a solid support, e.g., a flow cell sequence. For example, a sequencing adaptor can be a flow cell adaptor. The sequencing adaptors can be attached to one or both ends of a polynucleotide fragment. In some cases, the kit can comprise at least 8 different library adaptors having distinct molecular barcodes and identical sample barcodes. The library adaptors may not be sequencing adaptors. The kit can further include a sequencing adaptor having a first sequence that selectively hybridizes to the library adaptors and a second sequence that selectively hybridizes to a flow cell sequence. In another example, a sequencing adaptor can be hairpin shaped. For example, the hairpin shaped adaptor can comprise a complementary double stranded portion and a loop portion, where the double stranded portion can be attached (e.g., ligated) to a double-stranded polynucleotide. Hairpin shaped sequencing adaptors can be attached to both ends of a polynucleotide fragment to generate a circular molecule, which can be sequenced multiple times. A sequencing adaptor can be up to 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, or more bases from end to end. The sequencing adaptor can comprise 20-30, 20-40, 30-50, 30-60, 40-60, 40-70, 50-60, 50-70, bases from end to end. In a particular example, the sequencing adaptor can comprise 20-30 bases from end to end. In another example, the sequencing adaptor can comprise 50-60 bases from end to end. A sequencing adaptor can comprise one or more barcodes. For example, a sequencing adaptor can comprise a sample barcode. The sample barcode can comprise a pre-determined sequence. The sample barcodes can be used to identify the source of the polynucleotides. The sample barcode can be at least 1, 2, 3, 4, 5, 6, 7, 8, 9, 10, 11, 12, 13, 14, 15, 16, 17, 18, 19, 20, 21, 22, 23, 24, 25, or more (or any length as described throughout) nucleic acid bases, e.g., at least 8 bases. The barcode can be contiguous or non-contiguous sequences, as described above.

The library adaptors can be blunt ended and Y-shaped and can be less than or equal to 40 nucleic acid bases in length. Other variations of the can be found throughout and are applicable to the kit.

EXAMPLES

Example 1

Methods for Copy Number Variation Detection

Blood Collection 10-30 mL Blood samples are collected at room temperature. The samples are centrifuged to remove cells. Plasma is collected after centrifugation.

cfDNA Extraction

The sample is subjected to proteinase K digestion. DNA is precipitated with isopropanol. DNA is captured on a DNA purification column (e.g., a QIAamp DNA Blood Mini Kit) and eluted in 100 μsolution. DNAs below 500 bp are selected with Ampure SPRI magnetic bead capture (PEG/salt). The resulting production is suspended in 30 μl $H_2O$. Size distribution is checked (major peak=166 nucleotides; minor peak=330 nucleotides) and quantified. 5 ng of extracted DNA contain approximately 1700 haploid genome equivalents ("HGE"). The general correlation between the amount of DNA and HGE is as follow: 3 pg DNA=1 HGE; 3 ng DNA=1K HGE; 3 μg DNA=1M HGE; 10 pg DNA=3 HE; 10 ng DNA=3K HGE; 10 μg DNA=3M HGE.

"Single Molecule" Library Prep

High-efficiency DNA tagging (>80%) is performed by blunt-end repair and ligation with 8 different octomers (i.e., 64 combinations) with overloaded hairpin adaptors. 2.5 ng DNA (i.e. approximately 800 HGE) is used as the starting material. Each hairpin adaptor comprises a random sequence on its non-complementary portion. Both ends of each DNA fragment are attached with hairpin adaptors. Each tagged fragment can be identified by the random sequence on the hairpin adaptors and a 10 p endogenous sequence on the fragment.

Tagged DNA is amplified by 10 cycles of PCR to produce about 1-7 μg DNAs that contain approximately 500 copies of each of the 800 HGE in the starting material.

Buffer optimization, polymerase optimization and cycle reduction may be performed to optimize the PCR reactions. Amplification bias, e.g., non-specific bias, GC bias, and/or size bias are also reduced by optimization. Noise(s) (e.g., polymerase-introduced errors) are reduced by using high-fidelity polymerases.

The Library may be prepared using Verniata or Sequenom methods.

Sequences may be enriched as follow: DNAs with regions of interest (ROI) are captured using biotin-labeled bead with probe to ROIs. The ROIs are amplified with 12 cycles of PCR to generate a 2000 times amplification. The resulting DNA is then denatured and diluted to 8 pM and loaded into an Illumina sequencer.

Massively Parallel Sequencing 0.1 to 1% of the sample (approximately 100 pg) are used for sequencing.

Digital Bioinformatics

Sequence reads are grouped into families, with about 10 sequence reads in each family. Families are collapsed into consensus sequences by voting (e.g., biased voting) each position in a family. A base is called for consensus sequence if 8 or 9 members agree. A base is not called for consensus sequence if no more than 60% of the members agree.

The resulting consensus sequences are mapped to a reference genome. Each base in a consensus sequence is covered by about 3000 different families. A quality score for each sequence is calculated and sequences are filtered based on the their quality scores.

Sequence variation is detected by counting distribution of bases at each locus. If 98% of the reads have the same base (homozygous) and 2% have a different base, the locus is likely to have a sequence variant, presumably from cancer DNA.

CNV is detected by counting the total number of sequences (bases) mapping to a locus and comparing with a control locus. To increase CNV detection, CNV analysis is performed specific regions, including regions on ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET,SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, or NTRK1 genes.

Example 2

Method for Correcting Base Calling by Determining the Total Number Unseen Molecules in a Sample After fragments are amplified and the sequences of amplified fragments are read and aligned, the fragments are subjected to base calling. Variations in the number of amplified fragments and unseen amplified fragments can introduce errors in base calling. These variations are corrected by calculating the number of unseen amplified fragments.

When base calling for locus A (an arbitrary locus), it is first assumed that there are N amplified fragments. The sequence readouts can come from two types of fragments: double-strand fragments and single-strand fragments. The following is a theoretical example of calculating the total number of unseen molecules in a sample.

N is the total number of molecules in the sample.
Assuming 1000 is the number of duplexes detected.
Assuming 500 is the number of single-stranded molecule detected.
P is the probability of seeing a strand.
Q is the probability of not detecting a strand.

Since $Q=1-P$.

$1000=NP(2)$.

$500=N2PQ$.

$1000/P(2)=N$.

$500 \div 2PQ=N$.

$1000/P(2)=500 \div 2PQ$.

$1000*2PQ=500P(2)$.

$2000PQ=500P(2)$.

$2000Q=500P$.

$2000(1-P)=500P$.

$2000-2000P=500P$.

$2000=500P+2000P$.

$2000=2500P$.

$2000 \div 2500=P$.

$0.8=P$.

$1000/P(2)=N$.

$1000 \div 0.64=N$.

$1562=N$.

Number of unseen fragments=62.

Example 3

Identification of Genetic Variants in Cancer-Associated Somatic Variants in a Patient An assay is used to analyze a panel of genes to identify genetic variants in cancer-associated somatic variants with high sensitivity.

Cell-free DNA is extracted from plasma of a patient and amplified by PCR. Genetic variants are analyzed by massively parallel sequencing of the amplified target genes. For one set of genes, all exons are sequenced as such sequencing coverage had shown to have clinically utility (Table 1). For another set of genes, sequencing coverage included those exons with a previously reported somatic mutation (Table 2). The minimum detectable mutant allele (limit of detection) is dependent on the patient's sample cell-free DNA concentration, which varied from less than 10 to over 1,000 genomic equivalents per mL of peripheral blood. Amplification may not be detected in samples with lower amounts of cell-free DNA and/or low-level gene copy amplification. Certain sample or variant characteristics resulted in reduced analytic sensitivity, such as low sample quality or improper collection.

The percentage of genetic variants found in cell-free DNA circulating in blood is related to the unique tumor biology of this patient. Factors that affected the amount/percentages of detected genetic variants in circulating cell-free DNA in blood include tumor growth, turn-over, size, heterogeneity, vascularization, disease progression or treatment. Table 3 annotates the percentage, or allele frequency, of altered circulating cell-free DNA (% cfDNA) detected in this patient. Some of the detected genetic variants are listed in descending order by % cfDNA.

Genetic variants are detected in the circulating cell-free DNA isolated from this patient's blood specimen. These genetic variants are cancer-associated somatic variants, some of which have been associated with either increased or reduced clinical response to specific treatment. "Minor Alterations" are defined as those alterations detected at less than 10% the allele frequency of "Major Alterations". The detected allele frequencies of these alterations (Table 3) and associated treatments for this patient are annotated.

All genes listed in Tables 1 and 2 are analyzed as part of the Guardant360™ test. Amplification is not detected for ERBB2, EGFR, or MET in the circulating cell-free DNA isolated from this patient's blood specimen.

Patient test results comprising the genetic variants are listed in Table 4.

TABLE 1

Genes in which all exons are sequenced
GENES IN WHICH ALL EXONS ARE SEQUENCED

| | | | |
|---|---|---|---|
| ALK | <0.1% | APC | <0.1% |
| AR | <0.1% | BRAF | <0.1% |
| CDKN2A | <0.1% | EGFR | <0.1% |
| ERBB2 | <0.1% | FBXW7 | <0.1% |
| KRAS | <0.1% | MET | <0.1% |
| MYC | <0.1% | NOTCH1 | <0.1% |
| NRAS | <0.1% | PIK3CA | <0.1% |
| PTEN | <0.1% | PROC | <0.1% |
| RB1 | <0.1% | TP53 | <0.1% |

LOD: Limit of Detection. The minimum detectable mutant allele frequency for this specimen in which 80% of somatic variants is detected.

TABLE 2

Genes in which exons with a previously reported somatic mutation are sequenced
GENES IN WHICH EXONS WITH A PREVIOUSLY REPORTED SOMATIC MUTATION ARE SEQUENCED

| | | | |
|---|---|---|---|
| ABL1 | <0.1% | AKT1 | <0.1% |
| ATM | <0.1% | CDH1 | <0.1% |
| CSF1R | <0.1% | CTNNB1 | <0.1% |
| ERBB4 | <0.1% | EZH2 | <0.1% |
| FGFR1 | <0.1% | FGFR2 | <0.1% |
| FGFR3 | <0.1% | FLT3 | <0.1% |
| GNA11 | <0.1% | GNAQ | <0.1% |
| GNAS | <0.1% | HNF1A | <0.1% |
| HRAS | <0.1% | IDH1 | <0.1% |
| IDH2 | <0.1% | JAK2 | <0.1% |
| JAK3 | <0.1% | KDR | <0.1% |
| KIT | <0.1% | MLH1 | <0.1% |
| MPL | <0.1% | NPM1 | <0.1% |
| PDGFRA | <0.1% | PTPN11 | <0.1% |

TABLE 2-continued

Genes in which exons with a previously reported somatic mutation are sequenced
GENES IN WHICH EXONS WITH A PREVIOUSLY REPORTED SOMATIC MUTATION ARE SEQUENCED

| RET | <0.1% | SMAD4 | <0.1% |
|---|---|---|---|
| SMARCB1 | <0.1% | SMO | <0.1% |
| SRC | <0.1% | STK11 | <0.1% |
| TERT | <0.1% | VHL | <0.1% |

LOD: Limit of Detection. The minimum detectable mutant allele frequency for this specimen in which 80% of somatic variants is detected.

TABLE 3

Allele frequency of altered circulating cell-free DNA detected in this patient

| Gene | cfDNA with alterations (%) | cfDNA without alterations (%) |
|---|---|---|
| BRAE V600E | 8.9 | 91.1 |
| NRAS Q61K | 6.2 | 93.8 |
| JAK V61F | 1.5 | 98.6 |

TABLE 4

Genomic alterations detected in selected genes
Detected: 51 Genomic Alterations

| Gene | Chromosome | Position | Mutation (nt) | Mutation (AA) | Percentage | Cosmic ID | DBSNP ID |
|---|---|---|---|---|---|---|---|
| KRAS | 12 | 25368462 | C > T | | 100.0% | | rs4362222 |
| ALK | 2 | 29416572 | T > C | I1461V | 100.0% | | rs1670283 |
| ALK | 2 | 29444095 | C > T | | 100.0% | | rs1569156 |
| ALK | 2 | 29543663 | T > C | Q500Q | 100.0% | | rs2293564 |
| ALK | 2 | 29940529 | A > T | P234P | 100.0% | | rs2246745 |
| APC | 5 | 112176756 | T > A | V1822D | 100.0% | | rs459552 |
| CDKN2A | 9 | 21968199 | C > G | | 100.0% | COSM14251 | rs11515 |
| FGFR3 | 4 | 1807894 | G > A | T651T | 100.0% | | rs7688609 |
| NOTCH1 | 9 | 139410424 | A > G | | 100.0% | | rs3125006 |
| PDGFRA | 4 | 55141055 | A > G | P567P | 100.0% | | rs1873778 |
| HRAS | 11 | 534242 | A > G | H27H | 100.0% | COSM249860 | rs12628 |
| EGFR | 7 | 5214348 | C > T | N158N | 99.9% | COSM42978 | rs2072454 |
| TP53 | 17 | 7579472 | G > C | P72R | 99.8% | | rs1042522 |
| APC | 5 | 112162854 | T > C | Y486Y | 55.0% | | rs2229992 |
| APC | 5 | 112177171 | G > A | P1960P | 53.8% | | rs465899 |
| EGFR | 7 | 55266417 | T > C | T903T | 53.6% | | rs1140475 |
| APC | 5 | 112176325 | G > A | G1678G | 53.2% | | rs42427 |
| APC | 5 | 112176559 | T > G | S1756S | 53.0% | | rs866006 |
| EGFR | 7 | 55229255 | G > A | R521K | 53.0% | | |
| MET | 7 | 116397572 | A > G | Q648Q | 52.7% | | |
| APC | 5 | 112175770 | G > A | T1493T | 52.7% | | rs41115 |
| EGFR | 7 | 55249063 | G > A | Q787Q | 52.6% | | rs1050171 |
| NOTCH1 | 9 | 139411714 | T > C | | 52.4% | | rs11145767 |
| EGFR | 7 | 55238874 | T > A | T629T | 52.0% | | rs2227984 |
| ERBB2 | 17 | 37879588 | A > G | I655V | 51.6% | | rs1136201 |
| NOTCH1 | 9 | 139397707 | G > A | D1698D | 51.3% | COSM33747 | rs10521 |
| ALK | 2 | 30143499 | G > C | L9L | 51.0% | | rs4358080 |
| APC | 5 | 112164561 | G > A | A545A | 51.0% | | rs351771 |
| FLT3 | 13 | 28610183 | A > G | | 50.8% | | rs2491231 |
| NOTCH1 | 9 | 139418260 | A > G | N104N | 50.5% | | rs4489420 |
| ALK | 2 | 29444076 | G > T | | 50.4% | | rs1534545 |
| PIK3CA | 3 | 178917005 | A > G | | 50.3% | | rs3729674 |
| NOTCH1 | 9 | 139412197 | G > A | | 50.2% | | rs9411208 |
| ALK | 2 | 29455267 | A > G | G845G | 50.0% | COSM148825 | rs2256740 |
| KIT | 4 | 55593464 | A > C | M541L | 49.9% | COSM28026 | |
| NOTCH1 | 9 | 139391636 | G > A | D2185D | 48.9% | | rs2229974 |
| PDGFRA | 4 | 55152040 | C > T | V824V | 48.9% | COSM22413 | rs2228230 |
| ALK | 2 | 29416481 | T > C | K1491R | 48.9% | COSM1130802 | rs1881420 |
| ALK | 2 | 29445458 | G > T | G1125G | 48.6% | | rs3795850 |
| NOTCH1 | 9 | 139410177 | T > C | | 48.5% | | rs3124603 |
| RET | 10 | 43613843 | G > T | L769L | 48.2% | | rs1800861 |
| EGFR | 7 | 55214443 | G > A | | 48.0% | | rs7801956 |
| ALK | 2 | 29416366 | G > C | D1529E | 47.2% | | rs1881421 |
| EGFR | 7 | 55238087 | C > T | | 45.5% | | rs10258429 |
| RET | 10 | 43615633 | C > G | S904S | 44.8% | | rs1800863 |
| BRAF | 7 | 140453136 | A > T | V600E | 8.9% | COSM476 | |
| NRAS | 1 | 115256530 | G > T | Q61K | 6.2% | COSM580 | rs121913254 |
| JAK2 | 9 | 5073770 | G > T | V617F | 1.5% | COSM12600 | rs77375493 |

Example 4

Determining Patient-Specific Limits of Detection for Genes Analyzed by Guardant360™ Assays Using the method of Example 3, Genetic alterations in cell-free DNA of a patient are detected. The sequence reads of these genes include exon and/or intron sequences.

Limits of detection of the test are shown in Table 5. The limits of detection values are dependent on cell-free DNA concentration and sequencing coverage for each gene.

TABLE 5

Limits of Detection of selected genes in a patient using Guardant

Complete Exon and Partial Intron Coverage

| | | | | | |
|---|---|---|---|---|---|
| APC | 0.1% | AR * | 0.2% | ARID1A | |
| BRAF * | 0.1% | BRCA1 | | BRCA2 | |
| CCND1 * | | CCND2 * | | CCNE1 * | |
| CDK4 * | | CDK6 * | | CDKN2A | 0.1% |
| CDKN2B | | EGFR * | <0.1% | ERBB2 * | 0.1% |
| FGFR1 * | <0.1% | FGFR2 * | 0.1% | HRAS | 0.1% |
| KIT * | 0.1% | KRAS * | 0.1% | MET * | 0.1% |
| MYC * | 0.1% | NF1 | | NRAS | 0.1% |
| PDGFRA * | 0.1% | PIK3CA * | 0.1% | PTEN | 0.1% |
| RAF1 * | | TP53 | 0.1% | | |

Exons Covered with Reported Somatic Mutations

| | | | | | |
|---|---|---|---|---|---|
| AKT1 | 0.1% | ALK | <0.1% | ARAF | |
| ATM | 0.1% | CDH1 | 0.1% | CTNNB1 | 0.1% |
| ESR1 | | EZH2 | 0.1% | FBXW7 | 0.1% |
| FGFR3 | 0.1% | GATA3 | | GNA11 | 0.1% |
| GNAQ | | GNAS | 0.1% | HNF1A | 0.1% |
| IDH1 | 0.1% | IDH2 | 0.1% | JAK2 | 0.1% |
| JAK3 | 0.1% | MAP2K1 | | MAP2K2 | |
| MLH1 | 0.1% | MPL | 0.2% | NFE2L2 | |
| NOTCH1 | 0.1% | NPM1 | 0.1% | PTPN11 | 0.1% |
| RET | 0.1% | RHEB | | RHOA | |
| RIT1 | | ROS1 | | SMAD4 | 0.1% |
| SMO | 0.1% | SRC | <0.1% | STK11 | 0.2% |
| TERT | 0.1% | VHL | 0.2% | | |

Fusions

| | | | | | |
|---|---|---|---|---|---|
| ALK | <0.1% | RET | 0.1% | ROS1 | |
| NTRK1 | | | | | |

LOD: Limit of Detection. The minimum detectable mutant allele frequency for this specimen in which 80% of somatic variants is detected.
* indicates CNV genes.

Example 5

Correcting Sequence Errors Comparing Watson and Crick Sequences

Double-stranded cell-free DNA is isolated from the plasma of a patient. The cell-free DNA fragments are tagged using 16 different bubble-containing adaptors, each of which comprises a distinctive barcode. The bubble-containing adaptors are attached to both ends of each cell-free DNA fragment by ligation. After ligation, each of the cell-free DNA fragment can be distinctly identified by the sequence of the distinct barcodes and two 20 bp endogenous sequences at each end of the cell-free DNA fragment.

The tagged cell-free DNA fragments are amplified by PCR. The amplified fragments are enriched using beads comprising oligonucleotide probes that specifically bind to a group of cancer-associated genes. Therefore, cell-free DNA fragments from the group of cancer-associated genes are selectively enriched.

Sequencing adaptors, each of which comprises a sequencing primer binding site, a sample barcode, and a cell-flow sequence, are attached to the enriched DNA molecules. The resulting molecules are amplified by PCR.

Both strands of the amplified fragments are sequenced. Because each bubble-containing adaptor comprises a non-complementary portion (e.g., the bubble), the sequence of the one strand of the bubble-containing adaptor is different from the sequence of the other strand (complement). Therefore, the sequence reads of amplicons derived from the Watson strand of an original cell-free DNA can be distinguished from amplicons from the Crick strand of the original cell-free DNA by the attached bubble-containing adaptor sequences.

The sequence reads from a strand of an original cell-free DNA fragment are compared to the sequence reads from the other strand of the original cell-free DNA fragment. If a variant occurs in only the sequence reads from one strand, but not other strand, of the original cell-free DNA fragment, this variant will be identified as an error (e.g., resulted from PCR and/or amplification), rather than a true genetic variant.

The sequence reads are grouped into families. Errors in the sequence reads are corrected. The consensus sequence of each family is generated by collapsing.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method for analyzing sequencing reads of double-stranded cell-free deoxyribonucleic acid (cfDNA) molecules from a sample of a subject, comprising:

(a) tagging a plurality of double-stranded cfDNA molecules from a population of double-stranded cfDNA molecules from the sample with a set of library adaptors comprising a plurality of molecular barcodes to generate tagged parent polynucleotides,
wherein the tagging comprises ligating a plurality of library adaptors from the set of library adaptors to the plurality of double-stranded cfDNA molecules from the population using more than a 10× molar excess of library adaptors as compared to the double-stranded cfDNA molecules of the population;
wherein the tagging produces at least 20% of the double-stranded cfDNA molecules of the populations having library adaptors ligated to both ends of a molecule of the double-stranded cfDNA molecules;

(b) amplifying a plurality of the tagged parent polynucleotides to produce progeny polynucleotides;

(c) sequencing a plurality of the progeny polynucleotides to produce a set of sequencing reads; and (d) determining, based at least on sequence information from the molecular barcodes, individual double-stranded cfDNA molecules from among the tagged parent polynucleotides for which either (1) both a Watson strand and a Crick strand of the individual double-stranded cfDNA molecule are detected or (2) only one of a Watson strand or a Crick strand of the individual double-stranded cfDNA molecule is detected from a plurality of sequencing reads from the set of sequencing reads.

2. The method of claim 1, wherein the sample is selected from the group consisting of blood, plasma, serum, urine, saliva, mucosal excretions, sputum, stool, and tears.

3. The method of claim 1, wherein the plurality of library adaptors is ligated to the plurality of double-stranded cfDNA molecules by blunt-end ligation or sticky-end ligation.

4. The method of claim 1, wherein the ligating comprises using more than a 100×molar excess of library adaptors as compared to the double-stranded cfDNA molecules.

5. The method of claim 1, wherein the tagging produces at least 40% of the double-stranded cfDNA molecules of the population having library adaptors ligated to both ends of a molecule of the double-stranded cfDNA molecules.

6. The method of claim 1, wherein the plurality of molecular barcodes of the plurality of library adaptors has between 2 and 100,000 different molecular barcode sequences.

7. The method of claim 1, wherein the plurality of molecular barcodes of the plurality of library adaptors has between 5 and 100 different molecular barcode sequences.

8. The method of claim 7, wherein molecular barcodes of the plurality of molecular barcodes have a length of between 5 and 20 nucleotides.

9. The method of claim 1, wherein a plurality of the plurality of molecular barcodes have different sequences from one another and have an edit distance of at least 1 nucleotide base between one another.

10. The method of claim 1, wherein library adaptors of the plurality of library adaptors are Y-shaped adaptors.

11. The method of claim 1, further comprising selectively enriching a plurality of the progeny polynucleotides for genomic regions of interest.

12. The method of claim 11, wherein the genomic regions of interest comprises exon sequences.

13. The method of claim 11, wherein the genomic regions of interest comprise sequences from one or more genes selected from the group consisting of:

ALK, APC, BRAF, CDKN2A, EGFR, ERBB2, FBXW7, KRAS, MYC, NOTCH1, NRAS, PIK3CA, PTEN, RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1.

14. The method of claim 11, wherein selectively enriching the plurality of the progeny polynucleotides for the genomic regions of interest comprises using a set of probes that hybridize to at least a portion of the genomic regions of interest.

15. The method of claim 11, further comprising amplifying a plurality of the enriched progeny polynucleotides.

16. A method for analyzing double-stranded cell-free deoxyribonucleic acid (cfDNA) molecules from a sample of a subject, comprising:

(a) tagging a plurality of double-stranded cfDNA molecules from a population of double-stranded cfDNA molecules from the sample with a set of library adaptors comprising a plurality of molecular barcodes to generate tagged parent polynucleotides, wherein the tagging comprises ligating a plurality of library adaptors from the set of library adaptors to the plurality of double-stranded cfDNA molecules from the population using more than a 10× molar excess of library adaptors as compared to the double-stranded cfDNA molecules of the population;

wherein the tagging produces at least 20% of the double-stranded cfDNA molecules of the population having library adaptors ligated to both ends of a molecule of the double-stranded cfDNA molecules;

(b) amplifying a plurality of the tagged parent polynucleotides to progeny polynucleotides;

(c) determining nucleotide sequences of a plurality of the progeny polynucleotides; and (d) analyzing a plurality of the nucleotide sequences with a programmed computer processor, the analyzing comprising:

mapping a plurality of the nucleotide sequences to a reference sequence to produce mapped sequences, grouping a plurality of the mapped sequences into families based on a combination of sequence information from the molecular barcodes and start and stop positions of the mapped sequences, wherein a family of the families is representative of an individual double-stranded cfDNA molecule from among the tagged parent polynucleotides, and identifying a plurality of the families as having nucleotide sequences representing either (1) both a Watson strand and a Crick strand of an individual double-stranded cfDNA molecule from among the tagged parent polynucleotides or (2) only one of a Watson strand or a Crick strand of an individual double-stranded cfDNA molecule from among the tagged parent polynucleotides.

17. The method of claim 16, wherein the sample is selected from the group consisting of blood, plasma, serum, urine, saliva, mucosal excretions, sputum, stool, and tears.

18. The method of claim 16, wherein the plurality of library adaptors is ligated to the plurality of double-stranded cfDNA molecules by blunt-end ligation or sticky-end ligation.

19. The method of claim 16, wherein the ligating comprises using more than a 100× molar excess of library adaptors as compared to the double-stranded cfDNA molecules.

20. The method of claim 16, wherein the tagging produces at least 40% of the double-stranded cfDNA molecules of the population having library adaptors ligated to both ends of a molecule of the double-stranded cfDNA molecules.

21. The method of claim 16, further comprising selectively enriching a plurality of the progeny polynucleotides for genomic regions of interest prior to determining the nucleotide sequences, wherein the genomic regions of interest comprise sequences from one or more genes selected from the group consisting of:

ALK, APC, BRAF, CDKN2A, EGFR, ERBB2, FBXW7, KRAS, MYC, NOTCH1, NRAS, PIK3CA, PTEN,

RB1, TP53, MET, AR, ABL1, AKT1, ATM, CDH1, CSF1R, CTNNB1, ERBB4, EZH2, FGFR1, FGFR2, FGFR3, FLT3, GNA11, GNAQ, GNAS, HNF1A, HRAS, IDH1, IDH2, JAK2, JAK3, KDR, KIT, MLH1, MPL, NPM1, PDGFRA, PROC, PTPN11, RET, SMAD4, SMARCB1, SMO, SRC, STK11, VHL, TERT, CCND1, CDK4, CDKN2B, RAF1, BRCA1, CCND2, CDK6, NF1, TP53, ARID1A, BRCA2, CCNE1, ESR1, RIT1, GATA3, MAP2K1, RHEB, ROS1, ARAF, MAP2K2, NFE2L2, RHOA, and NTRK1.

22. The method of claim 16, wherein double-stranded cfDNA molecules of the plurality of double-stranded cfDNA molecules are non-uniquely tagged, wherein the double-stranded cfDNA molecules that map to a mappable base position of a reference sequence are tagged with a number of different molecular barcodes ranging from at least 2 to fewer than a number of the double-stranded cfDNA molecules that map to the mappable base position.

23. The method of claim 16, wherein nucleotide sequences determined from a Watson strand of an individual double-stranded cfDNA molecule from among the tagged parent polynucleotides are distinguished from nucleotide sequences generated from a Crick strand of the individual double-stranded cfDNA molecule from among the tagged parent polynucleotides based on sequence information from the molecular barcodes and/or sequence information from endogenous nucleotide sequences of the progeny polynucleotides.

24. The method of claim 1, wherein the tagging comprises non-uniquely tagging the plurality of double-stranded cfDNA molecules, wherein double-stranded cfDNA molecules of the plurality of double-stranded cfDNA molecules that map to a mappable base position of a reference sequence are tagged with a number of different molecular barcodes ranging from at least 2 to fewer than a number of the double-stranded cfDNA molecules that map to the mappable base position.

25. The method of claim 1, wherein sequencing reads produced from a Watson strand of a double-stranded cfDNA molecule from among the tagged parent polynucleotides are distinguished from sequencing reads generated from a Crick strand of the double-stranded cfDNA molecule from among the tagged parent polynucleotides based on sequence information from the molecular barcodes and/or sequence information from endogenous nucleotide sequences of the progeny polynucleotides.

26. The method of claim 1, further comprising, prior to (d), mapping a plurality of sequencing reads from the set of sequencing reads to a reference sequence to produce mapped sequencing reads.

27. The method of claim 26, further comprising grouping a plurality of the mapped sequencing reads into families based on a combination of sequence information from the molecular barcodes and start and stop positions of the mapped sequencing reads, wherein a family of the families is representative of an individual double-stranded cfDNA molecule from among the tagged parent polynucleotides.

28. The method of claim 1, further comprising:

(e) for a plurality of genetic loci of a reference sequence, estimating a number of tagged parent polynucleotides that map to the genetic locus of the reference sequence based at least on quantitative measures of the individual double-stranded cfDNA molecules determined in (d) that map to the genetic locus.

29. The method of claim 28, wherein estimating the number of tagged parent polynucleotides is further based on inferring, from at least the quantitative measures of the individual double-stranded cfDNA molecules determined in (d), a quantitative measure of individual double-stranded cfDNA molecules that map to the genetic locus for which neither a Watson strand nor a Crick strand is detected.

* * * * *

UNITED STATES PATENT AND TRADEMARK OFFICE
CERTIFICATE OF CORRECTION

PATENT NO. : 10,889,858 B2
APPLICATION NO. : 16/714579
DATED : January 12, 2021
INVENTOR(S) : AmirAli Talasaz et al.

Page 1 of 1

It is certified that error appears in the above-identified patent and that said Letters Patent is hereby corrected as shown below:

On the Title Page

Item (72), add inventor --Helmy Eltoukhy, Atherton CA (US)--

Item (63), Related U.S. Application Data:
Delete "of application No. 16/672,267, filed on Jan. 7, 2020, which is a continuation"

In the Specification

Column 1, Lines 6-7, delete "a continuation of U.S. application Ser. No. 16/672,267, filed Nov. 1, 2019, which is"

Signed and Sealed this
Twenty-seventh Day of September, 2022

Katherine Kelly Vidal
*Director of the United States Patent and Trademark Office*